United States Patent
Reynolds

(10) Patent No.: US 9,125,853 B2
(45) Date of Patent: Sep. 8, 2015

(54) TREATMENT OR PREVENTION OF INFECTION

(75) Inventor: Eric Charles Reynolds, Carlton (AU)

(73) Assignee: ORAL HEALTH AUSTRALIA PTY LTD, Carlton, Victoria (AU)

( * ) Notice: Subject to any disclaimer, the term of this patent is extended or adjusted under 35 U.S.C. 154(b) by 531 days.

(21) Appl. No.: 13/580,090

(22) PCT Filed: Feb. 25, 2011

(86) PCT No.: PCT/AU2011/000206
§ 371 (c)(1),
(2), (4) Date: Aug. 20, 2012

(87) PCT Pub. No.: WO2011/103633
PCT Pub. Date: Sep. 1, 2011

(65) Prior Publication Data
US 2013/0129768 A1    May 23, 2013

(30) Foreign Application Priority Data
Feb. 26, 2010  (AU) ................. 2010900846

(51) Int. Cl.
*A61K 39/02* (2006.01)
*A61K 45/06* (2006.01)
*A61K 39/00* (2006.01)

(52) U.S. Cl.
CPC ......... *A61K 39/0216* (2013.01); *A61K 39/0208* (2013.01); *A61K 45/06* (2013.01); *A61K 2039/542* (2013.01)

(58) Field of Classification Search
None
See application file for complete search history.

(56) References Cited

U.S. PATENT DOCUMENTS

| | | | |
|---|---|---|---|
| 6,511,666 | B1 | 1/2003 | Reynolds et al. |
| 6,962,706 | B1 | 11/2005 | O'Brien-Simpson et al. |
| 7,262,271 | B2 | 8/2007 | Reynolds et al. |
| 8,895,019 | B2 | 11/2014 | Dashper et al. |
| 2007/0036734 | A1 | 2/2007 | Tahara et al. |
| 2007/0053849 | A1* | 3/2007 | Doyle et al. ............ 424/50 |
| 2008/0175867 | A1 | 7/2008 | Reynolds et al. |
| 2009/0169568 | A1 | 7/2009 | Reynolds et al. |
| 2010/0092471 | A1 | 4/2010 | Dashper et al. |
| 2011/0081358 | A1 | 4/2011 | Reynolds et al. |

FOREIGN PATENT DOCUMENTS

| | | |
|---|---|---|
| EP | 0 726 276 A1 | 8/1996 |
| WO | WO 02/053178 A2 | 7/2002 |
| WO | WO 2005/019249 A2 | 3/2005 |
| WO | WO 2005/112992 A1 | 12/2005 |
| WO | WO 2011/014947 A1 | 2/2011 |

OTHER PUBLICATIONS

Ebersole et al., "Effects of Immunization with *Porphyromonas gingivalis* and *Prevotella intermedia* on Progression of Ligature-Induced Periodontitis in the Nonhuman Primate *Macaca fascicularis*," Infection and Immunity, Oct. 1991, pp. 3351-3359, vol. 59, No. 10.
Frazer et al., "Vaccination with recombinant adhesins from the RgpA-Kgp proteinase-adhesin complex protects against *Porphyromonas gingivalis* infection," Vaccine, 2006, pp. 6542-6554, vol. 24.
Gibson III et al., "Innate Immune Recognition of Invasive Bacteria Accelerates Atherosclerosis in Apolipoprotein E-Deficient Mice," Circulation, J. American Heart Assoc., Jun. 2004, pp. 2801-2806.
Klausen et al., "Vaccination Against *P. gingivalis* in Experimental Animals," Biology of the Species *Porphyromonas gingivalis*, 1993, Chapter 18, pp. 341-349, *CRC Press*.
Koizumi et al., "Nasal Immunization with a 40-kDa Outer Membrane Protein of *Porphyromonas gingivalis* Inhibits Atherosclerotic Plaque Accumulation Caused by Oral *P. gingivalie* Infection," Int. J. Oral-Med. Sci., 2008, pp. 150-158, vol. 6, No. 3.
O'Brien-Simpson et al., "An Immune Response Directed to Proteinase and Adhesin Functional Epitopes Protects against *Porphyromonas gingivalis*-Induced Periodontal Bone Loss," J. Immunol., 2005, pp. 3980-3989, vol. 175.
Page et al., "Immunization of *Macaca fascicularis* against experimental periodontitis using a vaccine containing cysteine proteases purified from *Porphyromonas gingivalis*," Oral Microbiology Immunology, 2007, pp. 162-168, vol. 22.
Rajapakse et al., "Immunication with the RgpA-Kgp Proteinase-Adhesin Complexes of *Porphyromonas gingivalis* Protects against Periodontal Bone Loss in the Rat Periodontitis Model," Infection and Immunity, May 2002, pp. 2480-2486, vol. 70, No. 5.
Tam et al., "Characterization of T Cell Responses to the RgpA-Kgp Proteinase-Adhesin Complexes of *Porphyromonas gingivalis* in BALB/c Mice," J. Immunol., 2008, pp. 4150-4158, vol. 181.
Yasaki-Inagaki et al., "Production of protective antibodies against *Porphyromonas gingivalis* strains by immunication with recombinant gingipain domains," FEMS Immunol. Med. Microbiol., 2006, pp. 287-295, vol. 47.
International Search Report issued on May 2, 2011 in application No. PCT/AU2011/000206.
Australian Search Report issued on Dec. 16, 2010 in application AU 2010900846.
Howell et al., "Nonsteroidal Antiinflammatory Drugs as Inhibitors of Periodontal Disease Progression," Critical Reviews in Oral Biology and Medicine, vol. 4, No. 2, pp. 177-196, 1993.
Supplementary European Search Report issued on Nov. 14, 2013 in application No. EP 11 74 6760.

\* cited by examiner

*Primary Examiner* — Anand Desai
(74) *Attorney, Agent, or Firm* — Foley & Lardner LLP

(57) ABSTRACT

The invention relates to a method of reducing the incidence or severity of a disease or condition in a subject, said disease or condition being one associated with the presence of a microbial pathogen in an oral tissue of a subject, and including the use of a composition forming an anti-microbial and an immunogen against a microbial pathogen.

15 Claims, 7 Drawing Sheets

SEQUENCE LISTING

```
<160> NUMBER OF SEQ ID NOS: 116

<210> SEQ ID NO 1
<211> LENGTH: 37
<212> TYPE: PRT
<213> ORGANISM: Porphyromonas gingivalis
<220> FEATURE:
<221> NAME/KEY: MOD_RES
<222> LOCATION: (6)..(6)
<223> OTHER INFORMATION: Gly or Ser
<220> FEATURE:
<221> NAME/KEY: MOD_RES
<222> LOCATION: (18)..(18)
<223> OTHER INFORMATION: Ser or Ala
<220> FEATURE:
<221> NAME/KEY: MOD_RES
<222> LOCATION: (23)..(23)
<223> OTHER INFORMATION: Ser or Leu
<220> FEATURE:
<221> NAME/KEY: MOD_RES
<222> LOCATION: (24)..(24)
<223> OTHER INFORMATION: Leu or Val
<220> FEATURE:
<221> NAME/KEY: MOD_RES
<222> LOCATION: (26)..(26)
<223> OTHER INFORMATION: Ala or Thr
<220> FEATURE:
<221> NAME/KEY: MOD_RES
<222> LOCATION: (27)..(27)
<223> OTHER INFORMATION: Thr or Ser
<220> FEATURE:
<221> NAME/KEY: MOD_RES
<222> LOCATION: (29)..(29)
<223> OTHER INFORMATION: Val or Leu
```

```
<220> FEATURE:
<221> NAME/KEY: MOD_RES
<222> LOCATION: (36)..(36)
<223> OTHER INFORMATION: Asp or Asn

<400> SEQUENCE: 1

Leu Asn Thr Gly Val Xaa Phe Ala Asn Tyr Thr Ala His Gly Ser Glu
1               5                   10                  15

Thr Xaa Trp Ala Asp Pro Xaa Xaa Thr Xaa Xaa Gln Xaa Lys Ala Leu
            20                  25                  30

Thr Asn Lys Xaa Lys
            35

<210> SEQ ID NO 2
<211> LENGTH: 37
<212> TYPE: PRT
<213> ORGANISM: Porphyromonas gingivalis
<220> FEATURE:
<221> NAME/KEY: MOD_RES
<222> LOCATION: (8)..(8)
<223> OTHER INFORMATION: Val or Ala

<400> SEQUENCE: 2

Phe Asn Gly Gly Ile Ser Leu Xaa Asn Tyr Thr Gly His Gly Ser Glu
1               5                   10                  15

Thr Ala Trp Gly Thr Ser His Phe Gly Thr Thr His Val Lys Gln Leu
            20                  25                  30

Thr Asn Ser Asn Gln
            35

<210> SEQ ID NO 3
<211> LENGTH: 7
<212> TYPE: PRT
<213> ORGANISM: Porphyromonas gingivalis

<400> SEQUENCE: 3

Val Ser Phe Ala Asn Tyr Thr
1               5

<210> SEQ ID NO 4
<211> LENGTH: 7
<212> TYPE: PRT
<213> ORGANISM: Porphyromonas gingivalis

<400> SEQUENCE: 4

Val Gly Phe Ala Asn Tyr Thr
1               5

<210> SEQ ID NO 5
<211> LENGTH: 8
<212> TYPE: PRT
<213> ORGANISM: Porphyromonas gingivalis

<400> SEQUENCE: 5

Gly Val Ser Phe Ala Asn Tyr Thr
1               5

<210> SEQ ID NO 6
<211> LENGTH: 8
<212> TYPE: PRT
<213> ORGANISM: Porphyromonas gingivalis

<400> SEQUENCE: 6

Gly Val Gly Phe Ala Asn Tyr Thr
```

```
<210> SEQ ID NO 7
<211> LENGTH: 8
<212> TYPE: PRT
<213> ORGANISM: Porphyromonas gingivalis

<400> SEQUENCE: 7

Val Ser Phe Ala Asn Tyr Thr Ala
1               5

<210> SEQ ID NO 8
<211> LENGTH: 8
<212> TYPE: PRT
<213> ORGANISM: Porphyromonas gingivalis

<400> SEQUENCE: 8

Val Gly Phe Ala Asn Tyr Thr Ala
1               5

<210> SEQ ID NO 9
<211> LENGTH: 6
<212> TYPE: PRT
<213> ORGANISM: Porphyromonas gingivalis

<400> SEQUENCE: 9

Glu Thr Ala Trp Ala Asp
1               5

<210> SEQ ID NO 10
<211> LENGTH: 6
<212> TYPE: PRT
<213> ORGANISM: Porphyromonas gingivalis

<400> SEQUENCE: 10

Glu Thr Ser Trp Ala Asp
1               5

<210> SEQ ID NO 11
<211> LENGTH: 6
<212> TYPE: PRT
<213> ORGANISM: Porphyromonas gingivalis

<400> SEQUENCE: 11

Thr Ala Trp Ala Asp Pro
1               5

<210> SEQ ID NO 12
<211> LENGTH: 6
<212> TYPE: PRT
<213> ORGANISM: Porphyromonas gingivalis

<400> SEQUENCE: 12

Thr Ser Trp Ala Asp Pro
1               5

<210> SEQ ID NO 13
<211> LENGTH: 7
<212> TYPE: PRT
<213> ORGANISM: Porphyromonas gingivalis

<400> SEQUENCE: 13

Ser Glu Thr Ala Trp Ala Asp
1               5
```

<210> SEQ ID NO 14
<211> LENGTH: 7
<212> TYPE: PRT
<213> ORGANISM: Porphyromonas gingivalis

<400> SEQUENCE: 14

Ser Glu Thr Ser Trp Ala Asp
1               5

<210> SEQ ID NO 15
<211> LENGTH: 7
<212> TYPE: PRT
<213> ORGANISM: Porphyromonas gingivalis

<400> SEQUENCE: 15

Glu Thr Ala Trp Ala Asp Pro
1               5

<210> SEQ ID NO 16
<211> LENGTH: 7
<212> TYPE: PRT
<213> ORGANISM: Porphyromonas gingivalis

<400> SEQUENCE: 16

Glu Thr Ser Trp Ala Asp Pro
1               5

<210> SEQ ID NO 17
<211> LENGTH: 7
<212> TYPE: PRT
<213> ORGANISM: Porphyromonas gingivalis

<400> SEQUENCE: 17

Thr Ala Trp Ala Asp Pro Leu
1               5

<210> SEQ ID NO 18
<211> LENGTH: 7
<212> TYPE: PRT
<213> ORGANISM: Porphyromonas gingivalis

<400> SEQUENCE: 18

Thr Ser Trp Ala Asp Pro Leu
1               5

<210> SEQ ID NO 19
<211> LENGTH: 8
<212> TYPE: PRT
<213> ORGANISM: Porphyromonas gingivalis

<400> SEQUENCE: 19

Gly Ser Glu Thr Ala Trp Ala Asp
1               5

<210> SEQ ID NO 20
<211> LENGTH: 8
<212> TYPE: PRT
<213> ORGANISM: Porphyromonas gingivalis

<400> SEQUENCE: 20

Gly Ser Glu Thr Ser Trp Ala Asp
1               5

<210> SEQ ID NO 21

```
<211> LENGTH: 8
<212> TYPE: PRT
<213> ORGANISM: Porphyromonas gingivalis

<400> SEQUENCE: 21

Ser Glu Thr Ala Trp Ala Asp Pro
1               5

<210> SEQ ID NO 22
<211> LENGTH: 8
<212> TYPE: PRT
<213> ORGANISM: Porphyromonas gingivalis

<400> SEQUENCE: 22

Ser Glu Thr Ser Trp Ala Asp Pro
1               5

<210> SEQ ID NO 23
<211> LENGTH: 8
<212> TYPE: PRT
<213> ORGANISM: Porphyromonas gingivalis

<400> SEQUENCE: 23

Glu Thr Ala Trp Ala Asp Pro Leu
1               5

<210> SEQ ID NO 24
<211> LENGTH: 8
<212> TYPE: PRT
<213> ORGANISM: Porphyromonas gingivalis

<400> SEQUENCE: 24

Glu Thr Ser Trp Ala Asp Pro Leu
1               5

<210> SEQ ID NO 25
<211> LENGTH: 8
<212> TYPE: PRT
<213> ORGANISM: Porphyromonas gingivalis

<400> SEQUENCE: 25

Thr Ala Trp Ala Asp Pro Leu Leu
1               5

<210> SEQ ID NO 26
<211> LENGTH: 8
<212> TYPE: PRT
<213> ORGANISM: Porphyromonas gingivalis

<400> SEQUENCE: 26

Thr Ser Trp Ala Asp Pro Leu Leu
1               5

<210> SEQ ID NO 27
<211> LENGTH: 23
<212> TYPE: PRT
<213> ORGANISM: Porphyromonas gingivalis
<220> FEATURE:
<221> NAME/KEY: MOD_RES
<222> LOCATION: (6)..(6)
<223> OTHER INFORMATION: Gly or Ser
<220> FEATURE:
<221> NAME/KEY: MOD_RES
<222> LOCATION: (18)..(18)
<223> OTHER INFORMATION: Ser or Ala
<220> FEATURE:
<221> NAME/KEY: MOD_RES
```

```
<222> LOCATION: (23)..(23)
<223> OTHER INFORMATION: Ser or Leu

<400> SEQUENCE: 27

Leu Asn Thr Gly Val Xaa Phe Ala Asn Tyr Thr Ala His Gly Ser Glu
1               5                   10                  15

Thr Xaa Trp Ala Asp Pro Xaa
            20

<210> SEQ ID NO 28
<211> LENGTH: 36
<212> TYPE: PRT
<213> ORGANISM: Porphyromonas gingivalis
<220> FEATURE:
<221> NAME/KEY: MOD_RES
<222> LOCATION: (5)..(5)
<223> OTHER INFORMATION: Gly or Ser
<220> FEATURE:
<221> NAME/KEY: MOD_RES
<222> LOCATION: (17)..(17)
<223> OTHER INFORMATION: Ser or Ala
<220> FEATURE:
<221> NAME/KEY: MOD_RES
<222> LOCATION: (22)..(22)
<223> OTHER INFORMATION: Ser or Leu
<220> FEATURE:
<221> NAME/KEY: MOD_RES
<222> LOCATION: (23)..(23)
<223> OTHER INFORMATION: Leu or Val
<220> FEATURE:
<221> NAME/KEY: MOD_RES
<222> LOCATION: (25)..(25)
<223> OTHER INFORMATION: Ala or Thr
<220> FEATURE:
<221> NAME/KEY: MOD_RES
<222> LOCATION: (26)..(26)
<223> OTHER INFORMATION: Thr or Ser
<220> FEATURE:
<221> NAME/KEY: MOD_RES
<222> LOCATION: (28)..(28)
<223> OTHER INFORMATION: Val or Leu
<220> FEATURE:
<221> NAME/KEY: MOD_RES
<222> LOCATION: (35)..(35)
<223> OTHER INFORMATION: Asp or Asn

<400> SEQUENCE: 28

Asn Thr Gly Val Xaa Phe Ala Asn Tyr Thr Ala His Gly Ser Glu Thr
1               5                   10                  15

Xaa Trp Ala Asp Pro Xaa Xaa Thr Xaa Xaa Gln Xaa Lys Ala Leu Thr
            20                  25                  30

Asn Lys Xaa Lys
        35

<210> SEQ ID NO 29
<211> LENGTH: 20
<212> TYPE: PRT
<213> ORGANISM: Porphyromonas gingivalis
<220> FEATURE:
<221> NAME/KEY: MOD_RES
<222> LOCATION: (2)..(2)
<223> OTHER INFORMATION: Gly or Ser
<220> FEATURE:
<221> NAME/KEY: MOD_RES
<222> LOCATION: (14)..(14)
<223> OTHER INFORMATION: Ser or Ala
<220> FEATURE:
<221> NAME/KEY: MOD_RES
<222> LOCATION: (19)..(19)
<223> OTHER INFORMATION: Ser or Leu
<220> FEATURE:
<221> NAME/KEY: MOD_RES
```

```
<222> LOCATION: (20)..(20)
<223> OTHER INFORMATION: Leu or Val

<400> SEQUENCE: 29

Val Xaa Phe Ala Asn Tyr Thr Ala His Gly Ser Glu Thr Xaa Trp Ala
1               5                   10                  15

Asp Pro Xaa Xaa
            20

<210> SEQ ID NO 30
<211> LENGTH: 22
<212> TYPE: PRT
<213> ORGANISM: Porphyromonas gingivalis

<400> SEQUENCE: 30

Leu Asn Thr Gly Val Ser Phe Ala Asn Tyr Thr Ala His Gly Ser Glu
1               5                   10                  15

Thr Ala Trp Ala Asp Pro
            20

<210> SEQ ID NO 31
<211> LENGTH: 23
<212> TYPE: PRT
<213> ORGANISM: Porphyromonas gingivalis
<220> FEATURE:
<221> NAME/KEY: MOD_RES
<222> LOCATION: (8)..(8)
<223> OTHER INFORMATION: Val or Ala

<400> SEQUENCE: 31

Phe Asn Gly Gly Ile Ser Leu Xaa Asn Tyr Thr Gly His Gly Ser Glu
1               5                   10                  15

Thr Ala Trp Gly Thr Ser His
            20

<210> SEQ ID NO 32
<211> LENGTH: 36
<212> TYPE: PRT
<213> ORGANISM: Porphyromonas gingivalis
<220> FEATURE:
<221> NAME/KEY: MOD_RES
<222> LOCATION: (7)..(7)
<223> OTHER INFORMATION: Val or Ala

<400> SEQUENCE: 32

Asn Gly Gly Ile Ser Leu Xaa Asn Tyr Thr Gly His Gly Ser Glu Thr
1               5                   10                  15

Ala Trp Gly Thr Ser His Phe Gly Thr Thr His Val Lys Gln Leu Thr
            20                  25                  30

Asn Ser Asn Gln
        35

<210> SEQ ID NO 33
<211> LENGTH: 20
<212> TYPE: PRT
<213> ORGANISM: Porphyromonas gingivalis
<220> FEATURE:
<221> NAME/KEY: MOD_RES
<222> LOCATION: (4)..(4)
<223> OTHER INFORMATION: Val or Ala

<400> SEQUENCE: 33

Ile Ser Leu Xaa Asn Tyr Thr Gly His Gly Ser Glu Thr Ala Trp Gly
1               5                   10                  15
```

Thr Ser His Phe
            20

<210> SEQ ID NO 34
<211> LENGTH: 21
<212> TYPE: PRT
<213> ORGANISM: Porphyromonas gingivalis

<400> SEQUENCE: 34

Phe Asn Gly Gly Ile Ser Leu Ala Asn Tyr Thr Gly His Gly Ser Glu
1               5                   10                  15

Thr Ala Trp Gly Thr
            20

<210> SEQ ID NO 35
<211> LENGTH: 362
<212> TYPE: PRT
<213> ORGANISM: Porphyromonas gingivalis

<400> SEQUENCE: 35

Ala Asn Glu Ala Lys Val Val Leu Ala Ala Asp Asn Val Trp Gly Asp
1               5                   10                  15

Asn Thr Gly Tyr Gln Phe Leu Asp Ala Asp His Asn Thr Phe Gly
            20                  25                  30

Ser Val Ile Pro Ala Thr Gly Pro Leu Phe Thr Gly Thr Ala Ser Ser
            35                  40                  45

Asn Leu Tyr Ser Ala Asn Phe Glu Tyr Leu Ile Pro Ala Asn Ala Asp
50                  55                  60

Pro Val Val Thr Thr Gln Asn Ile Ile Val Thr Gly Gln Gly Glu Val
65                  70                  75                  80

Val Ile Pro Gly Gly Val Tyr Asp Tyr Cys Ile Thr Asn Pro Glu Pro
                85                  90                  95

Ala Ser Gly Lys Met Trp Ile Ala Gly Asp Gly Asn Gln Pro Ala
            100                 105                 110

Arg Tyr Asp Asp Phe Thr Phe Glu Ala Gly Lys Lys Tyr Thr Phe Thr
            115                 120                 125

Met Arg Arg Ala Gly Met Gly Asp Gly Thr Asp Met Glu Val Glu Asp
            130                 135                 140

Asp Ser Pro Ala Ser Tyr Thr Tyr Thr Val Tyr Arg Asp Gly Thr Lys
145                 150                 155                 160

Ile Lys Glu Gly Leu Thr Ala Thr Thr Phe Glu Glu Asp Gly Val Ala
                165                 170                 175

Ala Gly Asn His Glu Tyr Cys Val Glu Val Lys Tyr Thr Ala Gly Val
            180                 185                 190

Ser Pro Lys Val Cys Lys Asp Val Thr Val Glu Gly Ser Asn Glu Phe
            195                 200                 205

Ala Pro Val Gln Asn Leu Thr Gly Ser Ser Val Gly Gln Lys Val Thr
            210                 215                 220

Leu Lys Trp Asp Ala Pro Asn Gly Thr Pro Asn Pro Asn Pro Asn Pro
225                 230                 235                 240

Asn Pro Asn Pro Gly Thr Thr Leu Ser Glu Ser Phe Glu Asn Gly Ile
                245                 250                 255

Pro Ala Ser Trp Lys Thr Ile Asp Ala Asp Gly Asp Gly His Gly Trp
            260                 265                 270

Lys Pro Gly Asn Ala Pro Gly Ile Ala Gly Tyr Asn Ser Asn Gly Cys
            275                 280                 285

```
Val Tyr Ser Glu Ser Phe Gly Leu Gly Gly Ile Gly Val Leu Thr Pro
    290                 295                 300
Asp Asn Tyr Leu Ile Thr Pro Ala Leu Asp Leu Pro Asn Gly Gly Lys
305                 310                 315                 320
Leu Thr Phe Trp Val Cys Ala Gln Asp Ala Asn Tyr Ala Ser Glu His
                325                 330                 335
Tyr Ala Val Tyr Ala Ser Ser Thr Gly Asn Asp Ala Ser Asn Phe Thr
            340                 345                 350
Asn Ala Leu Leu Glu Glu Thr Ile Thr Ala
            355                 360

<210> SEQ ID NO 36
<211> LENGTH: 231
<212> TYPE: PRT
<213> ORGANISM: Porphyromonas gingivalis

<400> SEQUENCE: 36

Phe Leu Leu Asp Ala Asp His Asn Thr Phe Gly Ser Val Ile Pro Ala
1               5                   10                  15
Thr Gly Pro Leu Phe Thr Gly Thr Ala Ser Ser Asn Leu Tyr Ser Ala
            20                  25                  30
Asn Phe Glu Tyr Leu Ile Pro Ala Asn Ala Asp Pro Val Val Thr Thr
        35                  40                  45
Gln Asn Ile Ile Val Thr Gly Gln Gly Glu Val Val Ile Pro Gly Gly
    50                  55                  60
Val Tyr Asp Tyr Cys Ile Thr Asn Pro Glu Pro Ala Ser Gly Lys Met
65                  70                  75                  80
Trp Ile Ala Gly Asp Gly Gly Asn Gln Pro Ala Arg Tyr Asp Asp Phe
                85                  90                  95
Thr Phe Glu Ala Gly Lys Lys Tyr Thr Phe Thr Met Arg Arg Ala Gly
            100                 105                 110
Met Gly Asp Gly Thr Asp Met Glu Val Glu Asp Ser Pro Ala Ser
            115                 120                 125
Tyr Thr Tyr Thr Val Tyr Arg Asp Gly Thr Lys Ile Lys Glu Gly Leu
    130                 135                 140
Thr Ala Thr Thr Phe Glu Glu Asp Gly Val Ala Ala Gly Asn His Glu
145                 150                 155                 160
Tyr Cys Val Glu Val Lys Tyr Thr Ala Gly Val Ser Pro Lys Val Cys
                165                 170                 175
Lys Asp Val Thr Val Glu Gly Ser Asn Glu Phe Ala Pro Val Gln Asn
            180                 185                 190
Leu Thr Gly Ser Ser Val Gly Gln Lys Val Thr Leu Lys Trp Asp Ala
        195                 200                 205
Pro Asn Gly Thr Pro Asn Pro Asn Pro Asn Pro Asn Pro Asn Pro Gly
    210                 215                 220
Thr Thr Leu Ser Glu Ser Phe
225                 230

<210> SEQ ID NO 37
<211> LENGTH: 306
<212> TYPE: PRT
<213> ORGANISM: Porphyromonas gingivalis

<400> SEQUENCE: 37

Trp Gly Asp Asn Thr Gly Tyr Gln Phe Leu Leu Asp Ala Asp His Asn
1               5                   10                  15
```

```
Thr Phe Gly Ser Val Ile Pro Ala Thr Gly Pro Leu Phe Thr Gly Thr
                 20                  25                  30

Ala Ser Ser Asn Leu Tyr Ser Ala Asn Phe Glu Tyr Leu Ile Pro Ala
         35                  40                  45

Asn Ala Asp Pro Val Val Thr Thr Gln Asn Ile Ile Val Thr Gly Gln
 50                  55                  60

Gly Glu Val Val Ile Pro Gly Gly Val Tyr Asp Tyr Cys Ile Thr Asn
 65                  70                  75                  80

Pro Glu Pro Ala Ser Gly Lys Met Trp Ile Ala Gly Asp Gly Gly Asn
                 85                  90                  95

Gln Pro Ala Arg Tyr Asp Asp Phe Thr Phe Glu Ala Gly Lys Lys Tyr
                100                 105                 110

Thr Phe Thr Met Arg Arg Ala Gly Met Gly Asp Gly Thr Asp Met Glu
        115                 120                 125

Val Glu Asp Asp Ser Pro Ala Ser Tyr Thr Tyr Thr Val Tyr Arg Asp
130                 135                 140

Gly Thr Lys Ile Lys Glu Gly Leu Thr Ala Thr Thr Phe Glu Glu Asp
145                 150                 155                 160

Gly Val Ala Ala Gly Asn His Glu Tyr Cys Val Glu Val Lys Tyr Thr
                165                 170                 175

Ala Gly Val Ser Pro Lys Val Cys Lys Asp Val Thr Val Glu Gly Ser
                180                 185                 190

Asn Glu Phe Ala Pro Val Gln Asn Leu Thr Gly Ser Ser Val Gly Gln
                195                 200                 205

Lys Val Thr Leu Lys Trp Asp Ala Pro Asn Gly Thr Pro Asn Pro Asn
210                 215                 220

Pro Asn Pro Asn Pro Asn Pro Gly Thr Thr Leu Ser Glu Ser Phe Glu
225                 230                 235                 240

Asn Gly Ile Pro Ala Ser Trp Lys Thr Ile Asp Ala Asp Gly Asp Gly
                245                 250                 255

His Gly Trp Lys Pro Gly Asn Ala Pro Gly Ile Ala Gly Tyr Asn Ser
                260                 265                 270

Asn Gly Cys Val Tyr Ser Glu Ser Phe Gly Leu Gly Gly Ile Gly Val
                275                 280                 285

Leu Thr Pro Asp Asn Tyr Leu Ile Thr Pro Ala Leu Asp Leu Pro Asn
290                 295                 300

Gly Gly
305

<210> SEQ ID NO 38
<211> LENGTH: 362
<212> TYPE: PRT
<213> ORGANISM: Porphyromonas gingivalis

<400> SEQUENCE: 38

Ser Gly Gln Ala Glu Ile Val Leu Glu Ala His Asp Val Trp Asn Asp
 1               5                  10                  15

Gly Ser Gly Tyr Gln Ile Leu Leu Asp Ala Asp His Asp Gln Tyr Gly
                 20                  25                  30

Gln Val Ile Pro Ser Asp Thr His Thr Leu Trp Pro Asn Cys Ser Val
         35                  40                  45

Pro Ala Asn Leu Phe Ala Pro Phe Glu Tyr Thr Val Pro Glu Asn Ala
 50                  55                  60

Asp Pro Ser Cys Ser Pro Thr Asn Met Ile Met Asp Gly Thr Ala Ser
 65                  70                  75                  80
```

```
Val Asn Ile Pro Ala Gly Thr Tyr Asp Phe Ala Ile Ala Pro Gln
            85                  90                  95

Ala Asn Ala Lys Ile Trp Ile Ala Gly Gln Gly Pro Thr Lys Glu Asp
            100                 105                 110

Asp Tyr Val Phe Glu Ala Gly Lys Lys Tyr His Phe Leu Met Lys Lys
            115                 120                 125

Met Gly Ser Gly Asp Gly Thr Glu Leu Thr Ile Ser Glu Gly Gly Gly
    130                 135                 140

Ser Asp Tyr Thr Tyr Thr Val Tyr Arg Asp Gly Thr Lys Ile Lys Glu
145                 150                 155                 160

Gly Leu Thr Ala Thr Thr Phe Glu Glu Asp Gly Val Ala Thr Gly Asn
                    165                 170                 175

His Glu Tyr Cys Val Glu Val Lys Tyr Thr Ala Gly Val Ser Pro Lys
                180                 185                 190

Val Cys Lys Asp Val Thr Val Glu Gly Ser Asn Glu Phe Ala Pro Val
            195                 200                 205

Gln Asn Leu Thr Gly Ser Ala Val Gly Gln Lys Val Thr Leu Lys Trp
            210                 215                 220

Asp Ala Pro Asn Gly Thr Pro Asn Pro Asn Pro Asn Pro Asn Pro Asn
225                 230                 235                 240

Pro Asn Pro Gly Thr Thr Thr Leu Ser Glu Ser Phe Glu Asn Gly Ile
                245                 250                 255

Pro Ala Ser Trp Lys Thr Ile Asp Ala Asp Gly Asp Gly His Gly Trp
                260                 265                 270

Lys Pro Gly Asn Ala Pro Gly Ile Ala Gly Tyr Asn Ser Asn Gly Cys
            275                 280                 285

Val Tyr Ser Glu Ser Phe Gly Leu Gly Gly Ile Gly Val Leu Thr Pro
            290                 295                 300

Asp Asn Tyr Leu Ile Thr Pro Ala Leu Asp Leu Pro Asn Gly Gly Lys
305                 310                 315                 320

Leu Thr Phe Trp Val Cys Ala Gln Asp Ala Asn Tyr Ala Ser Glu His
                325                 330                 335

Tyr Ala Val Tyr Ala Ser Ser Thr Gly Asn Asp Ala Ser Asn Phe Thr
            340                 345                 350

Asn Ala Leu Leu Glu Glu Thr Ile Thr Ala
            355                 360

<210> SEQ ID NO 39
<211> LENGTH: 141
<212> TYPE: PRT
<213> ORGANISM: Porphyromonas gingivalis

<400> SEQUENCE: 39

Asp Asp Tyr Val Phe Glu Ala Gly Lys Lys Tyr His Phe Leu Met Lys
1               5                   10                  15

Lys Met Gly Ser Gly Asp Gly Thr Glu Leu Thr Ile Ser Glu Gly Gly
                20                  25                  30

Gly Ser Asp Tyr Thr Tyr Thr Val Tyr Arg Asp Gly Thr Lys Ile Lys
            35                  40                  45

Glu Gly Leu Thr Ala Thr Thr Phe Glu Glu Asp Gly Val Ala Thr Gly
        50                  55                  60

Asn His Glu Tyr Cys Val Glu Val Lys Tyr Thr Ala Gly Val Ser Pro
65                  70                  75                  80

Lys Val Cys Lys Asp Val Thr Val Glu Gly Ser Asn Glu Phe Ala Pro
```

Val Gln Asn Leu Thr Gly Ser Ala Val Gly Gln Lys Val Thr Leu Lys
            100                 105                 110

Trp Asp Ala Pro Asn Gly Thr Pro Asn Pro Asn Pro Asn Pro Asn Pro
            115                 120                 125

Asn Pro Asn Pro Gly Thr Thr Thr Leu Ser Glu Ser Phe
            130                 135                 140

<210> SEQ ID NO 40
<211> LENGTH: 119
<212> TYPE: PRT
<213> ORGANISM: Porphyromonas gingivalis

<400> SEQUENCE: 40

Ala Asp Phe Thr Glu Thr Phe Glu Ser Ser Thr His Gly Glu Ala Pro
1               5                   10                  15

Ala Glu Trp Thr Thr Ile Asp Ala Asp Gly Asp Gly Gln Gly Trp Leu
            20                  25                  30

Cys Leu Ser Ser Gly Gln Leu Asp Trp Leu Thr Ala His Gly Gly Ser
        35                  40                  45

Asn Val Val Ser Ser Phe Ser Trp Asn Gly Met Ala Leu Asn Pro Asp
    50                  55                  60

Asn Tyr Leu Ile Ser Lys Asp Val Thr Gly Ala Thr Lys Val Lys Tyr
65                  70                  75                  80

Tyr Tyr Ala Val Asn Asp Gly Phe Pro Gly Asp His Tyr Ala Val Met
                85                  90                  95

Ile Ser Lys Thr Gly Thr Asn Ala Gly Asp Phe Thr Val Val Phe Glu
            100                 105                 110

Glu Thr Pro Asn Gly Ile Asn
        115

<210> SEQ ID NO 41
<211> LENGTH: 133
<212> TYPE: PRT
<213> ORGANISM: Porphyromonas gingivalis

<400> SEQUENCE: 41

Pro Gln Ser Val Trp Ile Glu Arg Thr Val Asp Leu Pro Ala Gly Thr
1               5                   10                  15

Lys Tyr Val Ala Phe Arg His Tyr Asn Cys Ser Asp Leu Asn Tyr Ile
            20                  25                  30

Leu Leu Asp Asp Ile Gln Phe Thr Met Gly Gly Ser Pro Thr Pro Thr
        35                  40                  45

Asp Tyr Thr Tyr Thr Val Tyr Arg Asp Gly Thr Lys Ile Lys Glu Gly
    50                  55                  60

Leu Thr Glu Thr Thr Phe Glu Glu Asp Gly Val Ala Thr Gly Asn His
65                  70                  75                  80

Glu Tyr Cys Val Glu Val Lys Tyr Thr Ala Gly Val Ser Pro Lys Lys
                85                  90                  95

Cys Val Asn Val Thr Val Asn Ser Thr Gln Phe Asn Pro Val Gln Asn
            100                 105                 110

Leu Thr Ala Glu Gln Ala Pro Asn Ser Met Asp Ala Ile Leu Lys Trp
        115                 120                 125

Asn Ala Pro Ala Ser
        130

```
<210> SEQ ID NO 42
<211> LENGTH: 120
<212> TYPE: PRT
<213> ORGANISM: Porphyromonas gingivalis

<400> SEQUENCE: 42

Ala Glu Val Leu Asn Glu Asp Phe Glu Asn Gly Ile Pro Ala Ser Trp
1               5                   10                  15

Lys Thr Ile Asp Ala Asp Gly Asp Gly Asn Asn Trp Thr Thr Thr Pro
            20                  25                  30

Pro Pro Gly Gly Ser Ser Phe Ala Gly His Asn Ser Ala Ile Cys Val
                35                  40                  45

Ser Ser Ala Ser Tyr Ile Asn Phe Glu Gly Pro Gln Asn Pro Asp Asn
        50                  55                  60

Tyr Leu Val Thr Pro Glu Leu Ser Leu Pro Gly Gly Thr Leu Thr
65                  70                  75                  80

Phe Trp Val Cys Ala Gln Asp Ala Asn Tyr Ala Ser Glu His Tyr Ala
                85                  90                  95

Val Tyr Ala Ser Ser Thr Gly Asn Asp Ala Ser Asn Phe Ala Asn Ala
                100                 105                 110

Leu Leu Glu Glu Val Leu Thr Ala
            115                 120

<210> SEQ ID NO 43
<211> LENGTH: 185
<212> TYPE: PRT
<213> ORGANISM: Porphyromonas gingivalis

<400> SEQUENCE: 43

Thr Val Val Thr Ala Pro Glu Ala Ile Arg Gly Thr Arg Ala Gln Gly
1               5                   10                  15

Thr Trp Tyr Gln Lys Thr Val Gln Leu Pro Ala Gly Thr Lys Tyr Val
            20                  25                  30

Ala Phe Arg His Phe Gly Cys Thr Asp Phe Phe Trp Ile Asn Leu Asp
                35                  40                  45

Asp Val Val Ile Thr Ser Gly Asn Ala Pro Ser Tyr Thr Tyr Thr Ile
        50                  55                  60

Tyr Arg Asn Asn Thr Gln Ile Ala Ser Gly Val Thr Glu Thr Thr Tyr
65                  70                  75                  80

Arg Asp Pro Asp Leu Ala Thr Gly Phe Tyr Thr Tyr Gly Val Lys Val
                85                  90                  95

Val Tyr Pro Asn Gly Glu Ser Ala Ile Glu Thr Ala Thr Leu Asn Ile
                100                 105                 110

Thr Ser Leu Ala Asp Val Thr Ala Gln Lys Pro Tyr Thr Leu Thr Val
            115                 120                 125

Val Gly Lys Thr Ile Thr Val Thr Cys Gln Gly Glu Ala Met Ile Tyr
        130                 135                 140

Asp Met Asn Gly Arg Arg Leu Ala Gly Arg Asn Thr Val Val Tyr
145                 150                 155                 160

Thr Ala Gln Gly Gly His Tyr Ala Val Met Val Val Asp Gly Lys
                165                 170                 175

Ser Tyr Val Glu Lys Leu Ala Val Lys
                180                 185

<210> SEQ ID NO 44
<211> LENGTH: 119
<212> TYPE: PRT
```

<213> ORGANISM: Porphyromonas gingivalis

<400> SEQUENCE: 44

Ala Asp Phe Thr Glu Thr Phe Glu Ser Ser Thr His Gly Glu Ala Pro
1               5                   10                  15

Ala Glu Trp Thr Thr Ile Asp Ala Asp Gly Asp Gly Gln Gly Trp Leu
            20                  25                  30

Cys Leu Ser Ser Gly Gln Leu Asp Trp Leu Thr Ala His Gly Gly Thr
        35                  40                  45

Asn Val Val Ser Ser Phe Ser Trp Asn Gly Met Ala Leu Asn Pro Asp
    50                  55                  60

Asn Tyr Leu Ile Ser Lys Asp Val Thr Gly Ala Thr Lys Val Lys Tyr
65                  70                  75                  80

Tyr Tyr Ala Val Asn Asp Gly Phe Pro Gly Asp His Tyr Ala Val Met
                85                  90                  95

Ile Ser Lys Thr Gly Thr Asn Ala Gly Asp Phe Thr Val Val Phe Glu
            100                 105                 110

Glu Thr Pro Asn Gly Ile Asn
        115

<210> SEQ ID NO 45
<211> LENGTH: 131
<212> TYPE: PRT
<213> ORGANISM: Porphyromonas gingivalis

<400> SEQUENCE: 45

Pro Gln Ser Val Trp Ile Glu Arg Thr Val Asp Leu Pro Ala Gly Thr
1               5                   10                  15

Lys Tyr Val Ala Phe Arg His Tyr Asn Cys Ser Asp Leu Asn Tyr Ile
            20                  25                  30

Leu Leu Asp Asp Ile Gln Phe Thr Met Gly Gly Ser Pro Thr Pro Thr
        35                  40                  45

Asp Tyr Thr Tyr Thr Val Tyr Arg Asp Gly Thr Lys Ile Lys Glu Gly
    50                  55                  60

Leu Thr Glu Thr Thr Phe Glu Glu Asp Gly Val Ala Thr Gly Asn His
65                  70                  75                  80

Glu Tyr Cys Val Glu Val Lys Tyr Thr Ala Gly Val Ser Pro Lys Lys
                85                  90                  95

Cys Val Asn Val Thr Val Asn Ser Thr Gln Phe Asn Pro Val Lys Asn
            100                 105                 110

Leu Lys Ala Gln Pro Asp Gly Gly Asp Val Val Leu Lys Trp Glu Ala
        115                 120                 125

Pro Ser Ala
    130

<210> SEQ ID NO 46
<211> LENGTH: 275
<212> TYPE: PRT
<213> ORGANISM: Porphyromonas gingivalis

<400> SEQUENCE: 46

Ala Asn Glu Ala Lys Val Val Leu Ala Ala Asp Asn Val Trp Gly Asp
1               5                   10                  15

Asn Thr Gly Tyr Gln Phe Leu Leu Asp Ala Asp His Asn Thr Phe Gly
            20                  25                  30

Ser Val Ile Pro Ala Thr Gly Pro Leu Phe Thr Gly Thr Ala Ser Ser
        35                  40                  45

```
Asp Leu Tyr Ser Ala Asn Phe Glu Ser Leu Ile Pro Ala Asn Ala Asp
     50                  55                  60

Pro Val Val Thr Thr Gln Asn Ile Ile Val Thr Gly Gln Gly Glu Val
 65                  70                  75                  80

Val Ile Pro Gly Gly Val Tyr Asp Tyr Cys Ile Thr Asn Pro Glu Pro
                 85                  90                  95

Ala Ser Gly Lys Met Trp Ile Ala Gly Asp Gly Asn Gln Pro Ala
                100                 105                 110

Arg Tyr Asp Asp Phe Thr Phe Glu Ala Gly Lys Lys Tyr Thr Phe Thr
                115                 120                 125

Met Arg Arg Ala Gly Met Gly Asp Gly Thr Asp Met Glu Val Glu Asp
    130                 135                 140

Asp Ser Pro Ala Ser Tyr Thr Tyr Thr Val Tyr Arg Asp Gly Thr Lys
145                 150                 155                 160

Ile Lys Glu Gly Leu Thr Glu Thr Thr Tyr Arg Asp Ala Gly Met Ser
                165                 170                 175

Ala Gln Ser His Glu Tyr Cys Val Glu Val Lys Tyr Thr Ala Gly Val
                180                 185                 190

Ser Pro Lys Val Cys Val Asp Tyr Ile Pro Asp Gly Val Ala Asp Val
            195                 200                 205

Thr Ala Gln Lys Pro Tyr Thr Leu Thr Val Val Gly Lys Thr Ile Thr
    210                 215                 220

Val Thr Cys Gln Gly Glu Ala Met Ile Tyr Asp Met Asn Gly Arg Arg
225                 230                 235                 240

Leu Ala Ala Gly Arg Asn Thr Val Val Tyr Thr Ala Gln Gly Gly Tyr
                245                 250                 255

Tyr Ala Val Met Val Val Val Asp Gly Lys Ser Tyr Val Glu Lys Leu
                260                 265                 270

Ala Ile Lys
    275

<210> SEQ ID NO 47
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gaccatggct catcaccatc accatcacaa taccggagtc agctttgca                49

<210> SEQ ID NO 48
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gactcgagtt atttgtcctt attagtgagt gctttc                              36

<210> SEQ ID NO 49
<211> LENGTH: 31
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 49
gaccatggct tggggagaca atacgggtta c                                          31

<210> SEQ ID NO 50
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gactcgagac ctccgttagg caaatcc                                               27

<210> SEQ ID NO 51
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ccgtattgtc tccccatttg tccttattag tgagtgcttt c                               41

<210> SEQ ID NO 52
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
cactaataag gacaaatggg gagacaatac gggttac                                    37

<210> SEQ ID NO 53
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
catggatctg agaccgcatg ggctgatcca cttttcttgt tggatgccga t                    51

<210> SEQ ID NO 54
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ccatggcttt gaataccgga gtcagctttg caaactatac agcgcatgga tctgagaccg           60
ca                                                                          62

<210> SEQ ID NO 55
<211> LENGTH: 25
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 55
ctcgaggaat gattcggaaa gtgtt                                          25

<210> SEQ ID NO 56
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ccatggctga ttatagctgg aattcccagg tagtcagctt tgcaaactat aca           53

<210> SEQ ID NO 57
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
ctttgcaaac tatacagcgc atggatctga daccgcatgg gctgatccac tt            52

<210> SEQ ID NO 58
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
atgggctgat ccacttctga attcttattg gggcgagatc ggcaatatta cc            52

<210> SEQ ID NO 59
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gatcggcaat attacccata ttggtgctca ttacgcttgg ggagacaata cg            52

<210> SEQ ID NO 60
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ctcgagacct ccgttaggca aatccaatgc cggtgttatc agatagttgt ca            52

<210> SEQ ID NO 61
<211> LENGTH: 1706
<212> TYPE: PRT
<213> ORGANISM: Porphyromonas gingivalis

<400> SEQUENCE: 61

-continued

```
Met Lys Asn Leu Asn Lys Phe Val Ser Ile Ala Leu Cys Ser Ser Leu
1               5                   10                  15

Leu Gly Gly Met Ala Phe Ala Gln Gln Thr Glu Leu Gly Arg Asn Pro
            20                  25                  30

Asn Val Arg Leu Leu Glu Ser Thr Gln Gln Ser Val Thr Lys Val Gln
            35                  40                  45

Phe Arg Met Asp Asn Leu Lys Phe Thr Glu Val Gln Thr Pro Lys Gly
50                  55                  60

Ile Gly Gln Val Pro Thr Tyr Thr Glu Gly Val Asn Leu Ser Glu Lys
65                  70                  75                  80

Gly Met Pro Thr Leu Pro Ile Leu Ser Arg Ser Leu Ala Val Ser Asp
                85                  90                  95

Thr Arg Glu Met Lys Val Glu Val Val Ser Ser Lys Phe Ile Glu Lys
                100                 105                 110

Lys Asn Val Leu Ile Ala Pro Ser Lys Gly Met Ile Met Arg Asn Glu
            115                 120                 125

Asp Pro Lys Lys Ile Pro Tyr Val Tyr Gly Lys Thr Tyr Ser Gln Asn
    130                 135                 140

Lys Phe Phe Pro Gly Glu Ile Ala Thr Leu Asp Asp Pro Phe Ile Leu
145                 150                 155                 160

Arg Asp Val Arg Gly Gln Val Val Asn Phe Ala Pro Leu Gln Tyr Asn
                165                 170                 175

Pro Val Thr Lys Thr Leu Arg Ile Tyr Thr Glu Ile Thr Val Ala Val
                180                 185                 190

Ser Glu Thr Ser Glu Gln Gly Lys Asn Ile Leu Asn Lys Lys Gly Thr
            195                 200                 205

Phe Ala Gly Phe Glu Asp Thr Tyr Lys Arg Met Phe Met Asn Tyr Glu
            210                 215                 220

Pro Gly Arg Tyr Thr Pro Val Glu Glu Lys Gln Asn Gly Arg Met Ile
225                 230                 235                 240

Val Ile Val Ala Lys Lys Tyr Glu Gly Asp Ile Lys Asp Phe Val Asp
                245                 250                 255

Trp Lys Asn Gln Arg Gly Leu Arg Thr Glu Val Lys Val Ala Glu Asp
                260                 265                 270

Ile Ala Ser Pro Val Thr Ala Asn Ala Ile Gln Gln Phe Val Lys Gln
            275                 280                 285

Glu Tyr Glu Lys Glu Gly Asn Asp Leu Thr Tyr Val Leu Leu Ile Gly
    290                 295                 300

Asp His Lys Asp Ile Pro Ala Lys Ile Thr Pro Gly Ile Lys Ser Asp
305                 310                 315                 320

Gln Val Tyr Gly Gln Ile Val Gly Asn Asp His Tyr Asn Glu Val Phe
                325                 330                 335

Ile Gly Arg Phe Ser Cys Glu Ser Lys Glu Asp Leu Lys Thr Gln Ile
                340                 345                 350

Asp Arg Thr Ile His Tyr Glu Arg Asn Ile Thr Thr Glu Asp Lys Trp
            355                 360                 365

Leu Gly Gln Ala Leu Cys Ile Ala Ser Ala Glu Gly Pro Ser Ala
    370                 375                 380

Asp Asn Gly Glu Ser Asp Ile Gln His Glu Asn Val Ile Ala Asn Leu
385                 390                 395                 400

Leu Thr Gln Tyr Gly Tyr Thr Lys Ile Ile Lys Cys Tyr Asp Pro Gly
                405                 410                 415
```

-continued

Val Thr Pro Lys Asn Ile Ile Asp Ala Phe Asn Gly Gly Ile Ser Leu
            420                 425                 430

Ala Asn Tyr Thr Gly His Gly Ser Glu Thr Ala Trp Gly Thr Ser His
        435                 440                 445

Phe Gly Thr Thr His Val Lys Gln Leu Thr Asn Ser Asn Gln Leu Pro
    450                 455                 460

Phe Ile Phe Asp Val Ala Cys Val Asn Gly Asp Phe Leu Phe Ser Met
465                 470                 475                 480

Pro Cys Phe Ala Glu Ala Leu Met Arg Ala Gln Lys Asp Gly Lys Pro
                485                 490                 495

Thr Gly Thr Val Ala Ile Ile Ala Ser Thr Ile Asn Gln Ser Trp Ala
            500                 505                 510

Ser Pro Met Arg Gly Gln Asp Glu Met Asn Glu Ile Leu Cys Glu Lys
        515                 520                 525

His Pro Asn Asn Ile Lys Arg Thr Phe Gly Val Thr Met Asn Gly
    530                 535                 540

Met Phe Ala Met Val Glu Lys Tyr Lys Lys Asp Gly Glu Lys Met Leu
545                 550                 555                 560

Asp Thr Trp Thr Val Phe Gly Asp Pro Ser Leu Leu Val Arg Thr Leu
                565                 570                 575

Val Pro Thr Lys Met Gln Val Thr Ala Pro Ala Gln Ile Asn Leu Thr
            580                 585                 590

Asp Ala Ser Val Asn Val Ser Cys Asp Tyr Asn Gly Ala Ile Ala Thr
        595                 600                 605

Ile Ser Ala Asn Gly Lys Met Phe Gly Ser Ala Val Val Glu Asn Gly
610                 615                 620

Thr Ala Thr Ile Asn Leu Thr Gly Leu Thr Asn Glu Ser Thr Leu Thr
625                 630                 635                 640

Leu Thr Val Val Gly Tyr Asn Lys Glu Thr Val Ile Lys Thr Ile Asn
            645                 650                 655

Thr Asn Gly Glu Pro Asn Pro Tyr Gln Pro Val Ser Asn Leu Thr Ala
        660                 665                 670

Thr Thr Gln Gly Gln Lys Val Thr Leu Lys Trp Asp Ala Pro Ser Thr
    675                 680                 685

Lys Thr Asn Ala Thr Thr Asn Thr Ala Arg Ser Val Asp Gly Ile Arg
690                 695                 700

Glu Leu Val Leu Leu Ser Val Ser Asp Ala Pro Glu Leu Leu Arg Ser
705                 710                 715                 720

Gly Gln Ala Glu Ile Val Leu Glu Ala His Asp Val Trp Asn Asp Gly
            725                 730                 735

Ser Gly Tyr Gln Ile Leu Leu Asp Ala Asp His Asp Gln Tyr Gly Gln
        740                 745                 750

Val Ile Pro Ser Asp Thr His Thr Leu Trp Pro Asn Cys Ser Val Pro
    755                 760                 765

Ala Asn Leu Phe Ala Pro Phe Glu Tyr Thr Val Pro Glu Asn Ala Asp
770                 775                 780

Pro Ser Cys Ser Pro Thr Asn Met Ile Met Asp Gly Thr Ala Ser Val
785                 790                 795                 800

Asn Ile Pro Ala Gly Thr Tyr Asp Phe Ala Ile Ala Pro Gln Ala
            805                 810                 815

Asn Ala Lys Ile Trp Ile Ala Gly Gln Gly Pro Thr Lys Glu Asp Asp
        820                 825                 830

Tyr Val Phe Glu Ala Gly Lys Lys Tyr His Phe Leu Met Lys Lys Met

```
                835                 840                 845
Gly Ser Gly Asp Gly Thr Glu Leu Thr Ile Ser Glu Gly Gly Gly Ser
850                 855                 860

Asp Tyr Thr Tyr Thr Val Tyr Arg Asp Gly Thr Lys Ile Lys Glu Gly
865                 870                 875                 880

Leu Thr Ala Thr Thr Phe Glu Asp Gly Val Ala Thr Gly Asn His
                    885                 890                 895

Glu Tyr Cys Val Glu Val Lys Tyr Thr Ala Gly Val Ser Pro Lys Val
                900                 905                 910

Cys Lys Asp Val Thr Val Glu Gly Ser Asn Glu Phe Ala Pro Val Gln
                915                 920                 925

Asn Leu Thr Gly Ser Ala Val Gly Gln Lys Val Thr Leu Lys Trp Asp
930                 935                 940

Ala Pro Asn Gly Thr Pro Asn Pro Asn Pro Asn Pro Asn Pro Asn Pro
945                 950                 955                 960

Asn Pro Gly Thr Thr Thr Leu Ser Glu Ser Phe Glu Asn Gly Ile Pro
                965                 970                 975

Ala Ser Trp Lys Thr Ile Asp Ala Asp Gly Asp Gly His Gly Trp Lys
                980                 985                 990

Pro Gly Asn Ala Pro Gly Ile Ala  Gly Tyr Asn Ser Asn  Gly Cys Val
                995                 1000                1005

Tyr Ser Glu Ser Phe Gly Leu  Gly Gly Ile Gly Val  Leu Thr Pro
1010                1015                1020

Asp Asn  Tyr Leu Ile Thr Pro  Ala Leu Asp Leu Pro  Asn Gly Gly
1025                1030                1035

Lys Leu Thr Phe Trp Val Cys  Ala Gln Asp Ala Asn  Tyr Ala Ser
1040                1045                1050

Glu His  Tyr Ala Val Tyr Ala  Ser Ser Thr Gly Asn  Asp Ala Ser
1055                1060                1065

Asn Phe  Thr Asn Ala Leu Leu  Glu Glu Thr Ile Thr  Ala Lys Gly
1070                1075                1080

Val Arg  Ser Pro Glu Ala Met  Arg Gly Arg Ile Gln  Gly Thr Trp
1085                1090                1095

Arg Gln  Lys Thr Val Asp Leu  Pro Ala Gly Thr Lys  Tyr Val Ala
1100                1105                1110

Phe Arg  His Phe Gln Ser Thr  Asp Met Phe Tyr Ile  Asp Leu Asp
1115                1120                1125

Glu Val  Glu Ile Lys Ala Asn  Gly Lys Arg Ala Asp  Phe Thr Glu
1130                1135                1140

Thr Phe  Glu Ser Ser Thr His  Gly Glu Ala Pro Ala  Glu Trp Thr
1145                1150                1155

Thr Ile  Asp Ala Asp Gly Asp  Gly Gln Gly Trp Leu  Cys Leu Ser
1160                1165                1170

Ser Gly  Gln Leu Asp Trp Leu  Thr Ala His Gly Gly  Thr Asn Val
1175                1180                1185

Val Ser  Ser Phe Ser Trp Asn  Gly Met Ala Leu Asn  Pro Asp Asn
1190                1195                1200

Tyr Leu  Ile Ser Lys Asp Val  Thr Gly Ala Thr Lys  Val Lys Tyr
1205                1210                1215

Tyr Tyr  Ala Val Asn Asp Gly  Phe Pro Gly Asp His  Tyr Ala Val
1220                1225                1230

Met Ile  Ser Lys Thr Gly Thr  Asn Ala Gly Asp Phe  Thr Val Val
1235                1240                1245
```

```
Phe Glu Glu Thr Pro Asn Gly Ile Asn Lys Gly Gly Ala Arg Phe
    1250                1255                1260

Gly Leu Ser Thr Glu Ala Asp Gly Ala Lys Pro Gln Ser Val Trp
    1265                1270                1275

Ile Glu Arg Thr Val Asp Leu Pro Ala Gly Thr Lys Tyr Val Ala
    1280                1285                1290

Phe Arg His Tyr Asn Cys Ser Asp Leu Asn Tyr Ile Leu Leu Asp
    1295                1300                1305

Asp Ile Gln Phe Thr Met Gly Gly Ser Pro Thr Pro Thr Asp Tyr
    1310                1315                1320

Thr Tyr Thr Val Tyr Arg Asp Gly Thr Lys Ile Lys Glu Gly Leu
    1325                1330                1335

Thr Glu Thr Thr Phe Glu Glu Asp Gly Val Ala Thr Gly Asn His
    1340                1345                1350

Glu Tyr Cys Val Glu Val Lys Tyr Thr Ala Gly Val Ser Pro Lys
    1355                1360                1365

Lys Cys Val Asn Val Thr Val Asn Ser Thr Gln Phe Asn Pro Val
    1370                1375                1380

Lys Asn Leu Lys Ala Gln Pro Asp Gly Asp Val Val Leu Lys
    1385                1390                1395

Trp Glu Ala Pro Ser Ala Lys Lys Thr Glu Gly Ser Arg Glu Val
    1400                1405                1410

Lys Arg Ile Gly Asp Gly Leu Phe Val Thr Ile Glu Pro Ala Asn
    1415                1420                1425

Asp Val Arg Ala Asn Glu Ala Lys Val Val Leu Ala Ala Asp Asn
    1430                1435                1440

Val Trp Gly Asp Asn Thr Gly Tyr Gln Phe Leu Leu Asp Ala Asp
    1445                1450                1455

His Asn Thr Phe Gly Ser Val Ile Pro Ala Thr Gly Pro Leu Phe
    1460                1465                1470

Thr Gly Thr Ala Ser Ser Asp Leu Tyr Ser Ala Asn Phe Glu Ser
    1475                1480                1485

Leu Ile Pro Ala Asn Ala Asp Pro Val Val Thr Thr Gln Asn Ile
    1490                1495                1500

Ile Val Thr Gly Gln Gly Glu Val Val Ile Pro Gly Gly Val Tyr
    1505                1510                1515

Asp Tyr Cys Ile Thr Asn Pro Glu Pro Ala Ser Gly Lys Met Trp
    1520                1525                1530

Ile Ala Gly Asp Gly Gly Asn Gln Pro Ala Arg Tyr Asp Asp Phe
    1535                1540                1545

Thr Phe Glu Ala Gly Lys Lys Tyr Thr Phe Thr Met Arg Arg Ala
    1550                1555                1560

Gly Met Gly Asp Gly Thr Asp Met Glu Val Glu Asp Asp Ser Pro
    1565                1570                1575

Ala Ser Tyr Thr Tyr Thr Val Tyr Arg Asp Gly Thr Lys Ile Lys
    1580                1585                1590

Glu Gly Leu Thr Glu Thr Thr Tyr Arg Asp Ala Gly Met Ser Ala
    1595                1600                1605

Gln Ser His Glu Tyr Cys Val Glu Val Lys Tyr Thr Ala Gly Val
    1610                1615                1620

Ser Pro Lys Val Cys Val Asp Tyr Ile Pro Asp Gly Val Ala Asp
    1625                1630                1635
```

```
Val Thr Ala Gln Lys Pro Tyr Thr Leu Thr Val Gly Lys Thr
    1640                1645                1650

Ile Thr Val Thr Cys Gln Gly Glu Ala Met Ile Tyr Asp Met Asn
    1655                1660                1665

Gly Arg Arg Leu Ala Ala Gly Arg Asn Thr Val Val Tyr Thr Ala
    1670                1675                1680

Gln Gly Gly Tyr Tyr Ala Val Met Val Val Val Asp Gly Lys Ser
    1685                1690                1695

Tyr Val Glu Lys Leu Ala Ile Lys
    1700                1705

<210> SEQ ID NO 62
<211> LENGTH: 1732
<212> TYPE: PRT
<213> ORGANISM: Porphyromonas gingivalis

<400> SEQUENCE: 62

Met Arg Lys Leu Leu Leu Ile Ala Ala Ser Leu Leu Gly Val Gly
1               5                   10                  15

Leu Tyr Ala Gln Ser Ala Lys Ile Lys Leu Asp Ala Pro Thr Thr Arg
                20                  25                  30

Thr Thr Cys Thr Asn Asn Ser Phe Lys Gln Phe Asp Ala Ser Phe Ser
            35                  40                  45

Phe Asn Glu Val Glu Leu Thr Lys Val Glu Thr Lys Gly Gly Thr Phe
50                  55                  60

Ala Ser Val Ser Ile Pro Gly Ala Phe Pro Thr Gly Glu Val Gly Ser
65                  70                  75                  80

Pro Glu Val Pro Ala Val Arg Lys Leu Ile Ala Val Pro Val Gly Ala
                85                  90                  95

Thr Pro Val Val Arg Val Lys Ser Phe Thr Glu Gln Val Tyr Ser Leu
                100                 105                 110

Asn Gln Tyr Gly Ser Glu Lys Leu Met Pro His Gln Pro Ser Met Ser
                115                 120                 125

Lys Ser Asp Asp Pro Glu Lys Val Pro Phe Val Tyr Asn Ala Ala Ala
    130                 135                 140

Tyr Ala Arg Lys Gly Phe Val Gly Gln Glu Leu Thr Gln Val Glu Met
145                 150                 155                 160

Leu Gly Thr Met Arg Gly Val Arg Ile Ala Ala Leu Thr Ile Asn Pro
                165                 170                 175

Val Gln Tyr Asp Val Val Ala Asn Gln Leu Lys Val Arg Asn Asn Ile
                180                 185                 190

Glu Ile Glu Val Ser Phe Gln Gly Ala Asp Glu Val Ala Thr Gln Arg
                195                 200                 205

Leu Tyr Asp Ala Ser Phe Ser Pro Tyr Phe Glu Thr Ala Tyr Lys Gln
    210                 215                 220

Leu Phe Asn Arg Asp Val Tyr Thr Asp His Gly Asp Leu Tyr Asn Thr
225                 230                 235                 240

Pro Val Arg Met Leu Val Val Ala Gly Ala Lys Phe Lys Glu Ala Leu
                245                 250                 255

Lys Pro Trp Leu Thr Trp Lys Ala Gln Lys Gly Phe Tyr Leu Asp Val
                260                 265                 270

His Tyr Thr Asp Glu Ala Glu Val Gly Thr Thr Asn Ala Ser Ile Lys
        275                 280                 285

Ala Phe Ile His Lys Lys Tyr Asn Asp Gly Leu Ala Ala Ser Ala Ala
    290                 295                 300
```

```
Pro Val Phe Leu Ala Leu Val Gly Asp Thr Asp Val Ile Ser Gly Glu
305                 310                 315                 320

Lys Gly Lys Lys Thr Lys Lys Val Thr Asp Leu Tyr Tyr Ser Ala Val
            325                 330                 335

Asp Gly Asp Tyr Phe Pro Glu Met Tyr Thr Phe Arg Met Ser Ala Ser
            340                 345                 350

Ser Pro Glu Glu Leu Thr Asn Ile Ile Asp Lys Val Leu Met Tyr Glu
            355                 360                 365

Lys Ala Thr Met Pro Asp Lys Ser Tyr Leu Glu Lys Val Leu Leu Ile
            370                 375                 380

Ala Gly Ala Asp Tyr Ser Trp Asn Ser Gln Val Gly Gln Pro Thr Ile
385                 390                 395                 400

Lys Tyr Gly Met Gln Tyr Tyr Asn Gln Glu His Gly Tyr Thr Asp
            405                 410                 415

Val Tyr Asn Tyr Leu Lys Ala Pro Tyr Thr Gly Cys Tyr Ser His Leu
            420                 425                 430

Asn Thr Gly Val Ser Phe Ala Asn Tyr Thr Ala His Gly Ser Glu Thr
            435                 440                 445

Ala Trp Ala Asp Pro Leu Leu Thr Thr Ser Gln Leu Lys Ala Leu Thr
450                 455                 460

Asn Lys Asp Lys Tyr Phe Leu Ala Ile Gly Asn Cys Cys Ile Thr Ala
465                 470                 475                 480

Gln Phe Asp Tyr Val Gln Pro Cys Phe Gly Glu Val Ile Thr Arg Val
            485                 490                 495

Lys Glu Lys Gly Ala Tyr Ala Tyr Ile Gly Ser Ser Pro Asn Ser Tyr
            500                 505                 510

Trp Gly Glu Asp Tyr Tyr Trp Ser Val Gly Ala Asn Ala Val Phe Gly
            515                 520                 525

Val Gln Pro Thr Phe Glu Gly Thr Ser Met Gly Ser Tyr Asp Ala Thr
            530                 535                 540

Phe Leu Glu Asp Ser Tyr Asn Thr Val Asn Ser Ile Met Trp Ala Gly
545                 550                 555                 560

Asn Leu Ala Ala Thr His Ala Gly Asn Ile Gly Asn Ile Thr His Ile
            565                 570                 575

Gly Ala His Tyr Tyr Trp Glu Ala Tyr His Val Leu Gly Asp Gly Ser
            580                 585                 590

Val Met Pro Tyr Arg Ala Met Pro Lys Thr Asn Thr Tyr Thr Leu Pro
            595                 600                 605

Ala Ser Leu Pro Gln Asn Gln Ala Ser Tyr Ser Ile Gln Ala Ser Ala
            610                 615                 620

Gly Ser Tyr Val Ala Ile Ser Lys Asp Gly Val Leu Tyr Gly Thr Gly
625                 630                 635                 640

Val Ala Asn Ala Ser Gly Val Ala Thr Val Ser Met Thr Lys Gln Ile
            645                 650                 655

Thr Glu Asn Gly Asn Tyr Asp Val Val Ile Thr Arg Ser Asn Tyr Leu
            660                 665                 670

Pro Val Ile Lys Gln Ile Gln Val Gly Glu Pro Ser Pro Tyr Gln Pro
            675                 680                 685

Val Ser Asn Leu Thr Ala Thr Thr Gln Gly Gln Lys Val Thr Leu Lys
            690                 695                 700

Trp Glu Ala Pro Ser Ala Lys Lys Ala Glu Gly Ser Arg Glu Val Lys
705                 710                 715                 720
```

-continued

```
Arg Ile Gly Asp Gly Leu Phe Val Thr Ile Glu Pro Ala Asn Asp Val
            725                 730                 735

Arg Ala Asn Glu Ala Lys Val Val Leu Ala Ala Asp Asn Val Trp Gly
            740                 745                 750

Asp Asn Thr Gly Tyr Gln Phe Leu Leu Asp Ala Asp His Asn Thr Phe
            755                 760                 765

Gly Ser Val Ile Pro Ala Thr Gly Pro Leu Phe Thr Gly Thr Ala Ser
            770                 775                 780

Ser Asn Leu Tyr Ser Ala Asn Phe Glu Tyr Leu Ile Pro Ala Asn Ala
785                 790                 795                 800

Asp Pro Val Val Thr Thr Gln Asn Ile Ile Val Thr Gly Gln Gly Glu
                805                 810                 815

Val Val Ile Pro Gly Gly Val Tyr Asp Tyr Cys Ile Thr Asn Pro Glu
                820                 825                 830

Pro Ala Ser Gly Lys Met Trp Ile Ala Gly Asp Gly Gly Asn Gln Pro
                835                 840                 845

Ala Arg Tyr Asp Asp Phe Thr Phe Glu Ala Gly Lys Lys Tyr Thr Phe
            850                 855                 860

Thr Met Arg Arg Ala Gly Met Gly Asp Gly Thr Asp Met Glu Val Glu
865                 870                 875                 880

Asp Asp Ser Pro Ala Ser Tyr Thr Tyr Thr Val Tyr Arg Asp Gly Thr
                885                 890                 895

Lys Ile Lys Glu Gly Leu Thr Ala Thr Thr Phe Glu Glu Asp Gly Val
            900                 905                 910

Ala Ala Gly Asn His Glu Tyr Cys Val Glu Val Lys Tyr Thr Ala Gly
            915                 920                 925

Val Ser Pro Lys Val Cys Lys Asp Val Thr Val Glu Gly Ser Asn Glu
930                 935                 940

Phe Ala Pro Val Gln Asn Leu Thr Gly Ser Ser Val Gly Gln Lys Val
945                 950                 955                 960

Thr Leu Lys Trp Asp Ala Pro Asn Gly Thr Pro Asn Pro Asn Pro Asn
                965                 970                 975

Pro Asn Pro Asn Pro Gly Thr Thr Leu Ser Glu Ser Phe Glu Asn Gly
                980                 985                 990

Ile Pro Ala Ser Trp Lys Thr Ile Asp Ala Asp Gly Asp Gly His Gly
            995                1000                1005

Trp Lys Pro Gly Asn Ala Pro Gly Ile Ala Gly Tyr Asn Ser Asn
           1010                1015                1020

Gly Cys Val Tyr Ser Glu Ser Phe Gly Leu Gly Gly Ile Gly Val
           1025                1030                1035

Leu Thr Pro Asp Asn Tyr Leu Ile Thr Pro Ala Leu Asp Leu Pro
           1040                1045                1050

Asn Gly Gly Lys Leu Thr Phe Trp Val Cys Ala Gln Asp Ala Asn
           1055                1060                1065

Tyr Ala Ser Glu His Tyr Ala Val Tyr Ala Ser Ser Thr Gly Asn
           1070                1075                1080

Asp Ala Ser Asn Phe Thr Asn Ala Leu Leu Glu Glu Thr Ile Thr
           1085                1090                1095

Ala Lys Gly Val Arg Ser Pro Lys Ala Ile Arg Gly Arg Ile Gln
           1100                1105                1110

Gly Thr Trp Arg Gln Lys Val Asp Leu Pro Ala Gly Thr Lys
           1115                1120                1125

Tyr Val Ala Phe Arg His Phe Gln Ser Thr Asp Met Phe Tyr Ile
```

```
                1130                1135                1140
Asp Leu Asp Glu Val Glu Ile Lys Ala Asn Gly Lys Arg Ala Asp
    1145                1150                1155

Phe Thr Glu Thr Phe Glu Ser Ser Thr His Gly Glu Ala Pro Ala
    1160                1165                1170

Glu Trp Thr Thr Ile Asp Ala Asp Gly Asp Gly Gln Gly Trp Leu
    1175                1180                1185

Cys Leu Ser Ser Gly Gln Leu Asp Trp Leu Thr Ala His Gly Gly
    1190                1195                1200

Ser Asn Val Val Ser Ser Phe Ser Trp Asn Gly Met Ala Leu Asn
    1205                1210                1215

Pro Asp Asn Tyr Leu Ile Ser Lys Asp Val Thr Gly Ala Thr Lys
    1220                1225                1230

Val Lys Tyr Tyr Tyr Ala Val Asn Asp Gly Phe Pro Gly Asp His
    1235                1240                1245

Tyr Ala Val Met Ile Ser Lys Thr Gly Thr Asn Ala Gly Asp Phe
    1250                1255                1260

Thr Val Val Phe Glu Glu Thr Pro Asn Gly Ile Asn Lys Gly Gly
    1265                1270                1275

Ala Arg Phe Gly Leu Ser Thr Glu Ala Asn Gly Ala Lys Pro Gln
    1280                1285                1290

Ser Val Trp Ile Glu Arg Thr Val Asp Leu Pro Ala Gly Thr Lys
    1295                1300                1305

Tyr Val Ala Phe Arg His Tyr Asn Cys Ser Asp Leu Asn Tyr Ile
    1310                1315                1320

Leu Leu Asp Asp Ile Gln Phe Thr Met Gly Gly Ser Pro Thr Pro
    1325                1330                1335

Thr Asp Tyr Thr Tyr Thr Val Tyr Arg Asp Gly Thr Lys Ile Lys
    1340                1345                1350

Glu Gly Leu Thr Glu Thr Thr Phe Glu Glu Asp Gly Val Ala Thr
    1355                1360                1365

Gly Asn His Glu Tyr Cys Val Glu Val Lys Tyr Thr Ala Gly Val
    1370                1375                1380

Ser Pro Lys Lys Cys Val Asn Val Thr Val Asn Ser Thr Gln Phe
    1385                1390                1395

Asn Pro Val Gln Asn Leu Thr Ala Glu Gln Ala Pro Asn Ser Met
    1400                1405                1410

Asp Ala Ile Leu Lys Trp Asn Ala Pro Ala Ser Lys Arg Ala Glu
    1415                1420                1425

Val Leu Asn Glu Asp Phe Glu Asn Gly Ile Pro Ala Ser Trp Lys
    1430                1435                1440

Thr Ile Asp Ala Asp Gly Asp Gly Asn Asn Trp Thr Thr Thr Pro
    1445                1450                1455

Pro Pro Gly Gly Ser Ser Phe Ala Gly His Asn Ser Ala Ile Cys
    1460                1465                1470

Val Ser Ser Ala Ser Tyr Ile Asn Phe Glu Gly Pro Gln Asn Pro
    1475                1480                1485

Asp Asn Tyr Leu Val Thr Pro Glu Leu Ser Leu Pro Gly Gly Gly
    1490                1495                1500

Thr Leu Thr Phe Trp Val Cys Ala Gln Asp Ala Asn Tyr Ala Ser
    1505                1510                1515

Glu His Tyr Ala Val Tyr Ala Ser Ser Thr Gly Asn Asp Ala Ser
    1520                1525                1530
```

-continued

Asn Phe Ala Asn Ala Leu Leu Glu Glu Val Leu Thr Ala Lys Thr
          1535                1540                1545

Val Val Thr Ala Pro Glu Ala Ile Arg Gly Thr Arg Ala Gln Gly
    1550                1555                1560

Thr Trp Tyr Gln Lys Thr Val Gln Leu Pro Ala Gly Thr Lys Tyr
    1565                1570                1575

Val Ala Phe Arg His Phe Gly Cys Thr Asp Phe Phe Trp Ile Asn
    1580                1585                1590

Leu Asp Asp Val Val Ile Thr Ser Gly Asn Ala Pro Ser Tyr Thr
    1595                1600                1605

Tyr Thr Ile Tyr Arg Asn Asn Thr Gln Ile Ala Ser Gly Val Thr
    1610                1615                1620

Glu Thr Thr Tyr Arg Asp Pro Asp Leu Ala Thr Gly Phe Tyr Thr
    1625                1630                1635

Tyr Gly Val Lys Val Val Tyr Pro Asn Gly Glu Ser Ala Ile Glu
    1640                1645                1650

Thr Ala Thr Leu Asn Ile Thr Ser Leu Ala Asp Val Thr Ala Gln
    1655                1660                1665

Lys Pro Tyr Thr Leu Thr Val Val Gly Lys Thr Ile Thr Val Thr
    1670                1675                1680

Cys Gln Gly Glu Ala Met Ile Tyr Asp Met Asn Gly Arg Arg Leu
    1685                1690                1695

Ala Ala Gly Arg Asn Thr Val Val Tyr Thr Ala Gln Gly Gly His
    1700                1705                1710

Tyr Ala Val Met Val Val Val Asp Gly Lys Ser Tyr Val Glu Lys
    1715                1720                1725

Leu Ala Val Lys
    1730

<210> SEQ ID NO 63
<211> LENGTH: 2164
<212> TYPE: PRT
<213> ORGANISM: Porphyromonas gingivalis

<400> SEQUENCE: 63

Met Arg Lys Leu Asn Ser Leu Phe Ser Leu Ala Val Leu Ser Leu
1               5                   10                  15

Leu Cys Trp Gly Gln Thr Ala Ala Gln Gly Gly Pro Lys Thr Ala
            20                  25                  30

Pro Ser Val Thr His Gln Ala Val Gln Lys Gly Ile Arg Thr Ser Lys
            35                  40                  45

Ala Lys Asp Leu Arg Asp Pro Ile Pro Ala Gly Met Ala Arg Ile Ile
    50                  55                  60

Leu Glu Ala His Asp Val Trp Glu Asp Gly Thr Gly Tyr Gln Met Leu
65                  70                  75                  80

Trp Asp Ala Asp His Asn Gln Tyr Gly Ala Ser Ile Pro Glu Glu Ser
                85                  90                  95

Phe Trp Phe Ala Asn Gly Thr Ile Pro Ala Gly Leu Tyr Asp Pro Phe
            100                 105                 110

Glu Tyr Lys Val Pro Val Asn Ala Asp Ala Ser Phe Ser Pro Thr Asn
            115                 120                 125

Phe Val Leu Asp Gly Thr Ala Ser Ala Asp Ile Pro Ala Gly Thr Tyr
        130                 135                 140

Asp Tyr Val Ile Ile Asn Pro Asn Pro Gly Ile Ile Tyr Ile Val Gly

```
                145                 150                 155                 160
        Glu Gly Val Ser Lys Gly Asn Asp Tyr Val Glu Ala Gly Lys Thr
                            165                 170                 175

Tyr His Phe Thr Val Gln Arg Gln Gly Pro Gly Asp Ala Ala Ser Val
                            180                 185                 190

Val Val Thr Gly Glu Gly Gly Asn Glu Phe Ala Pro Val Gln Asn Leu
                            195                 200                 205

Gln Trp Ser Val Ser Gly Gln Thr Val Thr Leu Thr Trp Gln Ala Pro
        210                 215                 220

Ala Ser Asp Lys Arg Thr Tyr Val Leu Asn Glu Ser Phe Asp Thr Gln
        225                 230                 235                 240

Thr Leu Pro Asn Gly Trp Thr Met Ile Asp Ala Asp Gly Asp Gly His
                            245                 250                 255

Asn Trp Leu Ser Thr Ile Asn Val Tyr Asn Thr Ala Thr His Thr Gly
                            260                 265                 270

Asp Gly Ala Met Phe Ser Lys Ser Trp Thr Ala Ser Ser Gly Ala Lys
                            275                 280                 285

Ile Asp Leu Ser Pro Asp Asn Tyr Leu Val Thr Pro Lys Phe Thr Val
        290                 295                 300

Pro Glu Asn Gly Lys Leu Ser Tyr Trp Val Ser Ser Gln Glu Pro Trp
        305                 310                 315                 320

Thr Asn Glu His Tyr Gly Val Phe Leu Ser Thr Thr Gly Asn Glu Ala
                            325                 330                 335

Ala Asn Phe Thr Ile Lys Leu Leu Glu Glu Thr Leu Gly Ser Gly Lys
                            340                 345                 350

Pro Ala Pro Met Asn Leu Val Lys Ser Glu Gly Val Lys Ala Pro Ala
                            355                 360                 365

Pro Tyr Gln Glu Arg Thr Ile Asp Leu Ser Ala Tyr Ala Gly Gln Gln
                            370                 375                 380

Val Tyr Leu Ala Phe Arg His Phe Gly Cys Thr Gly Ile Phe Arg Leu
        385                 390                 395                 400

Tyr Leu Asp Asp Val Ala Val Ser Gly Glu Gly Ser Ser Asn Asp Tyr
                            405                 410                 415

Thr Tyr Thr Val Tyr Arg Asp Asn Val Val Ile Ala Gln Asn Leu Thr
                            420                 425                 430

Ala Thr Thr Phe Asn Gln Glu Asn Val Ala Pro Gly Gln Tyr Asn Tyr
                            435                 440                 445

Cys Val Glu Val Lys Tyr Thr Ala Gly Val Ser Pro Lys Val Cys Lys
        450                 455                 460

Asp Val Thr Val Glu Gly Ser Asn Glu Phe Ala Pro Val Gln Asn Leu
        465                 470                 475                 480

Thr Gly Ser Ala Val Gly Gln Lys Val Thr Leu Lys Trp Asp Ala Pro
                            485                 490                 495

Asn Gly Thr Pro Asn Pro Asn Pro Gly Thr Thr Thr Leu Ser Glu Ser
                            500                 505                 510

Phe Glu Asn Gly Ile Pro Ala Ser Trp Lys Thr Ile Asp Ala Asp Gly
                            515                 520                 525

Asp Gly Asn Asn Trp Thr Thr Thr Pro Pro Gly Gly Ser Ser Phe
                            530                 535                 540

Ala Gly His Asn Ser Ala Ile Cys Val Ser Ser Ala Ser Tyr Ile Asn
        545                 550                 555                 560

Phe Glu Gly Pro Gln Asn Pro Asp Asn Tyr Leu Val Thr Pro Glu Leu
                            565                 570                 575
```

```
Ser Leu Pro Asn Gly Gly Thr Leu Thr Phe Trp Val Cys Ala Gln Asp
            580                 585                 590

Ala Asn Tyr Ala Ser Glu His Tyr Ala Val Tyr Ala Ser Ser Thr Gly
            595                 600                 605

Asn Asp Ala Ser Asn Phe Ala Asn Ala Leu Leu Glu Glu Val Leu Thr
            610                 615                 620

Ala Lys Thr Val Val Thr Ala Pro Glu Ala Ile Arg Gly Thr Arg Val
625                 630                 635                 640

Gln Gly Thr Trp Tyr Gln Lys Thr Val Gln Leu Pro Ala Gly Thr Lys
                645                 650                 655

Tyr Val Ala Phe Arg His Phe Gly Cys Thr Asp Phe Phe Trp Ile Asn
            660                 665                 670

Leu Asp Asp Val Glu Ile Lys Ala Asn Gly Lys Arg Ala Asp Phe Thr
            675                 680                 685

Glu Thr Phe Glu Ser Ser Thr His Gly Glu Ala Pro Ala Glu Trp Thr
            690                 695                 700

Thr Ile Asp Ala Asp Gly Asp Gly Gln Gly Trp Leu Cys Leu Ser Ser
705                 710                 715                 720

Gly Gln Leu Gly Trp Leu Thr Ala His Gly Gly Thr Asn Val Val Ala
                725                 730                 735

Ser Phe Ser Trp Asn Gly Met Ala Leu Asn Pro Asp Asn Tyr Leu Ile
            740                 745                 750

Ser Lys Asp Val Thr Gly Ala Thr Lys Val Lys Tyr Tyr Tyr Ala Val
            755                 760                 765

Asn Asp Gly Phe Pro Gly Asp His Tyr Ala Val Met Ile Ser Lys Thr
            770                 775                 780

Gly Thr Asn Ala Gly Asp Phe Thr Val Val Phe Glu Glu Thr Pro Asn
785                 790                 795                 800

Gly Ile Asn Lys Gly Gly Ala Arg Phe Gly Leu Ser Thr Glu Ala Asn
                805                 810                 815

Gly Ala Lys Pro Gln Ser Val Trp Ile Glu Arg Thr Val Asp Leu Pro
            820                 825                 830

Ala Gly Thr Lys Tyr Val Ala Phe Arg His Tyr Asn Cys Ser Asp Leu
            835                 840                 845

Asn Tyr Ile Leu Leu Asp Asp Ile Gln Phe Thr Met Gly Gly Ser Pro
850                 855                 860

Thr Pro Thr Asp Tyr Thr Tyr Thr Val Tyr Arg Asp Gly Thr Lys Ile
865                 870                 875                 880

Lys Glu Gly Leu Thr Glu Thr Thr Phe Glu Glu Asp Gly Val Ala Thr
                885                 890                 895

Gly Asn His Glu Tyr Cys Val Gly Val Lys Tyr Thr Ala Gly Val Ser
            900                 905                 910

Pro Lys Glu Cys Val Asn Val Thr Val Asp Pro Val Gln Phe Asn Pro
            915                 920                 925

Val Gln Asn Leu Thr Gly Ser Ala Val Gly Gln Lys Val Thr Leu Lys
            930                 935                 940

Trp Asp Ala Pro Asn Gly Thr Pro Asn Pro Asn Pro Gly Thr Thr Thr
945                 950                 955                 960

Leu Ser Glu Ser Phe Glu Asn Gly Ile Pro Ala Ser Trp Lys Thr Ile
                965                 970                 975

Asp Ala Asp Gly Asp Gly Asn Asn Trp Thr Thr Thr Pro Pro Pro Gly
            980                 985                 990
```

```
        Gly Thr Ser Phe Ala Gly His Asn  Ser Ala Ile Cys  Val Ser Ser Ala
                    995                 1000                1005

Ser Tyr Ile Asn Phe Glu Gly  Pro Gln Asn Pro Asp  Asn Tyr Leu
            1010                1015                1020

Val Thr Pro Glu Leu Ser Leu  Pro Asn Gly Gly Thr  Leu Thr Phe
            1025                1030                1035

Trp Val Cys Ala Gln Asp Ala  Asn Tyr Ala Ser Glu  His Tyr Ala
            1040                1045                1050

Val Tyr Ala Ser Ser Thr Gly  Asn Asp Ala Ser Asn  Phe Ala Asn
            1055                1060                1065

Ala Leu Leu Glu Glu Val Leu  Thr Ala Lys Thr Val  Val Thr Ala
            1070                1075                1080

Pro Glu Ala Ile Arg Gly Thr  Arg Val Gln Gly Thr  Trp Tyr Gln
            1085                1090                1095

Lys Thr Val Gln Leu Pro Ala  Gly Thr Lys Tyr Val  Ala Phe Arg
            1100                1105                1110

His Phe Gly Cys Thr Asp Phe  Phe Trp Ile Asn Leu  Asp Asp Val
            1115                1120                1125

Glu Ile Lys Ala Asn Gly Lys  Arg Ala Asp Phe Thr  Glu Thr Phe
            1130                1135                1140

Glu Ser Ser Thr His Gly Glu  Ala Pro Ala Glu Trp  Thr Thr Ile
            1145                1150                1155

Asp Ala Asp Gly Asp Gly Gln  Gly Trp Leu Cys Leu  Ser Ser Gly
            1160                1165                1170

Gln Leu Asp Trp Leu Thr Ala  His Gly Gly Thr Asn  Val Val Ala
            1175                1180                1185

Ser Phe Ser Trp Asn Gly Met  Ala Leu Asn Pro Asp  Asn Tyr Leu
            1190                1195                1200

Ile Ser Lys Asp Val Thr Gly  Ala Thr Lys Val Lys  Tyr Tyr Tyr
            1205                1210                1215

Ala Val Asn Asp Gly Phe Pro  Gly Asp His Tyr Ala  Val Met Ile
            1220                1225                1230

Ser Lys Thr Gly Thr Asn Ala  Gly Asp Phe Thr Val  Val Phe Glu
            1235                1240                1245

Glu Thr Pro Asn Gly Ile Asn  Lys Gly Gly Ala Arg  Phe Gly Leu
            1250                1255                1260

Ser Thr Glu Ala Asn Gly Ala  Lys Pro Gln Ser Val  Trp Ile Glu
            1265                1270                1275

Arg Thr Val Asp Leu Pro Ala  Gly Thr Lys Tyr Val  Ala Phe Arg
            1280                1285                1290

His Tyr Asn Cys Ser Asp Leu  Asn Tyr Ile Leu Leu  Asp Asp Ile
            1295                1300                1305

Gln Phe Thr Met Gly Gly Ser  Pro Thr Pro Thr Asp  Tyr Thr Tyr
            1310                1315                1320

Thr Val Tyr Arg Asp Gly Thr  Lys Ile Lys Glu Gly  Leu Thr Glu
            1325                1330                1335

Thr Thr Phe Glu Glu Asp Gly  Val Ala Thr Gly Asn  His Glu Tyr
            1340                1345                1350

Cys Val Glu Val Lys Tyr Thr  Ala Gly Val Ser Pro  Lys Glu Cys
            1355                1360                1365

Val Asn Val Thr Val Asp Pro  Val Gln Phe Asn Pro  Val Gln Asn
            1370                1375                1380

Leu Thr Gly Ser Ala Val Gly  Gln Lys Val Thr Leu  Lys Trp Asp
```

-continued

```
            1385                1390                1395
Ala Pro Asn Gly Thr Pro Asn Pro Asn Pro Gly Thr Thr Thr Leu
    1400                1405                1410
Ser Glu Ser Phe Glu Asn Gly Ile Pro Ala Ser Trp Lys Thr Ile
    1415                1420                1425
Asp Ala Asp Gly Asp Gly Asn Asn Trp Thr Thr Thr Pro Pro Pro
    1430                1435                1440
Gly Gly Thr Ser Phe Ala Gly His Asn Ser Ala Ile Cys Val Ser
    1445                1450                1455
Ser Ala Ser Tyr Ile Asn Phe Glu Gly Pro Gln Asn Pro Asp Asn
    1460                1465                1470
Tyr Leu Val Thr Pro Glu Leu Ser Leu Pro Asn Gly Gly Thr Leu
    1475                1480                1485
Thr Phe Trp Val Cys Ala Gln Asp Ala Asn Tyr Ala Ser Glu His
    1490                1495                1500
Tyr Ala Val Tyr Ala Ser Ser Thr Gly Asn Asp Ala Ser Asn Phe
    1505                1510                1515
Ala Asn Ala Leu Leu Glu Glu Val Leu Thr Ala Lys Thr Val Val
    1520                1525                1530
Thr Ala Pro Glu Ala Ile Arg Gly Thr Arg Val Gln Gly Thr Trp
    1535                1540                1545
Tyr Gln Lys Thr Val Gln Leu Pro Ala Gly Thr Lys Tyr Val Ala
    1550                1555                1560
Phe Arg His Phe Gly Cys Thr Asp Phe Phe Trp Ile Asn Leu Asp
    1565                1570                1575
Asp Val Glu Ile Lys Ala Asn Gly Lys Arg Ala Asp Phe Thr Glu
    1580                1585                1590
Thr Phe Glu Ser Ser Thr His Gly Glu Ala Pro Ala Glu Trp Thr
    1595                1600                1605
Thr Ile Asp Ala Asp Gly Asp Gly Gln Gly Trp Leu Cys Leu Ser
    1610                1615                1620
Ser Gly Gln Leu Gly Trp Leu Thr Ala His Gly Gly Thr Asn Val
    1625                1630                1635
Val Ala Ser Phe Ser Trp Asn Gly Met Ala Leu Asn Pro Asp Asn
    1640                1645                1650
Tyr Leu Ile Ser Lys Asp Val Thr Gly Ala Thr Lys Val Lys Tyr
    1655                1660                1665
Tyr Tyr Ala Val Asn Asp Gly Phe Pro Gly Asp His Tyr Ala Val
    1670                1675                1680
Met Ile Ser Lys Thr Gly Thr Asn Ala Gly Asp Phe Thr Val Val
    1685                1690                1695
Phe Glu Glu Thr Pro Asn Gly Ile Asn Lys Gly Gly Ala Arg Phe
    1700                1705                1710
Gly Leu Ser Thr Glu Ala Asn Gly Ala Lys Pro Gln Ser Val Trp
    1715                1720                1725
Ile Glu Arg Thr Val Asp Leu Pro Ala Gly Thr Lys Tyr Val Ala
    1730                1735                1740
Phe Arg His Tyr Asn Cys Ser Asp Leu Asn Tyr Ile Leu Leu Asp
    1745                1750                1755
Asp Ile Gln Phe Thr Met Gly Gly Ser Pro Thr Pro Thr Asp Tyr
    1760                1765                1770
Thr Tyr Thr Val Tyr Arg Asp Gly Thr Lys Ile Lys Glu Gly Leu
    1775                1780                1785
```

```
Thr Glu Thr Thr Phe Glu Glu Asp Gly Val Ala Thr Gly Asn His
    1790            1795                1800

Glu Tyr Cys Val Glu Val Lys Tyr Thr Ala Gly Val Ser Pro Lys
    1805            1810                1815

Glu Cys Val Asn Val Thr Ile Asn Pro Thr Gln Phe Asn Pro Val
    1820            1825                1830

Gln Asn Leu Thr Ala Glu Gln Ala Pro Asn Ser Met Asp Ala Ile
    1835            1840                1845

Leu Lys Trp Asn Ala Pro Ala Ser Lys Arg Ala Glu Val Leu Asn
    1850            1855                1860

Glu Asp Phe Glu Asn Gly Ile Pro Ala Ser Trp Lys Thr Ile Asp
    1865            1870                1875

Ala Asp Gly Asp Gly Asn Asn Trp Thr Thr Thr Pro Pro Pro Gly
    1880            1885                1890

Gly Ser Ser Phe Ala Gly His Asn Ser Ala Ile Cys Val Ser Ser
    1895            1900                1905

Ala Ser Tyr Ile Asn Phe Glu Gly Pro Gln Asn Pro Asp Asn Tyr
    1910            1915                1920

Leu Val Thr Pro Glu Leu Ser Leu Pro Gly Gly Gly Thr Leu Thr
    1925            1930                1935

Phe Trp Val Cys Ala Gln Asp Ala Asn Tyr Ala Ser Glu His Tyr
    1940            1945                1950

Ala Val Tyr Ala Ser Ser Thr Gly Asn Asp Ala Ser Asn Phe Ala
    1955            1960                1965

Asn Ala Leu Leu Glu Glu Val Leu Thr Ala Lys Thr Val Val Thr
    1970            1975                1980

Ala Pro Glu Ala Ile Arg Gly Thr Arg Val Gln Gly Thr Trp Tyr
    1985            1990                1995

Gln Lys Thr Val Gln Leu Pro Ala Gly Thr Lys Tyr Val Ala Phe
    2000            2005                2010

Arg His Phe Gly Cys Thr Asp Phe Phe Trp Ile Asn Leu Asp Asp
    2015            2020                2025

Val Val Ile Thr Ser Gly Asn Ala Pro Ser Tyr Thr Tyr Thr Ile
    2030            2035                2040

Tyr Arg Asn Asn Thr Gln Ile Ala Ser Gly Val Thr Glu Thr Thr
    2045            2050                2055

Tyr Arg Asp Pro Asp Leu Ala Thr Gly Phe Tyr Thr Tyr Gly Val
    2060            2065                2070

Lys Val Val Tyr Pro Asn Gly Glu Ser Ala Ile Glu Thr Ala Thr
    2075            2080                2085

Leu Asn Ile Thr Ser Leu Ala Asp Val Thr Ala Gln Lys Pro Tyr
    2090            2095                2100

Thr Leu Thr Val Val Gly Lys Thr Ile Thr Val Thr Cys Gln Gly
    2105            2110                2115

Glu Ala Met Ile Tyr Asp Met Asn Gly Arg Arg Leu Ala Ala Gly
    2120            2125                2130

Arg Asn Thr Val Val Tyr Thr Ala Gln Gly Gly His Tyr Ala Val
    2135            2140                2145

Met Val Val Val Asp Gly Lys Ser Tyr Val Glu Lys Leu Ala Val
    2150            2155                2160

Lys
```

```
<210> SEQ ID NO 64
<211> LENGTH: 8
<212> TYPE: PRT
<213> ORGANISM: Porphyromonas gingivalis
<220> FEATURE:
<221> NAME/KEY: MOD_RES
<222> LOCATION: (2)..(2)
<223> OTHER INFORMATION: Ser or Tyr
<220> FEATURE:
<221> NAME/KEY: MOD_RES
<222> LOCATION: (3)..(3)
<223> OTHER INFORMATION: Tyr or Ser
<220> FEATURE:
<221> NAME/KEY: MOD_RES
<222> LOCATION: (6)..(6)
<223> OTHER INFORMATION: Pro or Ser
<220> FEATURE:
<221> NAME/KEY: MOD_RES
<222> LOCATION: (7)..(7)
<223> OTHER INFORMATION: Lys or Gln
<220> FEATURE:
<221> NAME/KEY: MOD_RES
<222> LOCATION: (8)..(8)
<223> OTHER INFORMATION: Ile or Val

<400> SEQUENCE: 64

Asp Xaa Xaa Trp Asn Xaa Xaa Xaa
1               5

<210> SEQ ID NO 65
<211> LENGTH: 7
<212> TYPE: PRT
<213> ORGANISM: Porphyromonas gingivalis

<400> SEQUENCE: 65

Asn Ser Tyr Trp Gly Glu Asp
1               5

<210> SEQ ID NO 66
<211> LENGTH: 11
<212> TYPE: PRT
<213> ORGANISM: Porphyromonas gingivalis
<220> FEATURE:
<221> NAME/KEY: MOD_RES
<222> LOCATION: (4)..(4)
<223> OTHER INFORMATION: Val or Ile

<400> SEQUENCE: 66

Ile Gly Asn Xaa Thr His Ile Gly Ala His Tyr
1               5                   10

<210> SEQ ID NO 67
<211> LENGTH: 8
<212> TYPE: PRT
<213> ORGANISM: Porphyromonas gingivalis

<400> SEQUENCE: 67

Glu Gly Gly Pro Ser Ala Asp Asn
1               5

<210> SEQ ID NO 68
<211> LENGTH: 7
<212> TYPE: PRT
<213> ORGANISM: Porphyromonas gingivalis
<220> FEATURE:
<221> NAME/KEY: MOD_RES
<222> LOCATION: (1)..(1)
<223> OTHER INFORMATION: Asn or Asp
<220> FEATURE:
<221> NAME/KEY: MOD_RES
<222> LOCATION: (3)..(3)
```

```
<223> OTHER INFORMATION: Ser or Tyr
<220> FEATURE:
<221> NAME/KEY: MOD_RES
<222> LOCATION: (6)..(6)
<223> OTHER INFORMATION: Ser or Pro

<400> SEQUENCE: 68

Xaa Gln Xaa Trp Ala Xaa Pro
1               5

<210> SEQ ID NO 69
<211> LENGTH: 23
<212> TYPE: PRT
<213> ORGANISM: Porphyromonas gingivalis

<400> SEQUENCE: 69

Pro Val Ser Asn Leu Thr Ala Thr Thr Gln Gly Gln Lys Val Thr Leu
1               5                   10                  15

Lys Trp Asp Ala Pro Ser Thr
            20

<210> SEQ ID NO 70
<211> LENGTH: 23
<212> TYPE: PRT
<213> ORGANISM: Porphyromonas gingivalis

<400> SEQUENCE: 70

Pro Val Ser Asn Leu Thr Ala Thr Thr Gln Gly Gln Lys Val Thr Leu
1               5                   10                  15

Lys Trp Glu Ala Pro Ser Ala
            20

<210> SEQ ID NO 71
<211> LENGTH: 23
<212> TYPE: PRT
<213> ORGANISM: Porphyromonas gingivalis

<400> SEQUENCE: 71

Pro Val Gln Asn Leu Thr Gly Ser Ser Val Gly Gln Lys Val Thr Leu
1               5                   10                  15

Lys Trp Asp Ala Pro Ser Thr
            20

<210> SEQ ID NO 72
<211> LENGTH: 23
<212> TYPE: PRT
<213> ORGANISM: Porphyromonas gingivalis

<400> SEQUENCE: 72

Pro Val Gln Asn Leu Thr Gly Ser Ala Val Gly Gln Lys Val Thr Leu
1               5                   10                  15

Lys Trp Asp Ala Pro Asn Gly
            20

<210> SEQ ID NO 73
<211> LENGTH: 23
<212> TYPE: PRT
<213> ORGANISM: Porphyromonas gingivalis

<400> SEQUENCE: 73

Pro Val Lys Asn Leu Lys Ala Gln Pro Asp Gly Gly Asp Val Val Leu
1               5                   10                  15

Lys Trp Glu Ala Pro Ser Ala
```

```
<210> SEQ ID NO 74
<211> LENGTH: 23
<212> TYPE: PRT
<213> ORGANISM: Porphyromonas gingivalis

<400> SEQUENCE: 74

Pro Val Gln Asn Leu Thr Ala Glu Gln Ala Pro Asn Ser Met Asp Ala
1               5                   10                  15

Ile Leu Lys Trp Asn Ala Pro
            20

<210> SEQ ID NO 75
<211> LENGTH: 24
<212> TYPE: PRT
<213> ORGANISM: Porphyromonas gingivalis

<400> SEQUENCE: 75

Pro Val Gln Asn Leu Thr Gln Trp Ser Val Ser Gly Gln Thr Val Thr
1               5                   10                  15

Leu Thr Trp Gln Ala Pro Ala Ser
            20

<210> SEQ ID NO 76
<211> LENGTH: 27
<212> TYPE: PRT
<213> ORGANISM: Porphyromonas gingivalis

<400> SEQUENCE: 76

Tyr Thr Tyr Thr Val Tyr Arg Asp Gly Thr Lys Ile Lys Glu Gly Leu
1               5                   10                  15

Thr Glu Thr Thr Phe Glu Glu Asp Gly Val Ala
            20                  25

<210> SEQ ID NO 77
<211> LENGTH: 27
<212> TYPE: PRT
<213> ORGANISM: Porphyromonas gingivalis

<400> SEQUENCE: 77

Tyr Thr Tyr Thr Val Tyr Arg Asp Asn Val Val Ile Ala Gln Asn Leu
1               5                   10                  15

Thr Ala Thr Thr Phe Asn Gln Glu Asn Val Ala
            20                  25

<210> SEQ ID NO 78
<211> LENGTH: 28
<212> TYPE: PRT
<213> ORGANISM: Porphyromonas gingivalis

<400> SEQUENCE: 78

Tyr Thr Tyr Thr Val Tyr Arg Asp Gly Thr Lys Ile Lys Glu Gly Leu
1               5                   10                  15

Thr Ala Glu Thr Thr Phe Glu Glu Asp Gly Val Ala
            20                  25

<210> SEQ ID NO 79
<211> LENGTH: 26
<212> TYPE: PRT
<213> ORGANISM: Porphyromonas gingivalis
<220> FEATURE:
<221> NAME/KEY: MOD_RES
```

```
<222> LOCATION: (6)..(17)
<223> OTHER INFORMATION: This region may encompass 1-6 "Asn-Pro"
      repeating units

<400> SEQUENCE: 79
```

Pro Asn Gly Thr Pro Asn Pro Asn Pro Asn Pro Asn Pro Asn Pro Asn
1               5                   10                  15

Pro Gly Thr Thr Thr Leu Ser Glu Ser Phe
                20                  25

```
<210> SEQ ID NO 80
<211> LENGTH: 326
<212> TYPE: PRT
<213> ORGANISM: Porphyromonas gingivalis

<400> SEQUENCE: 80
```

Gln Gly Gly Pro Lys Thr Ala Pro Ser Val Thr His Gln Ala Val Gln
1               5                   10                  15

Lys Gly Ile Arg Thr Ser Lys Ala Lys Asp Leu Arg Asp Pro Ile Pro
                20                  25                  30

Ala Gly Met Ala Arg Ile Ile Leu Glu Ala His Asp Val Trp Glu Asp
            35                  40                  45

Gly Thr Gly Tyr Gln Met Leu Trp Asp Ala Asp His Asn Gln Tyr Gly
        50                  55                  60

Ala Ser Ile Pro Glu Glu Ser Phe Trp Phe Ala Asn Gly Thr Ile Pro
65                  70                  75                  80

Ala Gly Leu Tyr Asp Pro Phe Glu Tyr Lys Val Pro Val Asn Ala Asp
                85                  90                  95

Ala Ser Phe Ser Pro Thr Asn Phe Val Leu Asp Gly Thr Ala Ser Ala
            100                 105                 110

Asp Ile Pro Ala Gly Thr Tyr Asp Tyr Val Ile Asn Pro Asn Pro
        115                 120                 125

Gly Ile Ile Tyr Ile Val Gly Glu Gly Val Ser Lys Gly Asn Asp Tyr
        130                 135                 140

Val Val Glu Ala Gly Lys Thr Tyr His Phe Thr Val Gln Arg Gln Gly
145                 150                 155                 160

Pro Gly Asp Ala Ala Ser Val Val Val Thr Gly Glu Gly Gly Asn Glu
                165                 170                 175

Phe Ala Pro Val Gln Asn Leu Gln Trp Ser Val Ser Gly Gln Thr Val
            180                 185                 190

Thr Leu Thr Trp Gln Ala Pro Ala Ser Asp Lys Arg Thr Tyr Val Leu
        195                 200                 205

Asn Glu Ser Phe Asp Thr Gln Thr Leu Pro Asn Gly Trp Thr Met Ile
        210                 215                 220

Asp Ala Asp Gly Asp Gly His Asn Trp Leu Ser Thr Ile Asn Val Tyr
225                 230                 235                 240

Asn Thr Ala Thr His Thr Gly Asp Gly Ala Met Phe Ser Lys Ser Trp
                245                 250                 255

Thr Ala Ser Ser Gly Ala Lys Ile Asp Leu Ser Pro Asp Asn Tyr Leu
            260                 265                 270

Val Thr Pro Lys Phe Thr Val Pro Glu Asn Gly Lys Leu Ser Tyr Trp
        275                 280                 285

Val Ser Ser Gln Glu Pro Trp Thr Asn Glu His Tyr Gly Val Phe Leu
        290                 295                 300

Ser Thr Thr Gly Asn Glu Ala Ala Asn Phe Thr Ile Lys Leu Leu Glu
305                 310                 315                 320

Glu Thr Leu Gly Ser Gly
            325

<210> SEQ ID NO 81
<211> LENGTH: 260
<212> TYPE: PRT
<213> ORGANISM: Porphyromonas gingivalis

<400> SEQUENCE: 81

Ala Pro Ala Pro Tyr Gln Glu Arg Thr Ile Asp Leu Ser Ala Tyr Ala
1               5                   10                  15

Gly Gln Gln Val Tyr Leu Ala Phe Arg His Phe Gly Cys Thr Gly Ile
            20                  25                  30

Phe Arg Leu Tyr Leu Asp Asp Val Ala Val Ser Gly Glu Gly Ser Ser
        35                  40                  45

Asn Asp Tyr Thr Tyr Thr Val Tyr Arg Asp Asn Val Val Ile Ala Gln
    50                  55                  60

Asn Leu Thr Ala Thr Thr Phe Asn Gln Glu Asn Val Ala Pro Gly Gln
65                  70                  75                  80

Tyr Asn Tyr Cys Val Glu Val Lys Tyr Thr Ala Gly Val Ser Pro Lys
                85                  90                  95

Val Cys Lys Asp Val Thr Val Glu Gly Ser Asn Glu Phe Ala Pro Val
            100                 105                 110

Gln Asn Leu Thr Gly Ser Ala Val Gly Gln Lys Val Thr Leu Lys Trp
        115                 120                 125

Asp Ala Pro Asn Gly Thr Pro Asn Pro Asn Pro Gly Thr Thr Thr Leu
    130                 135                 140

Ser Glu Ser Phe Glu Asn Gly Ile Pro Ala Ser Trp Lys Thr Ile Asp
145                 150                 155                 160

Ala Asp Gly Asp Gly Asn Asn Trp Thr Thr Pro Pro Gly Gly
                165                 170                 175

Ser Ser Phe Ala Gly His Asn Ser Ala Ile Cys Val Ser Ala Ser
        180                 185                 190

Tyr Ile Asn Phe Glu Gly Pro Gln Asn Pro Asp Asn Tyr Leu Val Thr
    195                 200                 205

Pro Glu Leu Ser Leu Pro Asn Gly Gly Thr Leu Thr Phe Trp Val Cys
210                 215                 220

Ala Gln Asp Ala Asn Tyr Ala Ser Glu His Tyr Ala Val Tyr Ala Ser
225                 230                 235                 240

Ser Thr Gly Asn Asp Ala Ser Asn Phe Ala Asn Ala Leu Leu Glu Glu
                245                 250                 255

Val Leu Thr Ala
            260

<210> SEQ ID NO 82
<211> LENGTH: 258
<212> TYPE: PRT
<213> ORGANISM: Porphyromonas gingivalis

<400> SEQUENCE: 82

Pro Gln Ser Val Trp Ile Glu Arg Thr Val Asp Leu Pro Ala Gly Thr
1               5                   10                  15

Lys Tyr Val Ala Phe Arg His Tyr Asn Cys Ser Asp Leu Asn Tyr Ile
            20                  25                  30

Leu Leu Asp Asp Ile Gln Phe Thr Met Gly Gly Ser Pro Thr Pro Thr
        35                  40                  45

```
Asp Tyr Thr Tyr Thr Val Tyr Arg Asp Gly Thr Lys Ile Lys Glu Gly
    50                  55                  60

Leu Thr Glu Thr Thr Phe Glu Glu Asp Gly Val Ala Thr Gly Asn His
65                  70                  75                  80

Glu Tyr Cys Val Glu Val Lys Tyr Thr Ala Gly Val Ser Pro Lys Glu
                85                  90                  95

Cys Val Asn Val Thr Val Asp Pro Val Gln Phe Asn Pro Val Gln Asn
            100                 105                 110

Leu Thr Gly Ser Ala Val Gly Gln Lys Val Thr Leu Lys Trp Asp Ala
        115                 120                 125

Pro Asn Gly Thr Pro Asn Pro Asn Pro Gly Thr Thr Thr Leu Ser Glu
    130                 135                 140

Ser Phe Glu Asn Gly Ile Pro Ala Ser Trp Lys Thr Ile Asp Ala Asp
145                 150                 155                 160

Gly Asp Gly Asn Asn Trp Thr Thr Thr Pro Pro Gly Gly Thr Ser
                165                 170                 175

Phe Ala Gly His Asn Ser Ala Ile Cys Val Ser Ser Ala Ser Tyr Ile
                180                 185                 190

Asn Phe Glu Gly Pro Gln Asn Pro Asp Asn Tyr Leu Val Thr Pro Glu
            195                 200                 205

Leu Ser Leu Pro Asn Gly Gly Thr Leu Thr Phe Trp Val Cys Ala Gln
        210                 215                 220

Asp Ala Asn Tyr Ala Ser Glu His Tyr Ala Val Tyr Ala Ser Ser Thr
225                 230                 235                 240

Gly Asn Asp Ala Ser Asn Phe Ala Asn Ala Leu Leu Glu Glu Val Leu
                245                 250                 255

Thr Ala

<210> SEQ ID NO 83
<211> LENGTH: 15
<212> TYPE: PRT
<213> ORGANISM: Porphyromonas gingivalis

<400> SEQUENCE: 83

Pro Tyr Gln Pro Val Ser Asn Leu Thr Ala Thr Thr Gln Gly Gln
1               5                   10                  15

<210> SEQ ID NO 84
<211> LENGTH: 15
<212> TYPE: PRT
<213> ORGANISM: Porphyromonas gingivalis

<400> SEQUENCE: 84

Glu Gly Leu Thr Ala Thr Thr Phe Glu Glu Asp Gly Val Ala Ala
1               5                   10                  15

<210> SEQ ID NO 85
<211> LENGTH: 17
<212> TYPE: PRT
<213> ORGANISM: Porphyromonas gingivalis

<400> SEQUENCE: 85

Gly Thr Pro Asn Pro Asn Pro Asn Pro Asn Pro Asn Pro Asn Pro Gly
1               5                   10                  15

Thr

<210> SEQ ID NO 86
```

```
<211> LENGTH: 13
<212> TYPE: PRT
<213> ORGANISM: Bos taurus

<400> SEQUENCE: 86

Leu Pro Gln Glu Val Leu Asn Glu Asn Leu Leu Arg Phe
1               5                   10

<210> SEQ ID NO 87
<211> LENGTH: 17
<212> TYPE: PRT
<213> ORGANISM: bos taurus

<400> SEQUENCE: 87

Tyr Gln Glu Pro Val Leu Gly Pro Val Arg Gly Pro Phe Pro Ile Ile
1               5                   10                  15

Val

<210> SEQ ID NO 88
<211> LENGTH: 29
<212> TYPE: PRT
<213> ORGANISM: Bos taurus

<400> SEQUENCE: 88

Pro Pro Lys Lys Asn Gln Asp Lys Thr Glu Ile Pro Thr Ile Asn Thr
1               5                   10                  15

Ile Ala Ser Gly Glu Pro Thr Ser Thr Pro Thr Thr Glu
            20                  25

<210> SEQ ID NO 89
<211> LENGTH: 13
<212> TYPE: PRT
<213> ORGANISM: bos taurus

<400> SEQUENCE: 89

Tyr Gln Glu Pro Val Leu Gly Pro Val Arg Gly Pro Phe
1               5                   10

<210> SEQ ID NO 90
<211> LENGTH: 21
<212> TYPE: PRT
<213> ORGANISM: Bos taurus

<400> SEQUENCE: 90

Thr Glu Ile Pro Thr Ile Asn Thr Ile Ala Ser Gly Glu Pro Thr Ser
1               5                   10                  15

Thr Pro Thr Thr Glu
            20

<210> SEQ ID NO 91
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Leu Ile Gly Lys
1

<210> SEQ ID NO 92
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 92

Leu Ile Gly Lys Val
1               5

<210> SEQ ID NO 93
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 93

His His His His His His
1               5

<210> SEQ ID NO 94
<211> LENGTH: 8
<212> TYPE: PRT
<213> ORGANISM: Porphyromonas gingivalis

<400> SEQUENCE: 94

Asn Thr Gly Val Ser Phe Ala Asn
1               5

<210> SEQ ID NO 95
<211> LENGTH: 8
<212> TYPE: PRT
<213> ORGANISM: Porphyromonas gingivalis

<400> SEQUENCE: 95

Thr Gly Val Ser Phe Ala Asn Tyr
1               5

<210> SEQ ID NO 96
<211> LENGTH: 8
<212> TYPE: PRT
<213> ORGANISM: Porphyromonas gingivalis

<400> SEQUENCE: 96

Ser Phe Ala Asn Tyr Thr Ala His
1               5

<210> SEQ ID NO 97
<211> LENGTH: 8
<212> TYPE: PRT
<213> ORGANISM: Porphyromonas gingivalis

<400> SEQUENCE: 97

Phe Ala Asn Tyr Thr Ala His Gly
1               5

<210> SEQ ID NO 98
<211> LENGTH: 8
<212> TYPE: PRT
<213> ORGANISM: Porphyromonas gingivalis

<400> SEQUENCE: 98

Ala Asn Tyr Thr Ala His Gly Ser
1               5
```

<210> SEQ ID NO 99
<211> LENGTH: 8
<212> TYPE: PRT
<213> ORGANISM: Porphyromonas gingivalis

<400> SEQUENCE: 99

Asn Tyr Thr Ala His Gly Ser Glu
1               5

<210> SEQ ID NO 100
<211> LENGTH: 8
<212> TYPE: PRT
<213> ORGANISM: Porphyromonas gingivalis

<400> SEQUENCE: 100

Tyr Thr Ala His Gly Ser Glu Thr
1               5

<210> SEQ ID NO 101
<211> LENGTH: 8
<212> TYPE: PRT
<213> ORGANISM: Porphyromonas gingivalis

<400> SEQUENCE: 101

Thr Ala His Gly Ser Glu Thr Ala
1               5

<210> SEQ ID NO 102
<211> LENGTH: 8
<212> TYPE: PRT
<213> ORGANISM: Porphyromonas gingivalis

<400> SEQUENCE: 102

Ala His Gly Ser Glu Thr Ala Trp
1               5

<210> SEQ ID NO 103
<211> LENGTH: 8
<212> TYPE: PRT
<213> ORGANISM: Porphyromonas gingivalis

<400> SEQUENCE: 103

His Gly Ser Glu Thr Ala Trp Ala
1               5

<210> SEQ ID NO 104
<211> LENGTH: 8
<212> TYPE: PRT
<213> ORGANISM: Porphyromonas gingivalis

<400> SEQUENCE: 104

Ala Trp Ala Asp Pro Leu Leu Thr
1               5

<210> SEQ ID NO 105
<211> LENGTH: 8
<212> TYPE: PRT
<213> ORGANISM: Porphyromonas gingivalis

<400> SEQUENCE: 105

Trp Ala Asp Pro Leu Leu Thr Thr
1               5

<210> SEQ ID NO 106

<211> LENGTH: 8
<212> TYPE: PRT
<213> ORGANISM: Porphyromonas gingivalis

<400> SEQUENCE: 106

Ala Asp Pro Leu Leu Thr Thr Ser
1               5

<210> SEQ ID NO 107
<211> LENGTH: 8
<212> TYPE: PRT
<213> ORGANISM: Porphyromonas gingivalis

<400> SEQUENCE: 107

Asp Pro Leu Leu Thr Thr Ser Gln
1               5

<210> SEQ ID NO 108
<211> LENGTH: 8
<212> TYPE: PRT
<213> ORGANISM: Porphyromonas gingivalis

<400> SEQUENCE: 108

Pro Leu Leu Thr Thr Ser Gln Leu
1               5

<210> SEQ ID NO 109
<211> LENGTH: 8
<212> TYPE: PRT
<213> ORGANISM: Porphyromonas gingivalis

<400> SEQUENCE: 109

Leu Leu Thr Thr Ser Gln Leu Lys
1               5

<210> SEQ ID NO 110
<211> LENGTH: 8
<212> TYPE: PRT
<213> ORGANISM: Porphyromonas gingivalis

<400> SEQUENCE: 110

Leu Thr Thr Ser Gln Leu Lys Ala
1               5

<210> SEQ ID NO 111
<211> LENGTH: 8
<212> TYPE: PRT
<213> ORGANISM: Porphyromonas gingivalis

<400> SEQUENCE: 111

Thr Thr Ser Gln Leu Lys Ala Leu
1               5

<210> SEQ ID NO 112
<211> LENGTH: 8
<212> TYPE: PRT
<213> ORGANISM: Porphyromonas gingivalis

<400> SEQUENCE: 112

Thr Ser Gln Leu Lys Ala Leu Thr
1               5

<210> SEQ ID NO 113
<211> LENGTH: 8
<212> TYPE: PRT

```
<213> ORGANISM: Porphyromonas gingivalis

<400> SEQUENCE: 113

Ser Gln Leu Lys Ala Leu Thr Asn
1               5

<210> SEQ ID NO 114
<211> LENGTH: 8
<212> TYPE: PRT
<213> ORGANISM: Porphyromonas gingivalis

<400> SEQUENCE: 114

Gln Leu Lys Ala Leu Thr Asn Lys
1               5

<210> SEQ ID NO 115
<211> LENGTH: 8
<212> TYPE: PRT
<213> ORGANISM: Porphyromonas gingivalis

<400> SEQUENCE: 115

Leu Lys Ala Leu Thr Asn Lys Asp
1               5

<210> SEQ ID NO 116
<211> LENGTH: 8
<212> TYPE: PRT
<213> ORGANISM: Porphyromonas gingivalis

<400> SEQUENCE: 116

Lys Ala Leu Thr Asn Lys Asp Lys
1               5
```

TREATMENT OR PREVENTION OF INFECTION

FIELD OF THE INVENTION

The invention relates to the treatment or prevention of diseases or conditions in a subject, said diseases or conditions being associated with the presence of a microbial pathogen in an oral tissue of a subject, and in particular, but not exclusively, to the treatment or prevention of *P. gingivalis*-related diseases or conditions.

BACKGROUND OF THE INVENTION

The mouth constitutes one of the major sites of infection. Infection can lead to debilitating disease of oral tissue and a clear association has also been observed between infection of oral tissue and disease or condition in other anatomical compartments.

Chronic periodontitis is one example of a disease of oral tissue. This is an inflammatory disease of the supporting tissues of the teeth leading to resorption of alveolar bone and eventual tooth loss. The disease is a major public health problem in all societies and is estimated to affect up to 15% of the adult population with severe forms affecting 5-6%.

The development and progression of chronic periodontitis has been associated with specific Gram-negative bacteria in subgingival plaque. The presence of *Porphyromonas gingivalis* in subgingival plaque has been strongly associated with disease.

The persistence of *P. gingivalis* in subgingival plaque from periodontitis patients after treatment (scaling and root planing) has been reported to be significantly associated with progressive alveolar bone loss. Furthermore an increase in *P. gingivalis* cell numbers in subgingival plaque has been shown to correlate with disease severity as measured by attachment loss, periodontal pocket depth and bleeding on probing.

Oral infection with *P. gingivalis* has been shown to induce periodontal bone loss in mice, rats and non-human primates. In addition, there has been increasing linkage of periodontal disease, and of *P. gingivalis* infection, with cardiovascular diseases and certain cancers.

Many other microbial pathogens, including other bacteria, fungi, virus and protozoa have been associated with disease of oral tissue and some of these pathogens also cause disease in other anatomical compartments via infection of oral tissue. Examples of the former include *T. denticola* and *T. forsythia*. Group A *Streptococcus* infection is an aetiological agent of rheumatic fever and rheumatic heart disease.

One problem has been that it is not clear how to obtain a strong protective response to a given microbial pathogen in circumstances where mucosal tissue has been chronically inflamed, or where acute inflammation of mucosal tissue has arisen from surgical or other dental intervention.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

SUMMARY OF THE INVENTION

In certain embodiments there is provided a method of reducing the incidence or severity of a disease or condition in a subject, said disease or condition being one associated with the presence of a microbial pathogen in an oral tissue of a subject, the method including:

treating a subject, thereby providing conditions for removal of substantially all micro-organisms or fragments thereof from oral tissue of said subject; thereafter providing an antibody in said subject, said antibody for protecting said subject against a microbial pathogen, the presence of which in oral tissue is associated with a disease or condition; thereby reducing the incidence or severity of a disease or condition in a subject.

In one embodiment, the antibody is provided in said subject by administering an immunogen to said subject, said immunogen for protecting said subject against a microbial pathogen.

In one embodiment there is provided a method of reducing the incidence or severity of a *P. gingivalis*-related disease or condition in a subject, the method including:

treating a subject, thereby removing substantially all micro-organisms or fragments thereof from oral tissue of said subject; thereafter administering a chimeric or fusion protein for inducing an immune response to *P. gingivalis* to the subject, the protein including a first peptide joined directly or through a linker to a second peptide, wherein:

(A) said first peptide includes:
        (i) part of, or all of a sequence that is the same as, or homologous to the sequence shown in SEQ ID No:1; or
        (ii) part of, or all of a sequence that is the same as, or homologous to the sequence shown in SEQ ID No:2; and (B) said second peptide includes:
        (i) part of, or all of a sequence that is the same as, or homologous to the sequence of an adhesin domain of the Lys-X-proteinase of *P. gingivalis*; or
        (ii) part of, or all of a sequence that is the same as, or homologous to the sequence of an adhesin domain of the Arg-X-proteinase of *P. gingivalis*; or
        (iii) part of, or all of a sequence that is the same as, or homologous to the sequence of a HagA adhesin domain of *P. gingivalis*.

thereby reducing the incidence or severity of a disease or condition in a subject.

In other embodiments there is provided a composition or kit including:

anti-microbial agent for removing substantially all microorganisms or fragments thereof from oral tissue of said subject;

an immunogen for immunising said subject against a microbial pathogen, the presence of which in oral tissue is associated with a disease or condition;

said composition or kit for use in a method described above.

In certain embodiments there is provided a method of reducing the incidence or severity of a disease or condition in a subject, said disease or condition being one associated with the presence of a microbial pathogen in an oral tissue of a subject, the method including:

performing a surgical procedure on oral tissue of a subject; thereafter treating the subject, thereby providing conditions for removal of substantially all micro-organisms or fragments thereof from oral tissue of said subject;

providing an antibody in the subject, said antibody for protecting said subject against a microbial pathogen, the presence of which in oral tissue is associated with a disease or condition;

thereby reducing the incidence or severity of a disease or condition in a subject.

In one embodiment the surgical procedure is a dental procedure. Examples of dental procedures include debridement, scaling and/or root planning.

In one embodiment, the present invention provides a composition for reducing the incidence or severity of a disease or condition in a subject, said disease or condition being one associated with the presence of a microbial pathogen in an oral tissue of a subject, the composition including an anti-microbial agent as described herein and an immunogen as described herein.

In another aspect, the invention provides a use of a composition of the invention in the preparation of a medicament for reducing the incidence or severity of a disease or condition in a subject, said disease or condition being one associated with the presence of a microbial pathogen in an oral tissue of a subject. Non-limiting examples of diseases include dental plaque, gingivitis, periodontitis, chronic periodontitis, dental caries, bone loss, alveolar bone loss and coronary artery disease.

In another embodiment the invention provides a composition for the treatment or prevention of periodontal disease (and/or the other conditions identified herein as suitable for treatment) consisting of an active ingredient of anti-microbial agent as described herein and an immunogen as described herein.

In another embodiment the invention provides a composition comprising anti-microbial agent as described herein and an immunogen as described herein for use in for reducing the incidence or severity of a disease or condition in a subject, said disease or condition being one associated with the presence of a microbial pathogen in an oral tissue of a subject.

In another embodiment the invention provides a composition as described herein for use as a medicament.

In another embodiment the invention provides a pharmaceutical composition comprising an effective amount of a composition of the invention as a main ingredient.

In one embodiment there is provided a method for forming an antibody response or for forming a Th2 response to an oral pathogen in an individual including the steps of:
  providing an individual in whom an antibody or Th2 response to an oral pathogen is to be formed;
  assessing the individual to determine whether the individual has inflamed oral tissue;
  immunising the individual with an oral pathogen in circumstances where the assessment reveals that the individual does not have inflamed oral tissue, thereby forming an antibody response or Th2 response to an oral pathogen in the individual.

In one embodiment there is provided, in an immunisation regime for the formation of an antibody response or the formation of a Th2 response to an oral pathogen in an individual having inflamed oral tissue, the step of administering an anti-inflammatory agent to the individual, thereby minimising inflammation of, or removing inflammation from the oral tissue, prior to an immunisation of the individual for the formation of an antibody response or Th2 response to an oral pathogen.

In another embodiment there is provided a method for conditioning an individual having an inflamed oral tissue to form an antibody response or to form a Th2 response to an oral pathogen upon immunisation with the pathogen, the method including the step of administering an anti-inflammatory agent to the individual, thereby minimising inflammation of, or removing inflammation from the oral tissue, prior to an immunisation of the individual with a pathogen for the formation of an antibody response or the formation of a Th2 response to an oral pathogen.

In a further embodiment there is provided a method of forming an antibody response or forming a Th2 response to an oral pathogen in an individual having inflamed oral tissue including the steps of:
  providing an individual having inflamed oral tissue;
  applying a treatment to the individual, thereby removing inflammation from the oral tissue; thereafter;
  immunising the individual with an oral pathogen, thereby forming an antibody response or forming a Th2 response to the pathogen in the individual.

In the above described embodiments, an immunisation is to be provided at a time when oral tissue is not inflamed, or when inflammation is subclinical or asymptomatic.

Typically an immune response formed upon immunisation is predominantly a Th2 response, although it may contain detectable components of a Th1 response.

Typically the relevant inflammation is chronic periodontitis, especially periodontitis associated with *P. gingivalis* infection.

Where the periodontitis is associated with *P. gingivalis* infection, typically an immunogen for immunisation is a *P. gingivalis* cell, fragment, metabolite, or recombinant product derived therefrom, such as the chimeric peptides (especially KAS1-KsA1, KAS2-KLA1) described herein.

Typically the anti-inflammatory agent or anti-microbial agent as defined herein includes or consists of one or more of an anti-inflammatory compound, an anti-biotic and an anti-biofilm agent, examples of which are described in more detail herein.

As used herein, except where the context requires otherwise, the term "comprise" and variations of the term, such as "comprising", "comprises" and "comprised", are not intended to exclude further additives, components, integers or steps.

DETAILED DESCRIPTION OF THE EMBODIMENTS

Figure 1:
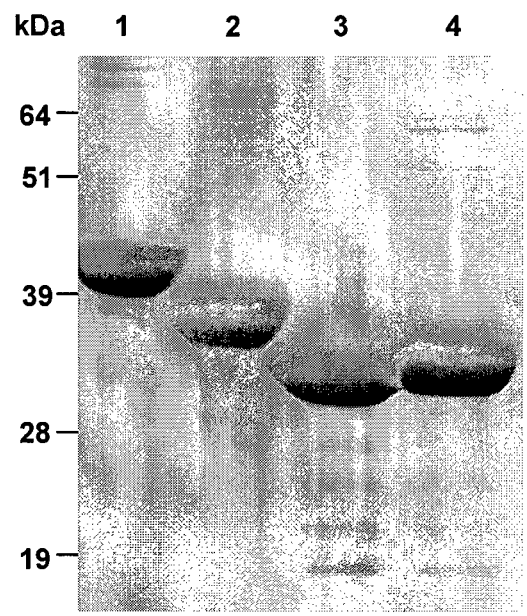
FIG. 1 shows a coomassie blue stain of the SDS-PAGE gel of recombinant Kgp Proteins. Lane 1=KAS2-KLA1, Lane 2=KLA1, Lane 3=KsA1, Lane 4=KAS1-KsA1. Molecular weight markers are indicated as kDa.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

It will be understood that the invention disclosed and defined in this specification extends to all alternative combinations of two or more of the individual features mentioned or evident from the text or drawings. All of these different combinations constitute various alternative aspects of the invention.

As used herein, except where the context requires otherwise, the term "comprise" and variations of the term, such as "comprising", "comprises" and "comprised", are not intended to exclude further additives, components, integers or steps.

The inventors have found that an improved response to infection, especially, an improved antibody response can be obtained by removing substantially all inflammatory stimuli from oral tissue, prior to, providing adoptive transfer of immunity in the tissue, or at the time of invoking an immune response in the tissue. The finding is particularly useful insofar as it provides for the prevention and/or treatment of disease in oral tissue and by extension, for the prevention and/or treatment of disease that arises in other anatomical compartments as a consequence of infection of oral tissue by a microbial pathogen.

Thus in certain embodiments there is provided a method of reducing the incidence or severity of a disease or condition in a subject, said disease or condition being one associated with the presence of a microbial pathogen in an oral tissue of a subject, the method including:

treating a subject, thereby providing conditions for removal of substantially all micro-organisms and fragments thereof from oral tissue of said subject; thereafter providing an antibody in said subject, said antibody for protecting said subject against a microbial pathogen, the presence of which in oral tissue is associated with a disease or condition;

thereby reducing the incidence or severity of a disease or condition in a subject.

In one embodiment, the antibody is provided in said subject by administering an immunogen to said subject, said immunogen for protecting said subject against a microbial pathogen.

In one embodiment, an anti-microbial composition for treating a subject, thereby providing conditions for removal of substantially all micro-organisms and fragments thereof from oral tissue of said subject and immunogen are provided in synergistically effective amounts.

Typically, the subject referred to herein is an animal, especially a mammal. In one embodiment the mammal is human. In certain embodiments the mammal may be a domesticated or farmed animal. Examples of domesticated or farmed animals include horses, goats, pigs and livestock such as cattle and sheep. In certain embodiments the animal is a companion animal such as a dog, cat, rabbit or guinea pig.

1. DEFINITIONS

The phrase 'removal of substantially all micro-organisms and fragments thereof from oral tissue' generally refers to providing conditions in which micro-organisms or fragments or metabolites thereof are depleted from the tissue in a quantity sufficient to deplete inflammatory stimuli from the tissue, thereby substantially reducing or minimising one or more symptoms of inflammation in said tissue. This is particularly the case where the relevant subject has chronic inflammation of tissue stemming from chronic infection. Generally the focus is on minimising inflammation of tissue. Accordingly it will be understood that some micro-organisms, fragments and metabolites thereof may remain after the relevant treatment step.

In other embodiments where the individual does not have inflamed tissue, the phrase 'removal of substantially all micro-organisms and fragments thereof from oral tissue' refers to providing conditions which substantially prevent the accumulation of micro-organisms, fragments and metabolites thereof to a quantity that would cause inflammation. This is particularly the case where the subject for treatment is normal or otherwise asymptomatic for a disease or condition. The same applies where surgical or dental intervention has removed micro-organisms and the objective is to ensure that conditions are provided which substantially prevent the accumulation of micro-organisms in amounts that would cause inflammation. In these embodiments as the focus is to prevent accumulation of amounts of micro-organisms that might cause inflammation, it will be understood that some micro-organisms, fragments or metabolites therefrom might accumulate after the relevant treatment step.

The phrase 'reducing the incidence of disease or a condition' generally refers to minimising the likelihood of a subject—be it a normal or asymptomatic individual, or a subjecting having an early form of a disease or condition—from progressing to a complete active form of the disease or condition. In certain embodiments the phrase refers to preventing a given subject from progressing to a complete active form of a disease or condition.

The phrase 'reducing the severity of disease or a condition' generally refers to minimising one or more symptoms or manifestations or a disease or condition. In certain embodiments the phrase refers to treating an individual having a disease or condition.

An 'immunogen' generally refers to a molecule that is capable of invoking or eliciting an immune response to antigen, preferably a humoral or antibody response, for example, a Th2 response. Examples of immunogens include peptides and related proteins.

The phrase 'synergistically effective amounts' generally refers to amounts of an anti-microbial composition and immunogen that provide a treatment or preventive or protective effect that is greater than the effect that can be achieved by the composition or immunogen when each is used alone. In one embodiment, synergistically effective amounts of the anti-microbial composition and immunogen underpin a novel working interrelationship between said composition and immunogen whereby the protective or therapeutic effective of said immunogen is much greater than can be achieved when the immunogen alone is applied to inflamed tissue. Typically a synergistically effective amounts of microbial composition and immunogen provide for a higher titer and/or higher affinity antibody response to microbial pathogens than can be realised when the immunogen is used alone.

The phrase 'therapeutically effective amount' generally refers to an amount of a compound of the present invention that (i) treats the particular disease, condition, or disorder, (ii) attenuates, ameliorates, or eliminates one or more symptoms of the particular disease, condition, or disorder, or (iii) delays the onset of one or more symptoms of the particular disease, condition, or disorder described herein.

The words 'treat' or 'treatment' refer to therapeutic treatment wherein the object is to slow down (lessen) an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. 'Treatment' can also mean prolonging survival as compared to expected survival if not receiving treatment. Treatment may not necessarily result in the complete clearance of an infection but may reduce or minimise complications and side effects of infection and the progression of infection. The success or otherwise of treatment may be monitored by physical examination of the individual, cytopathological, serological DNA, or mRNA detection techniques.

The words 'prevent' and 'prevention' generally refer to prophylactic or preventative measures for protecting or precluding an individual not having a given infection related complication from progressing to that complication. Individuals in which prevention is required include those who have an infection.

The phrase 'pharmaceutically acceptable' indicates that the substance or composition must be compatible chemically and/or toxicologically, with the other ingredients comprising a formulation, and/or the mammal being treated therewith.

The term 'package insert' is used to refer to instructions customarily included in commercial packages of therapeutic products, that contain information about the indications, usage, dosage, administration, contraindications and/or warnings concerning the use of such therapeutic products.

A Th1 response generally refers to a response involving cytokines such as interferon gamma and TNF.

A Th2 response generally refers to a response involving cytokines such as interleukin-4, interleukin-5, interleukin-6, interleukin-10, interleukin-13 etc.

2. METHODS OF TREATMENT

The methods of the invention are applicable to a wide range of subjects including those who are asymptomatic for said disease or condition. These individuals may have no symptoms of disease in oral or other tissue. Specifically, these individuals may not present with inflammation of mucosal or other oral tissue. In one embodiment, these individuals may have, in the context of a randomly selected cohort of subjects, a normal relative abundance of microbial pathogens in the oral cavity.

In other embodiments, the subject manifests sub clinical or clinical symptoms of a disease or condition of oral tissue or other anatomical compartment.

The symptoms of said disease or condition may be manifested in oral tissue of said subject. The hallmarks of acute inflammation may be present including an increased movement of plasma and leukocytes from the blood into the injured tissues. Clinical signs of acute infection of the gingiva may also be present including rubor (redness), calor (increased heat), tumor (swelling), dolor (pain), and functio laesa (loss of function). Chronic inflammation may be characterised by leukocyte cell (monocytes, macrophages, lymphocytes, plasma cells) infiltration. Tissue and bone loss may be observed. Examples of inflammation include cheilits, gingivitis, glossitis and stomatitis.

In one embodiment, the subject may have inflamed mucosal or other oral tissue. For example, the subject may present with acute inflammation of oral tissue. Examples of these subjects include those who have been subjected to dental or oral surgery including debridement, scaling and root planing.

In further embodiments, the subject may present with chronic inflammation of oral tissue. In one example the subject may present with gingivitis, resorption of alveolar bone and eventual tooth loss stemming from progressive loss of collagen attachment of the tooth to alveolar bone. Other lesions of mucosal or related oral tissue are possible.

In one embodiment, the disease or condition is a disease or condition of oral tissue. Chronic periodontitis is a particularly important example. Others include diseases and conditions characterised by damage to oral mucosa as in Scarlet Fever, Aphthous Stomatitis, Pyogenic Granuloma, Diphtheria, Tuberculosis, Syphilis, Actinomycosis, Candidiasis, Herpetic Stomatitis.

It will be understood that the disease or condition may be a disease or condition of a tissue other than the oral tissue such as an organ or system, for example, the cardiovascular system. In one embodiment, the disease or condition is cardiovascular disease.

The invention is applicable to a range of microbial pathogen, especially those that infect the tissues of the oral cavity. In one embodiment, the pathogen is selected from the group consisting of bacteria, virus and fungi.

Particularly preferred bacteria are selected from the group consisting of: *Porphyromonas gingivalis, Treponema denticola, Tannerella forsythia*.

Other examples of pathogens are shown in Table A below.

TABLE A

| Organism | Exemplary family/genus | Exemplary species |
|---|---|---|
| Bacteria | Streptococci | salivarius |
| | | mutans |
| | | sanguis |
| | | pneumoniae |
| | | pyogenes |
| | | mitis |
| | Neisseria | meningitidis |
| | Lactobacilli | plantarum |
| | Proteus | |
| | Bacteroides | |
| | staphylococci | epidermidis |
| | | aureus |
| | Pseudomonas | aeruginosa |
| | Clostridium | perfringens |
| | | tetani |
| | Corynebacteria | |
| | Enterococci | faecalis |
| | Veillonella | |
| | Treponema | denticola |
| | Porphyromonas | gingivalis |
| | Tanneralla | forsythia |
| | Aggregatibacter | actinomycetemcomitans |
| | Actinomycetes | |
| | Spirochetes | |
| | Mycoplasmas | |
| Fungi | Candida | albicans |
| | | khmerensis |
| | | metapsilosis |
| | | parapsilosis |
| | | tropicalis |
| | Cladosporium | cladosporioides |
| | | sphaerospermum |
| | | herbarum |
| | | tenuissimum |
| | Aureobasidium | pullulans |
| | Saccharomycetales | |
| | Fusarium | culmorum |
| | | oxysporum |
| | | poae |
| | Aspergillus | amstelodami |
| | | caesiellus |
| | | flavus |
| | | oryzae |
| | | penicillioides |
| | | ruber |
| | Xylariales | |
| | Glomus | fulvum |
| | | mosseae |
| | Leptosphaeriaceae | |
| | Ascomycete | |
| | Basidiomycete | |
| | Ophiostoma | floccosum |
| | | pulvinisporum |
| | Ectomycorrhiza | |
| | Penicillium | brevicompactum |
| | | glabrum |
| | | spinulosum |
| | Endophytic fungi | |
| | Glomeromycete. | |
| | Alternaria | tenuissima |
| | | triticina |
| | Cryptococcus | cellulolyticus |
| | | diffluens |
| | Phoma | foveata |
| | | plurivora |
| | Saccharomyces | bayanus |
| | | cerevisiae |
| | | ellipsoideus |
| | Schizosaccharomyces | japonicus |
| | | pombe |
| | Zygosaccharomyces | pseudorouxii |
| | | rouxii |
| Protozoa | Entamoeba | Gingivalis |
| | Trichomonas | Tenax |
| | Leishmania | brasiliensis |
| Viruses | Herpesvirus | Herpesvirus 1 to 8 |
| | Papillomavirus | Human papilomavirus (HPV) -1, HPV-3, HPV-27, HPV-29, and HPV-57 |
| | Enteroviruses | Coxsackie virus A16 and enterovirus-71 |

In one embodiment, a composition forming an anti-microbial agent is administered to the subject, thereby removing substantially all micro-organisms or fragments thereof from oral tissue of said subject. Examples are discussed further below.

In one embodiment, providing in the subject an antibody, for example by administering an immunogen to the subject, occurs one to two weeks after treatment of an infected site by mechanical debridement and/or the application of one or more of the anti-microbial agents as defined herein.

The level of or presence of micro-organisms, fragments or metabolites thereof can be determined by detecting or measuring a protein or fragment thereof from a micro-organism.

In another embodiment, the level of or presence of micro-organisms, fragments or metabolites thereof in an oral tissue can be determined by taking a sample from the individual and determining the presence of a given protein, or level of expression of a given protein in the sample. The presence of or level of a protein can be detected by any number of assays. Examples include immunoassays, chromatography and mass spectrometry. One example of an immunoassay that is particular preferred is FACS.

Various assays that can be used to detect the presence of a target protein in a sample include:

Enzyme linked immunosorbent assay (ELISA): This method involves fixation of a sample, for example saliva or oral tissue, containing a target protein, peptide or fragment thereof to a surface such as a well of a microtiter plate. A target protein specific antibody coupled to an enzyme is applied and allowed to bind to the target protein, peptide or fragment thereof. Presence of the antibody is then detected and quantitated by a colorimetric reaction employing the enzyme coupled to the antibody. Enzymes commonly employed in this method include horseradish peroxidase and alkaline phosphatase. If well calibrated and within the linear range of response, the amount of target protein, peptide or fragment thereof present in the sample is proportional to the amount of color produced. A target protein, peptide or fragment thereof standard is generally employed to improve quantitative accuracy.

Western blot: This method involves separation of a target protein, peptide or fragment thereof from other protein by means of an acrylamide gel followed by transfer of the protein, peptide or fragment thereof to a membrane (e.g., nylon or PVDF). Presence of the target protein, peptide or fragment thereof is then detected by antibodies specific to the target protein, peptide or fragment thereof, which are in turn detected by antibody binding reagents. Antibody binding reagents may be, for example, protein A, or other antibodies. Antibody binding reagents may be radiolabelled or enzyme linked as described hereinabove. Detection may be by autoradiography, colorimetric reaction or chemiluminescence. This method allows both quantitation of an amount of target protein, peptide or fragment thereof and determination of its identity by a relative position on the membrane which is indicative of a migration distance in the acrylamide gel during electrophoresis.

Radio-immunoassay (RIA): In one version, this method involves precipitation of the desired target protein, peptide or fragment thereof with a specific antibody and radiolabelled antibody binding protein (e.g., protein A labelled with $I^{125}$) immobilized on a precipitable carrier such as agarose beads. The number of counts in the precipitated pellet is proportional to the amount of target protein, peptide or fragment thereof.

In an alternate version of the RIA, a labelled target protein, peptide or fragment thereof and an unlabelled antibody binding protein are employed. A sample containing an unknown amount of a target protein, peptide or fragment thereof is added in varying amounts. The decrease in precipitated counts from the labelled target protein, peptide or fragment thereof is proportional to the amount of target protein, peptide or fragment thereof in the added sample.

Fluorescence activated cell sorting (FACS): This method involves detection of a target protein, peptide or fragment thereof in situ in cells by target protein, peptide or fragment thereof specific antibodies. The target protein, peptide or fragment thereof specific antibodies are linked to fluorophores. Detection is by means of a cell sorting machine which reads the wavelength of light emitted from each cell as it passes through a light beam. This method may employ two or more antibodies simultaneously.

Immunohistochemical analysis: This method involves detection of a target protein, peptide or fragment thereof in situ in fixed cells by target protein, peptide or fragment thereof specific antibodies. The target protein, peptide or fragment thereof specific antibodies may be enzyme linked or linked to fluorophores. Detection is by microscopy and subjective or automatic evaluation. If enzyme linked antibodies are employed, a colorimetric reaction may be required. It will be appreciated that immunohistochemistry is often followed by counterstaining of the cell nuclei using for example Hematoxyline or Giemsa stain.

In situ activity assay: According to this method, a chromogenic substrate is applied on the cells containing an active enzyme and the enzyme catalyzes a reaction in which the substrate is decomposed to produce a chromogenic product visible by a light or a fluorescent microscope.

In vitro activity assays: In these methods the activity of a particular enzyme is measured in a protein mixture extracted from the cells. The activity can be measured in a spectrophotometer well using colorimetric methods or can be measured in a non-denaturing acrylamide gel (i.e., activity gel). Following electrophoresis the gel is soaked in a solution containing a substrate and colorimetric reagents. The resulting stained band corresponds to the enzymatic activity of the protein of interest. If well calibrated and within the linear range of response, the amount of enzyme present in the sample is proportional to the amount of colour produced. An enzyme standard is generally employed to improve quantitative accuracy.

In addition, the amount of bacterial DNA may be determined by quantitative PCR as an indicator of the presence of or level of micro-organisms in an oral tissue.

The presence of or level of a protein or DNA from *Porphyromonas gingivalis, Treponema denticola, Tannerella forsythia* may be determined and indicative that substantially all micro-organisms or fragments thereof have been removed from an oral tissue of a subject.

The anti-microbial agent and/or immunogen may be administered systemically, or directly to oral tissue, especially directly to oral mucosa.

In one embodiment, the treatment of the subject removes substantially all micro-organisms or fragments thereof from oral tissue of said subject, thereby minimising inflammation in the oral tissue of the subject. In another embodiment, the treatment of the subject removes substantially all micro-organisms or fragments thereof from oral tissue of said subject, thereby minimising immune responses in the oral tissue of the subject.

The immunogen may be administered to said subject after treatment of said subject to remove substantially all micro-organisms and fragments thereof from oral tissue of said subject.

Generally, in accordance with the invention, the relevant oral tissue is not inflamed, or inflammation, if present at all is asymptomatic or sub clinical at the time of immunisation.

After immunisation the subject exhibits a predominance of a Th2 response which is largely a humoral response and the individual has detectable levels of protective antibodies.

3. COMPOSITIONS

In certain embodiments there is provided a composition including:
  anti-microbial agent for removing substantially all micro-organisms and fragments thereof from oral tissue of said subject;
  an immunogen for immunising said subject against a microbial pathogen, the presence of which in oral tissue is associated with a disease or condition;
  said composition capable of being used in a method described above.

3. (a) Anti-Microbial Agents

The anti-microbial agent may be any agent that, the effect of which on administration is to deplete inflammatory stimuli. These agents used alone or in combination have utility in the short term inhibition of inflammation, periodontal pathogen re-emergence, for example biofilm formation, and/or periodontal bone resorption. These agents alone or combination can be applied, for example, topically in a slow-release, periodontal gel formulation at a periodontal site, that may have undergone surgical intervention, to prepare the patient's immune system for vaccination against the periodontal pathogens.

Without being bound by any theory or mode of action, it is believed that application of an anti-microbial agent as defined herein, for example in a periodontal gel formulation, at the time of mechanical debridement and cleaning of the infected periodontal site, helps prepare the immune system to allow the development of a Th2-biased response. This Th2-biased response results in the production of protective antibodies and the prevention of the re-emergence of the periodontal pathogens and prevention of disease progression.

In this context, the following may be anti-microbial agents: an antibiotic, an immunosuppressant and an antiseptic. In certain embodiments the agent may be an anti-inflammatory agent. Anti-inflammatory agents include Nonsteroidal Anti-inflammatory Drugs (NSAIDs). Examples of NSAIDs include compounds than inhibit a cyclooxygenase. Specific examples of NSAIDs include aspirin, ibuprofen and naproxen. Other examples of ant-inflammatory agents include antagonists of PAR-2 which include, but are not limited to, antibodies and antibody fragments that bind PAR-2, other polypeptides that bind to PAR-2 and inhibit its activity, other compounds that inhibit PAR-2 activity or expression including small organic compounds and inhibitory nucleic acids that interact with PAR-2 encoding nucleic acids. Exemplary antagonists that may block or displace an endogenous ligand from binding PAR-2 and/or signalling via PAR-2 include those described in WO 2004/002418 and WO 2006/023844 (e.g. peptides having the amino acid sequence LICK (SEQ ID NO: 91) or LIGKV (SEQ ID NO: 92)). Antagonists that bind to PAR-2 and prevent proteolytic cleavage of the region of PAR-2 that acts as a tethered ligand are exemplified in WO 2007/092640.

Antagonists that inhibit, reduce or block expression of PAR-2 include inhibitory nucleic acids, including, but not limited to, ribozymes, triplex-forming oligonucleotides (TFOs), external guide sequences (EGSs) that promote cleavage by RNase P, peptide nucleic acids, antisense DNA, siRNA, and microRNA specific for nucleic acids encoding PAR-2.

PAR-2 may be inhibited indirectly by "indirect antagonists" that antagonise the activity of proteases which under normal circumstances cleave PAR-2 resulting in its activation. Proteases which can cleave PAR-2 include gingipains, trypsins, tryptases and neutrophil proteinase-3. Examples of indirect antagonists that are useful in a method of the invention or that can be used in a composition of the invention include trypsin inhibitors disclosed in WO 93/14779 and tryptase inhibitors disclosed in WO 02/47762.

In one particularly preferred embodiment, the anti-microbial agent is an antibiotic. Examples include antibiotics selected from the group consisting of macrolides, tetracyclines, penicillins, fumarate reductase inhibitors and anti-microbial peptides, as shown in TABLE B below.

TABLE B

| Antiinfective | Drug | Trade name in Australia (Sponsor) |
|---|---|---|
| Macrolides | Roxithromycin | Biaxsig (Sanofi-Aventis) |
| | | Roxar (Sigma) |
| | | Roxide (Sandoz) |
| | | Roximycin (Alphapharm) |
| | | Roxithromycin-RL (Real-RL) |
| | | Rulide and Rulie D (Sanofi-Aventis) |
| | Metronidazole | Flagyl (Sanofi-Aventis) |
| | | Flagyl S Suspension (Sanofi-Aventis) |
| | | Metrogyl (Alphapharm) |
| | | Metronidazole Gel (Orion) |
| | | Metronide (Sanofi-Aventis) |
| | | Rozex (cream and gel forms) (Galderma) |
| | Erthromycin | DBL Erythromycin (Hospira) |
| | | EES (Link) |
| | | E-Mycin (Alphpharm) |
| | | Eryc Capsules (Mayne Pharma International) |
| | Clindamycin | Cleocin (Pfizer) |
| | | Dalacin C Capsules (Pfizer) |
| | | Duac Once Daily Gel (Stiefel) |
| | | Zindaclin (Genepharm) |
| | Spiramycin | Rovamycine |
| Tetracyclines | Minocycline | Akamin (Alphapharm) |
| | Doxycyline | Doryx (Mayne Pharma International) |
| | | Doxsig (Sigma) |
| | | Doxy Tablets (Genepharm) |
| | | Doxyhexal tablets (Sandoz) |
| | | Doxylin (Alphapharm) |
| | | Frakas (Sigma) |
| | | GenRX Doxycycline Capsules (Apotex) |
| | | GenRX Doxycycline Tablets (Apotex) |
| | | Vibramycin (Pfizer) |
| Antiseptic | Chlorhexidine hydrochloride | Savlon Antiseptic (Reckitt Benckiser) |
| | Chlorhexidine gluconate | Chlorhexidine and Cetrimide Aqueous Irrigations (Pfizer) |
| | | Chlorhexidine Irrigation Solution (Pfizer) |
| | | Difflam-C Anti-inflammatory Antiseptic Solution (iNova) |
| | | Lignocaine 2% Gel with Chlorhexidine 0.05% (Pfizer) |
| | | Microshield 2 (J & J Medical) |
| | | Microshield 4 (J & J Medical) |
| | | Microshield 5 (J & J Medical) |
| | | Microshield Tincture (J & J Medical) |
| | | Plaqacide Mouthrinse (Oral-B) |

TABLE B-continued

| Antiinfective | Drug | Trade name in Australia (Sponsor) |
| --- | --- | --- |
| Penicillins | Penicillin G | BenPen (CSL) |
| | Penicillin V | Abbocillin V, Abbocillin VK (Sigma) |
| | | Cilicaine VK, Cilicaine V (Fawns & McAllen) |
| | | Cilopen VK (Genepharm) |
| | | LPV (Aspen) |
| | | Penhexal VK (Hexal) |
| | Ampicillin | Administered as an intramuscular or intravenous injection |
| | Amoxycillin | Amoxycillin Sandoz Capsules and Suspension (Sandoz) |
| | | Amoxycillin Sandoz Tablets (Sandoz) |
| | | Alphamox (Alphapharm) |
| | | Amohexal Capsules (Hexal) |
| | | Amohexal Syrup (Hexal) |
| | | Amoxil Duo (GlaxoSmithKline) |
| | | Amoxil Oral (GlaxoSmithKline) |
| | | Augmentin (GlaxoSmithKline) |
| | | Augmentin Duo, Augmentin Duo Forte Tablets (GlaxoSmithKline) |
| | | Amoxycillin-DP (Genepharm) |
| | | APO-Amoxicillin Capsules (Apotex) |
| | | Bgramin (Genepharm) |
| | | Chemmart Amoxycillin Capsules (Apotex) |
| | | Cilamox (Sigma) |
| | | Clamoxyl 125/31.25 (Alphapharm) |
| | | Clamoxyl Duo 500/125, Clamoxyl Duo Forte 875/125 (Alphapharm) |
| | | Clavulin 125 Syrup (Menley & James) |
| | | Clavulin Duo 500/125 and Clavulin Duo Forte Tablets (Menley & James) |
| | | Curam (Sandoz) |
| | | GA-Amclav 500/125, GA-Amclav Forte 875/125 Tablets (Genepharm) |
| | | GenRx Amoxycillin and Clavulanic Acid 875 mg/125 mg (Apotex) |
| | | Klacid Hp 7 (Abbott) |
| | | Maxamox (Sandoz) |
| | | Maxamox Powder for Oral Suspension (Sandoz) |
| | | Moxacin Oral Preparations (Sandoz) |
| | | Nexium Hp7 (AstraZeneca) |
| | | Ranmoxy (Ranbaxy) |
| | | Terry White Chemists Amoxycillin Capsules (Apotex) |
| | | Terry White Chemists Amoxycillin Suspension (Apotex) |
| Cephalosporins | Cephalexin | Cefalexin Sandoz (Sandoz) |
| | | Ialex (Lennon) |
| | | Ibilex (Alphapharm) |
| | | Keflex (Aspen) |
| | | Rancef (Ranbaxy) |
| | | Sporahexal (Sandoz) |
| | | Terry White Chemists Cephalexin (Apotex) |

In one embodiment, the anti-microbial agent is selected from one or more of inhibiting agents of fumarate reductase. Suitable inhibiting agents include natural products, that include but are not limited to decursin, verticipyrone, paecilaminol, 5-alkenyl-3,3(2H)-furanones from *Streptomyces* spp., nafuredin, mesaconic acid, rotenone, and natural, semi-synthetic and synthetic analogues thereof. In another aspect, inhibiting agents may be synthetic compounds that include but are not limited to; 2-substituted 4,6-dinitrophenols; mercaptopyridine N-oxide; L-092,201 (Merck Sharpe and Dohme); nitro-imidazoles such as fexindazole megazol benznidazole, MK-436, L-634,549, misonidazole; or benzimidazoles such as albendazole, cambendazole mebendazole, oxfendazole, parebendazole and thiabendazole; or oxantel or morantel. Preferred inhibiting agents are oxantel, morantel or thiabendazole. A particularly preferred inhibiting agent is oxantel.

It will be recognised by the skilled addressee that the selection of the inhibiting agent will be dependent upon number of clinical factors which determine whether the inhibiting agent is appropriate for use in a clinical setting.

The antibiotic may be directly cytotoxic to the microbial pathogen. In other embodiments, the antibiotic is indirectly cytotoxic, for example, the antibiotic may be an inhibitor of microbial biofilm production or some other metabolism.

In one embodiment, the antibiotic is an anti-microbial peptide. Examples are shown in Table C below.

targeting *Porphyromonas gingivalis* are those directed to the active site of the Kgp and RgpA proteinases and those directed to binding motifs in the A1 adhesin of the Kgp and RgpA proteinases.

In one embodiment, the anti-microbial is an antibody mimetic. The antibody mimetic may or may not have the tertiary structure of an immunoglobulin domain (e.g. Dimitrov, 2009, MAbs 1 26-28). An antibody mimetic may have specificity for binding to a specific molecule. One example of an antibody mimetic is the family of molecules related to human lipocalins, known as anticalins (e.g. Skerra, 2007 Current Opinions in Biotechnology, 18 295-304). Preferably, an anticalin is directed to, or binds specifically to, a protein from *Porphyromonas gingivalis*. In a preferred embodiment, the anticalin is directed to, or binds specifically to, an active site of a Lys-X-proteinase or Arg-X-proteinase, such as Kgp and RgpA proteinases. Anticalins can be used in lieu of monoclonal antibodies, but are about eight times smaller with a size of about 180 amino acids and a mass of about 20 kDa. Anticalins have better tissue penetration than antibodies and are stable at temperatures up to 70° C. Unlike antibodies, they can be produced in bacterial cells like *E. coli* in large amounts.

In certain embodiments the anti-microbial agent may also be an anti-biofilm agent that can inhibit, reduce or prevent bacterial biofilm formation or development. An anti-biofilm agent may have biofilm disrupting activity and may cause biofilm dispersion. "Biofilm disrupting activity" is used

TABLE C

| Anti-microbial agent | Exemplary reference |
| --- | --- |
| Peptide including $\alpha_{S1}$-casein(11-23) (SEQ ID NO: 86) | — |
| Peptide including β-casein(193-209) (SEQ ID NO: 87) | — |
| Peptide including κ-casein(109-137) (SEQ ID NO: 88) | — |
| Peptide including β-casein(193-205) (SEQ ID NO: 89) | — |
| Peptide including κ-casein(117-137) (SEQ ID NO: 90) | — |
| Non-glycosylated peptides, for example, derived from κ-casein | PCT/AU98/00972 (see, for example, Table 1) |
| Composition, for example, including a peptide derived from κ-casein and a divalent cation | PCT/AU2004/001764 |
| Peptides, for example, derived from κ-casein | Glycosylated versions of peptides in PCT/AU98/00972, including those peptides in a composition with a divalent cation |
| Agent to inhibit a *P. gingivalis* polypeptide | PCT/AU2008/001017 (see, for example, an inhibitor of fumarate reductase e.g. oxantel, morantel or thiabendazole) |

In one particularly preferred embodiment, the anti-microbial agent is an inhibitor of microbial biofilm production. Other preferred agents are fumarate reductase inhibitors.

In certain embodiments, the anti-microbial agent may be an antibody. The antibody may be a polyclonal or monoclonal antibody. Exemplary monoclonal antibodies that may be used are directed to molecules of the periodontal pathogens (e.g proteases and adhesins) or host to dampen inflammation [e.g. antibodies, singly or in combination, against tumor necrosis factor (TNFα), interleukin-1 (1L-1), urokinase-type plasminogen activator (u-PA), granulocyte macrophage colony stimulating factor (GM-CSF), macrophage colony stimulating factor (M-CSF) and RANK ligand (RANKL)]. Preferably the antibody is a mixture of monoclonal antibodies directed against different pathogen antigens and host inflammatory mediators. The preferred monoclonal antibodies to be used herein to describe the property of a composition or agent that causes the release of bacteria from the biofilm. The composition or agent may also but not necessarily, reduce the viability of a bacterium in a biofilm. "Release" of bacteria from the biofilm includes increasing the number of bacteria from a biofilm to adopt a planktonic state thereby increasing the susceptibility of a bacterium from a biofilm to bactericidal agents. A bactericidal agent is used herein to describe the property of a composition, agent, compound, peptidomimetic or peptide that directly reduces the viability of a bacterium.

Accordingly, without being bound by any theory, or mode of action, it is believed that compositions or agents that exhibit biofilm disrupting activity do not necessarily reduce the viability of bacteria in a biofilm but instead cause or induce the bacterial cells to be released from the biofilm. In certain embodiments these compositions or agents may cause or induce more of the bacteria in a biofilm to adopt a planktonic state. In other embodiments, the compositions or agents may inhibit or reduce the formation of a biofilm. In certain embodiments, the compositions or agents may inhibit or reduce biofilm growth. In other embodiments, the anti-microbial agents of the invention may inhibit or reduce any characteristic that a biofilm exhibits which initiates or promotes a disease or condition in a subject. In certain embodiments, the peptides or compositions may inhibit or reduce any characteristic that a biofilm exhibits which initiates or promotes a disease or condition in a subject, without killing the bacteria in the biofilm.

In certain embodiments, an anti-microbial composition or agent refers to the ability to prevent, inhibit or reduce a measurable parameter of a biofilm. Non-limiting examples of measurable parameters of a biofilm may be total biomass, average thickness, surface to biovolume ratio, roughness coefficient or bacterial composition and their viability of the biofilm.

3. (b) Immunogens

The immunogen is selected to invoke an immune response, preferably a protective antibody response to the microbial pathogen of concern.

In one embodiment, the immunogen is provided in the form of a peptide, for example a recombinant peptide.

In one embodiment particularly related to *P. gingivalis* infection and associated disease and conditions, the recombinant peptide may be a chimeric or fusion protein for inducing an immune response to *P. gingivalis*, the protein including a first peptide joined directly or through a linker to a second peptide, wherein:
  (A) said first peptide includes:
    (i) part of, or all of a sequence that is the same as, or homologous to the sequence shown in SEQ ID No:1; or
    (ii) part of, or all of a sequence that is the same as, or homologous to the sequence shown in SEQ ID No:2; and
  (B) said second peptide includes:
    (i) part of, or all of a sequence that is the same as, or homologous to the sequence of an adhesin domain of the Lys-X-proteinase of *P. gingivalis*; or
    (ii) part of, or all of a sequence that is the same as, or homologous to the sequence of an adhesin domain of the Arg-X-proteinase of *P. gingivalis*; or
    (iii) part of, or all of a sequence that is the same as, or homologous to the sequence of a HagA adhesin domain of *P. gingivalis*.

As used herein, the term "peptide" is used to refer to an amino acid sequence of up to about 40 amino acid residues, preferably from 5 to 40 amino acid residues.

In one embodiment, a polypeptide is used in place of or in other words instead of the "second peptide". The term "polypeptide" is used to refer to an amino acid sequence of at least about 40 amino acid residues.

Thus, in another aspect there is provided a chimeric or fusion protein for inducing an immune response to *P. gingivalis*, the protein including a peptide joined directly or through a linker to a polypeptide, wherein:
  (A) said peptide includes:
    (i) part of, or all of a sequence that is the same as, or homologous to the sequence shown in SEQ ID No:1; or
    (ii) part of, or all of a sequence that is the same as, or homologous to the sequence shown in SEQ ID No:2; and
  (B) said polypeptide includes:
    (i) part of, or all of a sequence that is the same as, or homologous to the sequence of an adhesin domain of the Lys-X-proteinase of *P. gingivalis*; or
    (ii) part of, or all of a sequence that is the same as, or homologous to the sequence of an adhesin domain of the Arg-X-proteinase of *P. gingivalis*; or
    (iii) part of, or all of a sequence that is the same as, or homologous to the sequence of a HagA adhesin domain of *P. gingivalis*.

In another aspect, the invention provides a peptide for inducing an immune response to *P. gingivalis* selected from the group consisting of:
  (i) a sequence that is the same as or homologous to the sequence shown in one of SEQ ID No: 64 to 66; and
  (ii) a sequence that is the same as or homologous to the sequence shown in SEQ ID No: 67 or 68.

In an aspect of the invention, where the peptide has a sequence of SEQ ID No: 64 to 68, the peptide may be provided in the form of a chimeric or fusion protein in which the peptide is joined directly or through a linker to a second peptide. In an embodiment, the second peptide of the chimeric or fusion protein includes:
  (i) part of, or all of a sequence that is the same as, or homologous to the sequence of an adhesin domain of the Lys-X-proteinase of *P. gingivalis*; or
  (ii) part of, or all of a sequence that is the same as, or homologous to the sequence of an adhesin domain of the Arg-X-proteinase of *P. gingivalis*; or
  (iii) part of, or all of a sequence that is the same as, or homologous to the sequence of a HagA adhesin domain of *P. gingivalis*.

In the above described embodiment a polypeptide is used in place of, or in other words instead of the second peptide. Thus, in another aspect there is provided a chimeric or fusion protein for inducing an immune response to *P. gingivalis*, the protein including a peptide joined directly or through a linker to a polypeptide, wherein:
  (A) said peptide includes:
    (i) a sequence that is the same as or homologous to the sequence shown in one of SEQ ID No: 64 to 66; or
    (ii) a sequence that is the same as or homologous to the sequence shown in SEQ ID No: 67 or 68; and
  (B) said polypeptide includes:
    (i) part of, or all of a sequence that is the same as, or homologous to the sequence of an adhesin domain of the Lys-X-proteinase of *P. gingivalis*; or
    (ii) part of, or all of a sequence that is the same as, or homologous to the sequence of an adhesin domain of the Arg-X-proteinase of *P. gingivalis*; or
    (iii) part of, or all of a sequence that is the same as, or homologous to the sequence of a HagA adhesin domain of *P. gingivalis*.

As used herein, a reference to a "homologue" of a peptide or polypeptide is a reference to a peptide or polypeptide having an amino acid sequence that shares homology or that is homologous to, or that has identity with the amino acid sequence of the first-mentioned peptide or polypeptide, preferably at least 90% sequence identity, more preferably at least 95% and even more preferably at least 98% sequence identity when the comparison is performed by a BLAST algorithm wherein the parameters of the algorithm are selected to give the largest match between the respective sequences over the entire length of the respective reference sequences. Sequence identity refers to exact matches between the amino acids of two sequences which are being compared. Such a homologue may derive from a naturally occurring variant or isolate of the Lys-X-proteinase or Arg-X-proteinase of *P. gingivalis*. Alternatively, it may be a "conservative-substitution" variant of a peptide or polypeptide from the Lys-X-proteinase or Arg-X-proteinase of *P. gingivalis* in which one or more amino acid residues have been changed without altering the overall conformation and function of the peptide or polypeptide; including, but by no means limited to, replacement of an amino acid with one having similar properties. Amino acids with similar properties are well known in the art. For example, polar/hydrophilic amino acids which may be interchangeable include asparagine, glutamine, serine, cysteine, threonine, lysine, arginine, histidine, aspartic acid and glutamic acid; nonpolar/hydrophobic amino acids which may be interchangeable include glycine, alanine, valine, leucine, isoleucine, proline, tyrosine, phenylalanine, tryptophan and methionine; acidic amino acids which may be interchangeable include aspartic acid and glutamic acid and basic amino acids which may be interchangeable include histidine, lysine and arginine. Preferably such conservative-substitution variants have less than 20, more preferably less than 15, more preferably less than 10, and most preferably less than 5 amino acid changes.

Figure 7:
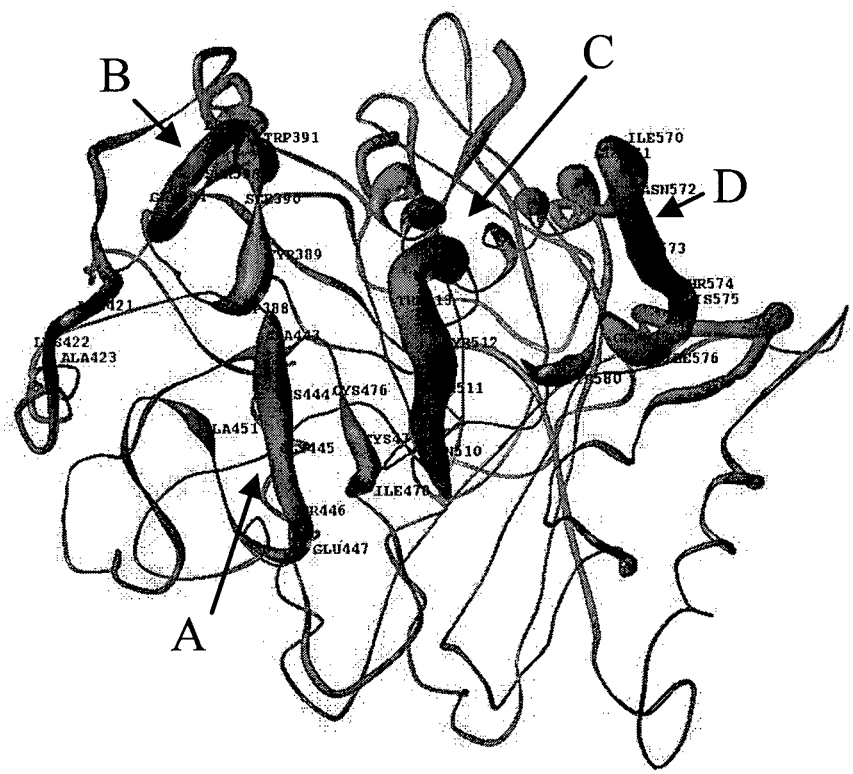
FIG. 7. Protein model of the Kgp proteinase. KAS2 [Asn433-Lys468]. (A) KAS4 [Asp388-Val395] (B), KAS5 [Asn510-Asp516] (C) and KAS6 [Ile570-Tyr580] (D).

A region of a *P. gingivalis* trypsin-like enzyme—especially a Lys-X-proteinase (Kgp) or Arg-X-proteinase (RgpA)—that defines a site in an enzyme for cleavage of a peptide bond can be determined following the teaching of the specification herein, particularly in relation to FIG. 7 and Example 9, which exemplify the process for predicting three-dimensional conformation of the catalytic site as it appears on *P. gingivalis* for Lys-X-proteinase. Example 10 provides methodology for modelling of the Arg-X-proteinase three-dimensional conformation.

In certain embodiments, the chimeric or fusion protein, or first or second peptide components thereof may be formed from a peptidomimetic. A peptidomimetic is a molecule that mimics one or more characteristics of a given peptide, for example conformation, and that consists of amino acid residues, some of which may not be naturally occurring.

Having identified the immunogenic regions of the catalytic site, the inventors have determined the sequence of various peptide immunogens against which a humoral response can be raised. In particular, 'six' regions that flank or otherwise define the catalytic site have been defined as follows: KAS1/RAS1, KAS2/RAS2, KAS3/RAS3, KAS4/RAS4, KAS5/RAS5 and KAS6 (see Table 1). With this information, the inventors have been able to interrogate protein sequence databases to determine peptides that share homology with amino acid sequences that form regions that flank a catalytic site and hence that represent immunogenic epitopes found on *P. gingivalis*. The sequence of these peptides are identified by the following structural formula:

TABLE 1

Sequences that flank the active site of Kgp and RgpA.

| Region | Kgp Lys - X (numbering according to SEQ ID No. 62) | Kgp Lys - X Consensus | RgpA Arg - X (numbering according to SEQ ID No. 61) | RgpA Arg - X Consensus |
|---|---|---|---|---|
| PAS1K/PAS1R | PAS1K (432-453) | LNTGVSFANYTAHGSETAWADP (SEQ ID NO: 30) | PAS1R (426-446) | FNGGISLANYTGHGSETAWGT (SEQ ID NO: 34) |
| KAS1/RAS1 | KAS1 (432-454) | LNTGV[G/S]FANYTAHGSET[S/A]WADP[S/L] (SEQ ID NO: 27) | RAS1 (426-448) | FNGGISL[V/A]NYTGHGSETAWGTSH (SEQ ID NO: 31) |
| KAS2/RAS2 | KAS2 (433-468) | NTGV[G/S]FANYTAHGSET[S/A]WADP[S/L][L/V]T[A/T][T/S]Q[V/L]KALTNK[D/N]K (SEQ ID NO: 28) | RAS2 (427-462) | NGGISL[V/A]NYTGHGSETAWGTSHFGTTHVKQLTNSNQ (SEQ ID NO: 32) |
| KAS3/RAS3 | KAS3 (436-455) | V[G/S]FANYTAHGSET[S/A]WADP[S/L][L/V] (SEQ ID NO: 29) | RAS3 (430-449) | ISL[V/A]NYTGHGSETAWGTSHF (SEQ ID NO: 33) |
| KAS4/RAS4 | KAS4 (388-395) | D[S/Y][Y/S]WN[P/S][K/Q][I/V] (SEQ ID NO: 64) | RAS4 (379-386) | EGGPSADN (SEQ ID NO: 67) |
| KAS5/RAS5 | KAS5 (510-516) | NSYWGED (SEQ ID NO: 65) | RAS5 (508-514) | [N/D]Q[S/Y]WA[S/P]P (SEQ ID NO: 68) |
| KAS6 | KAS6 (570-580) | IGN[V/I]THIGAHY (SEQ ID NO: 66) | | |

The inventors have found that chimeric proteins including these peptides have a number of utilities. For example, as described herein, some produce a humoral response that is highly protective for treatment or prevention of bone loss as observed in chronic periodontitis. The peptides may also be used in a diagnostic assay wherein they can detect or monitor specificities in an individual's serum, thereby indicating whether or not the individual is infected and if so, whether treatments are required or if provided, whether they have been effective.

It will be understood that the region of a *P. gingivalis* trypsin-like enzyme that defines a site in the enzyme for cleavage of a peptide bond located C-terminal to Lys or Arg, does not comprise a complete sequence of the Lys-X-proteinase or Arg-X-proteinase.

As used herein, the terms "heterologous protein" or "chimeric or fusion protein" are used to refer to a protein that is composed of functional units, domains, sequences or regions of amino acids derived from different sources or that are derived from the same source and that have been assembled so as to have an organisation that is distinguished from that observed in a molecule from which the unit, domain, sequence or region is derived or related to. A common feature of the chimeric or fusion proteins of the invention is that they contain at least one peptide having an amino acid sequence that is the same as or that shares homology with a sequence of a *P. gingivalis* trypsin-like enzyme that defines a catalytic site for cleavage of a peptide bond.

In a preferred embodiment, where the first peptide comprises a peptide from the Kgp[432-468] region, it is preferably (i) a peptide which comprises a sequence selected from VSFANYT (SEQ ID NO: 3) and VGFANYT (SEQ ID NO: 4), more preferably a sequence selected from GVSFANYT (SEQ ID NO: 5), GVGFANYT (SEQ ID NO: 6), VSFANYTA (SEQ ID NO: 7) and VGFANYTA (SEQ ID NO: 8); or (ii) a peptide which comprises a sequence selected from ETAWAD (SEQ ID NO: 9), ETSWAD (SEQ ID NO: 10), TAWADP (SEQ ID NO: 11) and TSWADP (SEQ ID NO: 12), preferably a sequence selected from SETAWAD (SEQ ID NO: 13), SETSWAD (SEQ ID NO: 14), ETAWADP (SEQ ID NO: 15), ETSWADP (SEQ ID NO: 16), TAWADPL (SEQ ID NO: 17) and TSWADPL (SEQ ID NO: 18), more preferably a sequence selected from GSETAWAD (SEQ ID NO: 19), GSETSWAD (SEQ ID NO: 20), SETAWADP (SEQ ID NO: 21), SETSWADP (SEQ ID NO: 22), ETAWADPL (SEQ ID NO: 23), ETSWADPL (SEQ ID NO: 24), TAWADPLL (SEQ ID NO: 25) and TSWADPLL (SEQ ID NO: 26). More preferably, this peptide is selected from the KAS1 [432-454], KAS2[433-468] and KAS3[436-455] peptides shown in Table 1. Alternatively, the first peptide may be the PAS1 K[432-453] peptide, also known as PAS1(K48), disclosed in International Patent Application No. PCT/AU98/00311 (WO 98/049192). The sequence identifiers corresponding to these peptides are shown in Table 3.

Similarly, in another preferred embodiment, where the first peptide comprises a peptide from the RgpA[426-462] region, this peptide is preferably selected from the RAS1[426-448], RAS2[427-462] and RAS3[430-449] peptides shown in Table 1. Alternatively, the first peptide may be the PAS1R [426-446] peptide, also known as PAS1(R45), disclosed in International Patent Application No. PCT/AU98/00311 (WO 98/049192).

In the chimeric or fusion protein of the invention, the second peptide may be a peptide from an adhesin domain of a *P. gingivalis* trypsin-like enzyme, such as Lys-X-proteinase (Kgp) or Arg-X-proteinase (RgpA) or HagA (see Table 2). These domains are sometimes also known as hemagglutinins. In the Lys-X-proteinase, the preferred domains are KA1, KA2, KA3, KA4, KA5 as identified in Table 2. In the Arg-X-proteinase, the preferred domains are RA1, RA2, RA3 and RA4 as identified in Table 2. In HagA, the preferred domains are HagA1, HagA1* and HagA1**.

TABLE 2

Adhesin domains of the Kgp and RgpA proteinases.

| | A1 | sA1 | LA1 | A2 | A3 | A4 | A5 |
|---|---|---|---|---|---|---|---|
| Kgp Lys-X proteinase SEQ ID No. 62 | KA1 (738-1099) SEQ ID NO: 35 | KsA1 (759-989) SEQ ID NO: 36 | KLA1 (751-1056) SEQ ID NO: 37 | KA2 (1157-1275) SEQ ID NO: 40 | KA3 (1292-1424) SEQ ID NO: 41 | KA4 (1427-1546) SEQ ID NO: 42 | KA5 (1548-1732) SEQ ID NO: 43 |
| RgpA Arg-X proteinase SEQ ID No. 61 | RA1 (720-1081) SEQ ID NO: 38 | RsA1 (831-971) SEQ ID NO: 39 | — | RA2 (1139-1257) SEQ ID NO: 44 | RA3 (1274-1404) SEQ ID NO: 45 | RA4 (1432-1706) SEQ ID NO: 46 | — |
| HagA SEQ ID NO. 63 | HagA1 (26-351) (SEQ ID NO: 80), HagA1* (366-625) (SEQ ID NO: 81), HagA1** (820-1077) (SEQ ID NO: 82) or HagA1** (1272-1529) (SEQ ID NO: 82) | | | | | | |

In addition to improving the humoral response to a peptide of the invention such as KAS1, KAS2, KAS3, KAS4, KAS5 and KAS6 or RAS1, RAS2 and RAS3, RAS4 and RAS5 when included with such a peptide in a chimeric or fusion protein, the adhesin domain also contains immunogenic epitopes, hence leading to the production of multiple specificities to elicit a protective immunogenic response. The finding that the immunogenic epitopes of the adhesin domain are retained in a form approaching that in a *P. gingivalis* trypsin-like enzyme when provided in the chimeric or fusion protein of the invention is unanticipated.

It will be understood that in these embodiments of the invention the chimeric or fusion protein may contain any one or more of the peptides selected from KAS1/RAS1, KAS2/RAS2, KAS3/RAS3, KAS4/RAS4, KAS5/RAS5 and KAS6/RAS6 together with any one or more adhesin domains of a *P. gingivalis* trypsin-like enzyme, in particular with any one or more of Lys-X-proteinase adhesin domains (KA1, KA2, KA3, KA4 and KA5) or Arg-X-proteinase adhesin domains (RA1, RA2, RA3 and RA4) or HagA domains HagA1, HagA1* and HagA1**.

It will also be understood that it is not necessary for the adhesin domain to be a complete domain as observed in a *P. gingivalis* trypsin-like enzyme. For example the adhesin domain may be a fragment of such a domain, in particular, preferred fragments are the KsA1 and KLA1 domain fragments of the Lys-X-proteinase A1 domain (see Table 2). Where the domain is a fragment of an adhesin domain it generally contains one or more adhesin domain specific epitopes.

The sequence identifiers corresponding to the adhesin related peptides are shown in Table 3.

In one embodiment the second peptide or polypeptide includes a sequence shown in one or more of SEQ ID No: 69 to 79 or one or more of 83 to 85.

The chimeric or fusion protein of the present invention may also include one or more additional peptides selected from the Kgp[432-468] region of the Lys-X-proteinase and/or one or more additional peptides selected from the RgpA[426-462] region of the Arg-X-proteinase.

In preferred embodiments of the present invention, the chimeric or fusion protein includes one or more of KAS1, KAS2, KAS3, KAS4, KAS5 and KAS6, or one or more of RAS1, RAS2, RAS3, RAS4 and RAS5, together with KsA1 or KLA1.

Thus in certain embodiments, the chimeric or fusion protein may include at least one further peptide wherein said further peptide includes:

(i) part of, or all of a sequence that is the same as, or homologous to the sequence shown in SEQ ID No:1; or (ii) part of, or all of a sequence that is the same as, or homologous to the sequence shown in SEQ ID No:2; or (iii) part of, or all of a sequence that is the same as, or homologous to the sequence of an adhesin domain of the Lys-X-proteinase of *P. gingivalis*; or (iv) part of, or all of a sequence that is the same as, or homologous to the sequence of an adhesin domain of the Arg-X-proteinase of *P. gingivalis*; or (v) part of, or all of a sequence that is the same as, or homologous to the sequence of a HagA adhesin domain of *P. gingivalis*.

Other examples of domains, units, sequences or regions that may be included in a chimeric or fusion protein as described herein include domains for binding to receptors or ligands such as Fc binding regions or Fc receptors, domains for improving half-life such as albumin or domains for facilitating expression or purification of the chimeric or fusion protein.

In yet another aspect, the invention provides a peptide for inducing an immune response to *P. gingivalis* including the sequence shown in one of SEQ ID No: 17, 18, 25 and 26. In one embodiment, the peptide has a sequence that is homologous to one of SEQ ID No: 17, 18, 25 and 26. The peptide may have a length of 5 to 40 amino acids.

In yet another aspect, the invention provides a nucleic acid encoding a peptide having a sequence shown in one of SEQ ID No: 17, 18, 25 and 26.

In yet another aspect, the invention provides a use of a peptide having a sequence shown in one of SEQ ID No: 17, 18, 25 and 26, or a nucleic acid encoding a peptide having a sequence shown in one of SEQ ID No: 17, 18, 25 and 26, for the manufacture of a chimeric or fusion protein for inducing an immune response to *P. gingivalis*.

In yet another aspect, the invention provides a use of a peptide having a sequence shown in one of SEQ ID No: 17, 18, 25 and 26, or a nucleic acid encoding a peptide having a sequence shown in one of SEQ ID No: 17, 18, 25 and 26, for inducing an immune response to *P. gingivalis*. In one embodiment, the peptide is administered simultaneously or sequentially with a second peptide including:

(i) part of, or all of a sequence that is the same as, or homologous to the sequence of an adhesin domain of the Lys-X-proteinase of *P. gingivalis*; or (ii) part of, or all of a sequence that is the same as, or homologous to the sequence of an adhesin domain of the Arg-X-proteinase of *P. gingivalis*; or (iii) part of, or all of a sequence that is the same as, or homologous to the sequence of a HagA adhesin domain of *P. gingivalis*.

TABLE 3

| SEQ ID NO: | Amino acid sequence | Fragment |
| --- | --- | --- |
| 1 | LNTGV[G/S]FANYTAHGSET[S/A]WADP[S/L][L/V]T[A/T][T/S]Q[V/L]KALTNK[D/N]K | Kgp[432-468] |
| 2 | FNGGISL[V/A]NYTGHGSETAWGTSHFGTTHVKQLTNSNQ | RgpA[426-462] |
| 3 | VSFANYT | |
| 4 | VGFANYT | |
| 5 | GVSFANYT | |
| 6 | GVGFANYT | |
| 7 | VSFANYTA | |
| 8 | VGFANYTA | |
| 9 | ETAWAD | |
| 10 | ETSWAD | |
| 11 | TAWADP | |
| 12 | TSWADP | |
| 13 | SETAWAD | |
| 14 | SETSWAD | |

TABLE 3-continued

| | | |
|---|---|---|
| 15 | ETAWADP | |
| 16 | ETSWADP | |
| 17 | TAWADPL | |
| 18 | TSWADPL | |
| 19 | GSETAWAD | |
| 20 | GSETSWAD | |
| 21 | SETAWADP | |
| 22 | SETSWADP | |
| 23 | ETAWADPL | |
| 24 | ETSWADPL | |
| 25 | TAWADPLL | |
| 26 | TSWADPLL | |
| 27 | LNTGV[G/S]FANYTAHGSET[S/A]WADP[S/L] | KAS1 |
| 28 | NTGV[G/S]FANYTAHGSET[S/A]WADP[S/L][L/V]T[A/T][T/S]Q[V/L]KALTNK[D/N]K | KAS2 |
| 29 | V[G/S]FANYTAHGSET[S/A]WADP[S/L][L/V] | KAS3 |
| 30 | LNTGVSFANYTAHGSETAWADP | PAS1K |
| 31 | FNGGISL[V/A]NYTGHGSETAWGTSH | RAS1 |
| 32 | NGGISL[V/A]NYTGHGSETAWGTSHFGTTHVKQLTNSNQ | RAS2 |
| 33 | ISL[V/A]NYTGHGSETAWGTSHF | RAS3 |
| 34 | FNGGISLANYTGHGSETAWGT | PAS1R |
| 35 | ANEAKVVLAADNVWGDNTGYQFLLDADHNTFGSVIPATGPLFTGTASSNLYSANFEYLIPANADPVVTTQNIIVTGQGEVVIPGGVYDYCITNPEPASGKMWIAGDGGNQPARYDDFTFEAGKKYTFTMRRAGMGDGTDMEVEDDSPASYTYTVYRDGTKIKEGLTATTFEEDGVAAGNHEYCVEVKYTAGVSPKVCKDVTVEGSNEFAPVQNLTGSSVGQKVTLKWDAPNGTPNPNPNPNPNPGTTLSESFENGIPASWKTIDADGDGHGWKPGNAPGIAGYNSNGCVYSESFGLGGIGVLTPDNYLITPALDLPNGGKLTFWVCAQDANYASEHYAVYASSTGNDASNFTNALLEETITA | KA1 |
| 36 | FLLDADHNTFGSVIPATGPLFTGTASSNLYSANFEYLIPANADPVVTTQNIIVTGQGEVVIPGGVYDYCITNPEPASGKMWIAGDGGNQPARYDDFTFEAGKKYTFTMRRAGMGDGTDMEVEDDSPASYTYTVYRDGTKIKEGLTATTFEEDGVAAGNHEYCVEVKYTAGVSPKVCKDVTVEGSNEFAPVQNLTGSSVGQKVTLKWDAPNGTPNPNPNPNPNPGTTLSESF | KsA1 |
| 37 | WGDNTGYQFLLDADHNTFGSVIPATGPLFTGTASSNLYSANFEYLIPANADPVVTTQNIIVTGQGEVVIPGGVYDYCITNPEPASGKMWIAGDGGNQPARYDDFTFEAGKKYTFTMRRAGMGDGTDMEVEDDSPASYTYTVYRDGTKIKEGLTATTFEEDGVAAGNHEYCVEVKYTAGVSPKVCKDVTVEGSNEFAPVQNLTGSSVGQKVTLKWDAPNGTPNPNPNPNPGTTLSESFENGIPASWKTIDADGDGHGWKPGNAPGIAGYNSNGCVYSESFGLGGIGVLTPDNYLITPALDLPNGG | KLA1 |
| 38 | SGQAEIVLEAHDVWNDGSGYQILLDADHDQYGQVIPSDTHTLWPNCSVPANLFAPFEYTVPENADPSCSPTNMIMDGTASVNIPAGTYDFAIAAPQANAKIWIAGQGPTKEDDYVFEAGKKYHFLMKKMSGDGTELTISEGGGSDYTYTVYRDGTKIKEGLTATTFEEDGVATGNHEYCVEVKYTAGVSPKVCKDVTVEGSNEFAPVQNLTGSAVGQKVTLKWDAPNGTPNPNPNPNPNPGTTTLSESFENGIPASWKTIDADGDGHGWKPGNAPGIAGYNSNGCVYSESFGLGGIGVLTPDNYLITPALDLPNGGKLTFWVCAQDANYASEHYAVYASSTGNDASNFTNALLEETITA | RA1 |

TABLE 3-continued

| | | |
|---|---|---|
| 39 | DDYVFEAGKKYHFLMKKMGSGDGTELTISEGGGSDYTYT VYRDGTKIKEGLTATTFEEDGVATGNHEYCVEVKYTAGV SPKVCKDVTVEGSNEFAPVQNLTGSAVGQKVTLKWDAP NGTPNPNPNPNPNPNPGTTTLSESF | RsA1 |
| 40 | ADFTETFESSTHGEAPAEWTTIDADGDGQGWLCLSSGQ LDWLTAHGGSNVVSSFSWNGMALNPDNYLISKDVTGAT KVKYYYAVNDGFPGDHYAVMISKTGTNAGDFTVVFEETP NGIN | KA2 |
| 41 | PQSVWIERTVDLPAGTKYVAFRHYNCSDLNYILLDDIQFT MGGSPTPTDYTYTVYRDGTKIKEGLTETTFEEDGVATGN HEYCVEVKYTAGVSPKKCVNVTVNSTQFNPVQNLTAEQ APNSMDAILKWNAPAS | KA3 |
| 42 | AEVLNEDFENGIPASWKTIDADGDGNNWTTTPPPGGSSF AGHNSAICVSSASYINFEGPQNPDNYLVTPELSLPGGGTL TFWVCAQDANYASEHYAVYASSTGNDASNFANALLEEVL TA | KA4 |
| 43 | TVVTAPEAIRGTRAQGTWYQKTVQLPAGTKYVAFRHFGC TDFFWINLDDVVITSGNAPSYTYTIYRNNTQIASGVTETTY RDPDLATGFYTYGVKVVYPNGESAIETATLNITSLADVTA QKPYTLTVVGKTITVTCQGEAMIYDMNGRRLAAGRNTVV YTAQGGHYAVMVVVDGKSYVEKLAVK | KA5 |
| 44 | ADFTETFESSTHGEAPAEWTTIDADGDGQGWLCLSSGQ LDWLTAHGGTNVVSSFSWNGMALNPDNYLISKDVTGAT KVKYYYAVNDGFPGDHYAVMISKTGTNAGDFTVVFEETP NGIN | RA2 |
| 45 | PQSVWIERTVDLPAGTKYVAFRHYNCSDLNYILLDDIQFT MGGSPTPTDYTYTVYRDGTKIKEGLTETTFEEDGVATGN HEYCVEVKYTAGVSPKKCVNVTVNSTQFNPVKNLKAQP DGGDVVLKWEAPSA | RA3 |
| 46 | ANEAKVVLAADNVWGDNTGYQFLLDADHNTFGSVIPATG PLFTGTASSDLYSANFESLIPANADPVVTTQNIIVTGQGEV VIPGGVYDYCITNPEPASGKMWIAGDGGNQPARYDDFTF EAGKKYTFTMRRAGMGDGTDMEVEDDSPASYTYTVYRD GTKIKEGLTETTYRDAGMSAQSHEYCVEVKYTAGVSPKV CVDYIPDGVADVTAQKPYTLTVVGKTITVTCQGEAMIYDM NGRRLAAGRNTVVYTAQGGYYAVMVVVDGKSYVEKLAIK | RA4 |
| Nucleotide sequence | | |
| 47 | GACCATGGCTCATCACCATCACCATCACAATACCGG AGTCAGCTTTGCA | KAS2-FOR |
| 48 | GACTCGAGTTATTTGTCCTTATTAGTGAGTGCTTTC | KAS2-REV |
| 49 | GACCATGGCTTGGGGAGACAATACGGGTTAC | KLA1-FOR |
| 50 | GACTCGAGACCTCCGTTAGGCAAATCC | KLA1-REV |
| 51 | CCGTATTGTCTCCCCATTTGTCCTTATTAGTGAGTGC TTTC | KAS2-KLA1-REV |
| 52 | CACTAATAAGGACAAATGGGGAGACAATACGGGTTA C | KAS2-KLA1-FOR |
| 53 | CATGGATCTGAGACCGCATGGGCTGATCCACTTTTC TTGTTGGATGCCGAT | KAS1-KsA1-FOR1 |
| 54 | CCATGGCTTTGAATACCGGAGTCAGCTTTGCAAACT ATACAGCGCATGGATCTGAGACCGCA | KAS1-KsA1-FOR2 |
| 55 | CTCGAGGAATGATTCGGAAAGTGTT | KAS1-KsA1-REV |
| 56 | CCATGGCTGATTATAGCTGGAATTCCCAGGTAGTCA GCTTTGCAAACTATACA | multi-FOR1 |
| 57 | CTTTGCAAACTATACAGCGCATGGATCTGAGACCGC ATGGGCTGATCCACTT | multi-FOR2 |

TABLE 3-continued

| | | |
|---|---|---|
| 58 | ATGGGCTGATCCACTTCTGAATTCTTATTGGGGCGA GATCGGCAATATTACC | multi-FOR3 |
| 59 | GATCGGCAATATTACCCATATTGGTGCTCATTACGC TTGGGGAGACAATACG | multi-FOR4 |
| 60 | CTCGAGACCTCCGTTAGGCAAATCCAATGCCGGTGT TATCAGATAGTTGTCA | Multi-REV |

| SEQ ID NO: | Amino acid sequence | Full length |
|---|---|---|
| 61 | MKNLNKFVSIALCSSLLGGMAFAQQTELGRNPNVRLLES TQQSVTKVQFRMDNLKFTEVQTPKGIGQVPTYTEGVNL SEKGMPTLPILSRSLAVSDTREMKVEVVSSKFIEKKNVLI APSKGMIMRNEDPKKIPYVYGKTYSQNKFFPGEIATLDD PFILRDVRGQVVNFAPLQYNPVTKTLRIYTEITVAVSETSE QGKNILNKKGTFAGFEDTYKRMFMNYEPGRYTPVEEKQ NGRMIVIVAKKYEGDIKDFVDWKNQRGLRTEVKVAEDIA SPVTANAIQQFVKQEYEKEGNDLTYVLLIGDHKDIPAKITP GIKSDQVYGQIVGNDHYNEVFIGRFSCESKEDLKTQIDRT IHYERNITTEDKWLGQALCIASAEGGPSADNGESDIQHE NVIANLLTQYGYTKIIKCYDPGVTPKNIIDAFNGGISLANYT GHGSETAWGTSHFGTTHVKQLTNSNQLPFIFDVACVNG DPLFSMPCFAEALMRAQKDGKPTGTVAIIASTINQSWAS PMRGQDEMNEILCEKHPNNIKRTFGGVTMNGMFAMVEK YKKDGEKMLDTWTVFGDPSLLVRTLVPTKMQVTAPAQI NLTDASVNVSCDYNGAIATISANGKMFGSAVVENGTATI NLTGLTNESTLTLTVVGYNKETVIKTINTNGEPNPYQPVS NLTATTQGQKVTLKWDAPSTKTNATTNTARSVDGIRELV LLSVSDAPELLRSGQAEIVLEAHDVWNDGSGYQILLDAD HDQYGQVIPSDTHTLWPNCSVPANLFAPFEYTVPENAD PSCSPTNMIMDGTASVNIPAGTYDFAIAAPQANAKIWIAG QGPTKEDDYVFEAGKKYHFLMKKMGSGDGTELTISEGG GSDYTYTVYRDGTKIKEGLTATTFEEDGVATGNHEYCVE VKYTAGVSPKVCKDVTVEGSNEFAPVQNLTGSAVGQKV TLKWDAPNGTPNPNPNPNPNPNPGTTTLSESFENGIPA SWKTIDADGDGHGWKPGNAPGIAGYNSNGCVYSESFG LGGIGVLTPDNYLITPALDLPNGGKLTFWVCAQDANYAS EHYAVYASSTGNDASNFTNALLEETITAKGVRSPEAMRG RIQGTWRQKTVDLPAGTKYVAFRHFQSTDMFYIDLDEVE IKANGKRADFTETFESSTHGEAPAEWTTIDADGDGQGW LCLSSGQLDWLTAHGGTNVVSSFSWNGMALNPDNYLIS KDVTGATKVKYYYAVNDGFPGDHYAVMISKTGTNAGDF TVVFEETPNGINKGGARFGLSTEADGAKPQSVWIERTVD LPAGTKYVAFRHYNCSDLNYILLDDIQFTMGGSPTPTDY TYTVYRDGTKIKEGLTETTFEEDGVATGNHEYCVEVKYT AGVSPKKCVNVTVNSTQFNPVKNLKAQPDGGDVVLKW EAPSAKKTEGSREVKRIGDGLFVTIEPANDVRANEAKVV LAADNVWGDNTGYQFLLDADHNTFGSVIPATGPLFTGTA SSDLYSANFESLIPANADPVVTTQNIIVTGQGEVVIPGGV YDYCITNPEPASGKMWIAGDGGNQPARYDDFTFEAGKK YTFTMRRAGMGDGTDMEVEDDSPASYTYTVYRDGTKIK EGLTETTYRDAGMSAQSHEYCVEVKYTAGVSPKVCVDY IPDGVADVTAQKPYTLTVVGKTITVTCQGEAMIYDMNGR RLAAGRNTVVYTAQGGYYAVMVVVDGKSYVEKLAIK | RgpA |
| 62 | MRKLLLLIAASLLGVGLYAQSAKIKLDAPTTRTTCTNNSF KQFDASFSFNEVELTKVETKGGTFASVSIPGAFPTGEVG SPEVPAVRKLIAVPVGATPVVRVKSFTEQVYSLNQYGSE KLMPHQPSMSKSDDPEKVPFVYNAAAYARKGFVGQELT QVEMLGTMRGVRIAALTINPVQYDVVANQLKVRNNIEIEV SFQGADEVATQRLYDASFSPYFETAYKQLFNRDVYTDH GDLYNTPVRMLVVAGAKFKEALKPWLTWKAQKGFYLDV HYTDEAEVGTTNASIKAFIHKKYNDGLAASAAPVFLALVG DTDVISGEKGKKTKKVTDLYYSAVDGDYFPEMYTFRMS ASSPEELTNIIDKVLMYEKATMPDKSYLEKVLLIAGADYS WNSQVGQPTIKYGMQYYYNQEHGYTDVYNYLKAPYTG CYSHLNTGVSFANYTAHGSETAWADPLLTTSQLKALTNK DKYFLAIGNCCITAQFDYVQPCFGEVITRVKEKGAYAYIG SSPNSYWGEDYYWSVGANAVFGVQPTFEGTSMGSYDA TFLEDSYNTVNSIMWAGNLAATHAGNIGNITHIGAHYYW EAYHVLGDGSVMPYRAMPKTNYTLPASLPQNQASYSI QASAGSYVAISKDGVLYGTGVANASGVATVSMTKQITEN GNYDVVITRSNYLPVIKQIQVGEPSPYQPVSNLTATTQG QKVTLKWEAPSAKKAEGSREVKRIGDGLFVTIEPANDVR | Kgp |

TABLE 3-continued

|  |  |  |
|---|---|---|
|  | ANEAKVVLAADNVWGDNTGYQFLLDADHNTFGSVIPAT GPLFTGTASSNLYSANFEYLIPANADPVVTTQNIIVTGQG EVVIPGGVYDYCITNPEPASGKMWIAGDGGNQPARYDD FTFEAGKKYTFTMRRAGMGDGTDMEVEDDSPASYTYV YRDGTKIKEGLTATTFEEDGVAAGNHEYCVEVKYTAGVS PKVCKDVTVEGSNEFAPVQNLTGSSVGQKVTLKWDAPN GTPNPNPNPNPNPGTTLSESFENGIPASWKTIDADGDG HGWKPGNAPGIAGYNSNGCVYSESFGLGGIGVLTPDNY LITPALDLPNGGKLTFWVCAQDANYASEHYAVYASSTGN DASNFTNALLEETITAKGVRSPKAIRGRIQGTWRQKTVDL PAGTKYVAFRHFQSTDMFYIDLDEVEIKANGKRADFTET FESSTHGEAPAEWTTIDADGDGQGWLCLSSGQLDWLT AHGGSNVVSSFSWNGMALNPDNYLISKDVTGATKVKYY YAVNDGFPGDHYAVMISKTGTNAGDFTVVFEETPNGINK GGARFGLSTEANGAKPQSVWIERTVDLPAGTKYVAFRH YNCSDLNYILLDDIQFTMGGSPTPTDYTYTVYRDGTKIKE GLTETTFEEDGVATGNHEYCVEVKYTAGVSPKKCVNVT VNSTQFNPVQNLTAEQAPNSMDAILKWNAPASKRAEVL NEDFENGIPASWKTIDADGDGNNWTTTPPPGGSSFAGH NSAICVSSASYINFEGPQNPDNYLVTPELSLPGGGTLTF WVCAQDANYASEHYAVYASSTGNDASNFANALLEEVLT AKTVVTAPEAIRGTRAQGTWYQKTVQLPAGTKYVAFRH FGCTDFFWINLDDVVITSGNAPSYTYTIYRNNTQIASGVT ETTYRDPDLATGFYTYGVKVVYPNGESAIETATLNITSLA DVTAQKPYTLTVVGKTITVTCQGEAMIYDMNGRRLAAGR NTVVYTAQGGHYAVMVVVDGKSYVEKLAVK |  |
| 63 | MRKLNSLFSLAVLLSLLCWGQTAAAQGGPKTAPSVTHQ AVQKGIRTSKAKDLRDPIPAGMARIILEAHDVWEDGTGY QMLWDADHNQYGASIPEESFWFANGTIPAGLYDPFEYK VPVNADASFSPTNFVLDGTASADIPAGTYDYVIINPNPGII YIVGEGVSKGNDYVVEAGKTYHFTVQRQGPGDAASVVV TGEGGNEFAPVQNLQWSVSGQTVTLTWQAPASDKRTY VLNESFDTQTLPNGWTMIDADGDGHNWLSTINVYNTAT HTGDGAMFSKSWTASSGAKIDLSPDNYLVTPKFTVPEN GKLSYWVSSQEPWTNEHYGVFLSTTGNEAANFTIKLLEE TLGSGKPAPMNLVKSEGVKAPAPYQERTIDLSAYAGQQ VYLAFRHFGCTGIFRLYLDDVAVSGEGSSNDYTYTVYRD NVVIAQNLTATTFNQENVAPGQYNYCVEVKYTAGVSPKV CKDVTVEGSNEFAPVQNLTGSAVGQKVTLKWDAPNGTP NPNPGTTTLSESFENGIPASWKTIDADGDGNNWTTTPPP GGSSFAGHNSAICVSSASYINFEGPQNPDNYLVTPELSL PNGGTLTFWVCAQDANYASEHYAVYASSTGNDASNFA NALLEEVLTAKTVVTAPEAIRGTRVQGTWYQKTVQLPAG TKYVAFRHFGCTDFFWINLDDVEIKANGKRADFTETFES STHGEAPAEWTTIDADGDGQGWLCLSSGQLGWLTAHG GTNVVASFSWNGMALNPDNYLISKDVTGATKVKYYYAV NDGFPGDHYAVMISKTGTNAGDFTVVFEETPNGINKGG ARFGLSTEANGAKPQSVWIERTVDLPAGTKYVAFRHYN CSDLNYILLDDIQFTMGGSPTPTDYTYTVYRDGTKIKEGL TETTFEEDGVATGNHEYCVEVKYTAGVSPKECVNVTVD PVQFNPVQNLTGSAVGQKVTLKWDAPNGTPNPNPGTTT LSESFENGIPASWKTIDADGDGNNWTTTPPPGGTSFAG HNSAICVSSASYINFEGPQNPDNYLVTPELSLPNGGTLTF WVCAQDANYASEHYAVYASSTGNDASNFANALLEEVLT AKTVVTAPEAIRGTRVQGTWYQKTVQLPAGTKYVAFRH FGCTDFFWINLDDVEIKANGKRADFTETFESSTHGEAPA EWTTIDADGDGQGWLCLSSGQLDWLTAHGGTNVVASF SWNGMALNPDNYLISKDVTGATKVKYYYAVNDGFPGDH YAVMISKTGTNAGDFTVVFEETPNGINKGGARFGLSTEA NGAKPQSVWIERTVDLPAGTKYVAFRHYNCSDLNYILLD DIQFTMGGSPTPTDYTYTVYRDGTKIKEGLTETTFEEDG VATGNHEYCVEVKYTAGVSPKECVNVTVDPVQFNPVQN LTGSAVGQKVTLKWDAPNGTPNPNPGTTTLSESFENGIP ASWKTIDADGDGNNWTTTPPPGGTSFAGHNSAICVSSA SYINFEGPQNPDNYLVTPELSLPNGGTLTFWVCAQDAN YASEHYAVYASSTGNDASNFANALLEEVLTAKTVVTAPE AIRGTRVQGTWYQKTVQLPAGTKYVAFRHFGCTDFFWI NLDDVEIKANGKRADFTETFESSTHGEAPAEWTTIDADG DGQGWLCLSSGQLGWLTAHGGTNVVASFSWNGMALN PDNYLISKDVTGATKVKYYYAVNDGFPGDHYAVMISKTG TNAGDFTVVFEETPNGINKGGARFGLSTEANGAKPQSV WIERTVDLPAGTKYVAFRHYNCSDLNYILLDDIQFTMGG SPTPTDYTYTVYRDGTKIKEGLTETTFEEDGVATGNHEY CVEVKYTAGVSPKECVNVTINPTQFNPVQNLTAEQAPNS MDAILKWNAPASKRAEVLNEDFENGIPASWKTIDADGDG NNWTTTPPPGGSSFAGHNSAICVSSASYINFEGPQNPD NYLVTPELSLPGGGTLTFWVCAQDANYASEHYAVYASS TGNDASNFANALLEEVLTAKTVVTAPEAIRGTRVQGTWY QKTVQLPAGTKYVAFRHFGCTDFFWINLDDVVITSGNAP | HagA |

TABLE 3-continued

```
     SYTYTIYRNNTQIASGVTETTYRDPDLATGFYTYGVKVVY
     PNGESAIETATLNITSLADVTAQKPYTLTVVGKTITVTCQG
     EAMIYDMNGRRLAAGRNTVVYTAQGGHYAVMVVVDGK
     SYVEKLAVK
```

| # | Sequence | Fragment |
|---|---|---|
| 64 | D[S/Y][Y/S]WN[P/S][K/Q][I/V] | KAS4 |
| 65 | NSYWGED | KAS5 |
| 66 | IGN[V/I]THIGAHY | KAS6 |
| 67 | EGGPSADN | RAS4 |
| 68 | [N/D]Q[S/Y]WA[S/P]P | RAS5 |
| 69 | PVSNLTATTQGQKVTLKWDAPST | ABM1-RgpA$_{cat}$ |
| 70 | PVSNLTATTQGQKVTLKWEAPSA | ABM1-Kgpcat |
| 71 | PVQNLTGSSVGQKVTLKWDAPST | ABM1-KgpA1 |
| 72 | PVQNLTGSAVGQKVTLKWDAPNG | ABM1-RgpA1 & RgpAA3 |
| 73 | PVKNLKAQPDGGDVVLKWEAPSA | ABM1-HagAA1*/** |
| 74 | PVQNLTAEQAPNSMDAILKWNAP | ABM1-KgpA3 & HagAA3 |
| 75 | PVQNLTQWSVSGQTVTLTWQAPAS | ABM2-HagAA1 |
| 76 | YTYTVYRDGTKIKEGLTETTFEEDGVA | ABM2-ABM2-RgpAA4 |
| 77 | YTYTVYRDNVVIAQNLTATTFNQENVA | ABM2-HagA1* |
| 78 | YTYTVYRDGTKIKEGLTA/ETTFEEDGVA | ABM2 All other adhesins |
| 79 | PNGTP(NP)$_{1-6}$GTT(T)LSESF | ABM3-All adhesins |
| 80 | QGGPKTAPSVTHQAVQKGIRTSKAKDLRDPIPAGMARIILE AHDVWEDGTGYQMLWDADHNQYGASIPEESFWFANGTI PAGLYDPFEYKVPVNADASFSPTNFVLDGTASADIPAGTY DYVIINPNPGIIYIVGEGVSKGNDYVVEAGKTYHFTVQRQ GPGDAASVVVTGEGGNEFAPVQNLQWSVSGQTVTLTW QAPASDKRTYVLNESFDTQTLPNGWTMIDADGDGHNWL STINVYNTATHTGDGAMFSKSWTASSGAKIDLSPDNYLVT PKFTVPENGKLSYWVSSQEPWTNEHYGVFLSTTGNEAA NFTIKLLEETLGSG | HagA1 [26-351] |
| 81 | APAPYQERTIDLSAYAGQQVYLAFRHFGCTGIFRLYLDDV AVSGEGSSNDYTYTVYRDNVVIAQNLTATTFNQENVAPG QYNYCVEVKYTAGVSPKVCKDVTVEGSNEFAPVQNLTG SAVGQKVTLKWDAPNGTPNPNGTTTLSESFENGIPASW KTIDADGDGNNWTTTPPPGGSSFAGHNSAICVSSASYIN FEGPQNPDNYLVTPELSLPNGGTLTFWVCAQDANYASE HYAVYASSTGNDASNFANALLEEVLTA | HagA1* [366-625] |
| 82 | PQSVWIERTVDLPAGTKYVAFRHYNCSDLNYILLDDIQFT MGGSPTPTDYTYTVYRDGTKIKEGLTETTFEEDGVATGN HEYCVEVKYTAGVSPKECVNVTVDPVQFNPVQNLTGSA VGQKVTLKWDAPNGTPNPNPGTTTLSESFENGIPASWKT IDADGDGNNWTTTPPPGGTSFAGHNSAICVSSASYINFE GPQNPDNYLVTPELSLPNGGTLTFWVCAQDANYASEHY AVYASSTGNDASNFANALLEEVLTA | HagA1** [820-1077] or HagA1** [1272-1529] |

TABLE 3-continued

| 83 | PYQPVSNLTATTQGQ | ABM1[436-450] |
| 84 | EGLTATTFEEDGVAA | ABM2[672-686] |
| 85 | GTPNPNPNPNPNPNPGT | ABM3[455-471] |

In the chimeric or fusion proteins of the present invention, the C-terminal residue of the first peptide may be covalently linked to the N-terminal residue of an adhesin domain polypeptide, or the N-terminal residue of the first peptide may be covalently linked to the C-terminal residue of an adhesin domain polypeptide. In this arrangement, the first peptide and adhesin domain polypeptide, are said to be "directly linked" or "adjacent".

In other embodiments, the chimeric or fusion protein includes a linker for linking the first peptide to an adhesin domain polypeptide. The linker may be any linker able to join a peptide to a polypeptide, including both amino acid and non-amino acid linkers. Preferably, the linker is non-immunogenic. Suitable linkers may be up to 15 amino acids in length, although less than five amino acids is preferred. The linker may function to bring the first peptide and adhesin domain polypeptide into a closer spatial arrangement than normally observed in a *P. gingivalis* trypsin-like enzyme. Alternatively, it may space the first peptide and adhesin domain polypeptide apart.

The chimeric or fusion proteins of the invention may be produced by recombinant expression systems (such as recombinant DNA technology) or by chemical synthesis (such as solid phase peptide synthesis). These techniques are well known in the art.

The heterologous or chimeric protein is particularly advantageous because it improves the humoral response obtained over that obtained using the first or second peptide components of the chimeric or fusion protein alone.

The inventors have found that chimeric proteins including these peptides have a number of utilities. For example, as described herein, some produce a humoral response that is highly protective for treatment or prevention of bone loss as observed in chronic periodontitis. The peptides may also be used in a diagnostic assay wherein they can detect or monitor specificities in an individual's serum, thereby indicating whether or not the individual is infected and if so, whether treatments are required or if provided, whether they have been effective.

In one embodiment, the chimeric or fusion protein induces a protective immune response, typically a response that at least minimises or limits connective tissue damage otherwise associated with *P. gingivalis* infection. In one embodiment the protective response at least minimises or limits *P. gingivalis* induced bone loss. A model system for measuring bone loss mediated by *P. gingivalis* infection is discussed herein. Typically the protective immune response is predominantly a humoral response. In certain embodiments the protective immune response also includes a cellular response.

The present invention also provides a composition including a chimeric or fusion protein as broadly described above. Typically the composition is antigenic or immunogenic. More particularly, the invention provides a composition suitable for eliciting a protective or therapeutic immune response against *P. gingivalis* infection, including the chimeric or fusion protein, optionally in association with an adjuvant. Such a composition may also include another component for modulating or potentiating the immune response. One embodiment, the composition takes the form of a vaccine.

A preferred composition includes immunogens that generate an immune response to the periodontal pathogens *Porphyromonas gingivalis, Treponema denticola*, and *Tannerella forsythia*. Immunogens may be attenuated whole cell vaccine, or a purified antigen vaccine or more preferably a recombinant antigen vaccine where the composition contains antigens against one or more of the three periodontal pathogens. Other examples of suitable peptides capable of forming immunogens relevant to *P. gingivalis, T. denticola* and *T. forsythia* infection are shown in Tables D to F.

TABLE D

| Bacteria | Exemplary immunogen(s) | Exemplary reference(s) |
|---|---|---|
| *Porphryomonas gingivalis* | Proteinases or fragments thereof | U.S. Pat. No. 6,017,532 (see, for example, sequence listing) |
|  | Proteinases or fragments thereof specified in the sequence listing | 5,475,097 (see, for example, sequence listing) |
|  | PrtK48, PrtR45, PrtR44, PrtK39, PrtK44, PrtR27, PrtR17, PrtK15 and PrtR15 or fragments thereof | PCT/AU96/00673 |
|  | Ag1, Ag2, Ag3 and Ag4 or fragments thereof | PCT/AU97/00212 (see, for example, Table on page 3). |
|  | Peptides from cysteine proteases and adhesins | PCT/AU98/00311 (see, for example, Table 1) |
|  | Polypeptides and fragments thereof | PCT/AU1998/00311 (see, for example, Table 1, 2 or 3 and sequence listing) |

TABLE D-continued

| Bacteria | Exemplary immunogen(s) | Exemplary reference(s) |
|---|---|---|
| | PrtR-PrtK proteinase-adhesin complex and fragments thereof | U.S. Pat. No. 6,962,706 (see, for example, Table 1 or sequence listing) |
| | r-RgpA44 and r-Kgp39 and fragments thereof | PCT/AU00/01588 (see, for example, sequence listing) |
| | PG32 and PG33 and fragments thereof | PCT/AU01/00482 (see, for example, Table 3 or sequence listing) |
| | Multimeric complex | PCT/AU2005/001463 |
| | Polypeptides and fragments thereof | PCT/AU2007/000890 (see, for example, Table 2) |
| | Polypeptides and fragments thereof | PCT/AU2008/001018 (see, for example, Table 4) |
| | Polypeptides and fragments thereof | PCT/US2004/025778 (see, for example, Table 2 or sequence listing) |
| | Adhesins and fragments thereof | US 2005/0288866 (see, for example, Table 5) |
| | Isolated, purified or extracted bacterial preparation | |
| Treponema denticola | Polypeptides and fragments thereof | Disclosed in Veith et al. Biochmica et Biophysica Acta. 2009, vol. 1794: 1421-1432 and listed in Table E. |
| | Isolated, purified or extracted bacterial preparation | |
| Tannerella forsythia | Polypeptides and fragments thereof | Disclosed in Table 1, 2 and 3 in Veith et al. Journal of Proteome Research (2009) vol. 8: 4279-4292 and listed in Table F. |
| | Polypeptides and fragments thereof | Yoo et al. FEMS Microbiol. Lett. (2007) 275: 344-352 |
| | Isolated, purified or extracted bacterial preparation | PCT/IB2004/003310 |

TABLE E

| [1]Accession | [1]Protein Definition |
|---|---|
| TDE0011 | alkyl hydroperoxide reductase/peroxiredoxin |
| TDE0017 | conserved hypothetical protein |
| TDE0018 | LysM domain protein |
| TDE0019 | formate--tetrahydrofolate ligase (fhs) |
| TDE0042 | phosphate acetyltransferase (pta) |
| TDE0046 | formiminotransferase-cyclodeaminase family protein |
| TDE0047 | imidazolonepropionase (hutI) |
| TDE0048 | hypothetical protein |
| TDE0051 | alcohol dehydrogenase, iron-containing |
| TDE0068 | peptidase, M20/M25/M40 family |
| TDE0102 | cyclic nucleotide-binding protein |
| TDE0117 | lipoprotein, putative |
| TDE0139 | hypothetical protein |
| TDE0153 | coenzyme A disulfide reductase, putative |
| TDE0167 | ABC transporter, ATP-binding protein |
| TDE0182 | ABC transporter, ATP-binding protein |
| TDE0186 | hypothetical protein |
| TDE0231 | DNA polymerase III, beta subunit (dnaN) |
| TDE0240 | glycine reductase complex protein GrdC (grdC) |
| TDE0249 | flavoredoxin, putative |
| TDE0251 | tryptophanase (tnaA) |
| TDE0296 | formiminotransferase, putative |
| TDE0300 | cytosol aminopeptidase family protein |
| TDE0311 | thymidylate synthase-complementing family protein |
| TDE0313 | TrkA domain protein |
| TDE0325 | hypothetical protein |
| TDE0337 | glucosamine-6-phosphate isomerase (nagB) |
| TDE0340 | fructose-bisphosphate aldolase, class-I |
| TDE0351 | L-lactate dehydrogenase (ldh) |
| TDE0354 | general stress protein 14 |
| TDE0386 | ABC transporter, periplasmic substrate-binding protein |
| TDE0389 | (R)-2-hydroxyglutaryl-CoA dehydratase, beta subunit, putative |
| TDE0398 | oligopeptide/dipeptide ABC transporter, periplasmic peptide-binding protein |
| TDE0405 | major outer sheath protein |
| TDE0407 | glutamate synthase (NADPH), homotetrameric (gltA) |
| TDE0434 | rubrerythrin |
| TDE0444 | glutamine amidotransferase class-I domain protein |
| TDE0449 | ferritin, putative |
| TDE0451 | arginine deiminase (arcA) |
| TDE0456 | pyridoxine biosynthesis protein |
| TDE0463 | purine nucleoside phosphorylase (deoD) |
| TDE0467 | hypothetical protein |
| TDE0525 | hypothetical protein |
| TDE0576 | glutamyl-tRNA(Gln) amidotransferase, A subunit (gatA) |
| TDE0585 | hypothetical protein |
| TDE0588 | histidine ammonia-lyase (hutH) |
| TDE0603 | conserved hypothetical protein |
| TDE0610 | 3-hydroxyacyl-CoA dehydrogenase, putative |

TABLE E-continued

| ¹Accession | ¹Protein Definition |
|---|---|
| TDE0628 | chaperone protein DnaK (dnaK) |
| TDE0648 | protein-glutamate methylesterase (cheB) |
| TDE0664 | OmpA family protein |
| TDE0665 | pyruvate ferredoxin/flavodoxin oxidoreductase family protein |
| TDE0677 | conserved hypothetical protein |
| TDE0679 | aminotransferase, class V |
| TDE0704 | SPFH domain/Band 7 family protein |
| TDE0731 | hypothetical protein |
| TDE0743 | thioredoxin reductase (trxB) |
| TDE0744 | thioredoxin (trxA) |
| TDE0748 | iron compound ABC transporter, periplasmic iron compound-binding protein, putative |
| TDE0754 | hypothetical protein |
| TDE0758 | iron compound ABC transporter, periplasmic iron compound-binding protein, putative |
| TDE0761 | protease complex-associated polypeptide (prcA) |
| TDE0765 | translation elongation factor Tu (tuf) |
| TDE0816 | peptidase, M20/M25/M40 family |
| TDE0823 | (3R)-hydroxymyristoyl-(acyl-carrier-protein) dehydratase, putative |
| TDE0829 | aspartyl aminopeptidase, putative |
| TDE0842 | cytoplasmic filament protein A (cfpA) |
| TDE0845 | conserved hypothetical protein TIGR00266 |
| TDE0855 | DNA-binding response regulator |
| TDE0911 | type II restriction endonuclease TdeIII (tdeIIIR) |
| TDE0925 | peptidase T (pepT) |
| TDE0929 | ornithine carbamoyltransferase (argF) |
| TDE0939 | lipoprotein, putative |
| TDE0947 | translation elongation factor G, putative |
| TDE0949 | enolase (eno) |
| TDE0951 | lipoprotein, putative |
| TDE0985 | oligopeptide/dipeptide ABC transporter, periplasmic peptide-binding protein, putative |
| TDE1000 | 3-hydroxyacid dehydrogenase family protein |
| TDE1001 | orotate phosphoribosyltransferase (pyrE) |
| TDE1004 | flagellar filament core protein |
| TDE1041 | polyribonucleotide nucleotidyltransferase (pnp) |
| TDE1049 | translation elongation factor G (fusA-2) |
| TDE1050 | hypothetical protein |
| TDE1071 | peptide ABC transporter, peptide-binding protein OppA (oppA) |
| TDE1072 | lipoprotein, putative |
| TDE1078 | metallo-beta-lactamase family protein |
| TDE1090 | threonyl-tRNA synthetase (thrS) |
| TDE1118 | tyrosine phenol-lyase (tpl) |
| TDE1127 | TPR domain protein |
| TDE1149 | hypothetical protein |
| TDE1175 | chaperonin, 60 kDa (groEL) |
| TDE1195 | prolyl endopeptidase |
| TDE1231 | hypothetical protein |
| TDE1236 | triosephosphate isomerase (tpiA) |
| TDE1237 | hypothetical protein |
| TDE1246 | lipoprotein, putative |
| TDE1247 | hypothetical protein |
| TDE1252 | lipoprotein, putative |
| TDE1273 | oligopeptide/dipeptide ABC transporter, peptide-binding protein |
| TDE1283 | extracellular solute-binding lipoprotein, putative |
| TDE1292 | TldD/PmbA family protein |
| TDE1301 | DNA repair protein RecN (recN) |
| TDE1308 | transketolase (tkt) |
| TDE1310 | modulator of DNA gyrase family protein |
| TDE1356 | lipoprotein, putative |
| TDE1357 | aldose 1-epimerase (galM) |
| TDE1371 | RNB-like family protein |
| TDE1372 | hypothetical protein |
| TDE1398 | conserved hypothetical protein |
| TDE1408 | flagellar filament outer layer protein FlaA, putative |
| TDE1409 | flagellar filament outer layer protein FlaA, putative |
| TDE1413 | cytidylyltransferase/phosphoenolpyruvate phosphomutase, putative |
| TDE1415 | nucleotidyl transferase/aminotransferase, class V |
| TDE1426 | aminotransferase, DegT/DnrJ/EryC1/StrS family |
| TDE1440 | glucose-1-phosphate thymidylyltransferase (rfbA) |
| TDE1475 | flagellar filament core protein |
| TDE1477 | flagellar filament core protein |
| TDE1482 | peptidase, M24 family protein |
| TDE1488 | glyceraldehyde-3-phosphate dehydrogenase, type I (gap) |
| TDE1491 | chemotaxis protein CheA (cheA) |
| TDE1492 | chemotaxis protein CheW (cheW-1) |
| TDE1493 | chemotaxis protein CheX (cheX) |
| TDE1494 | chemotaxis protein CheY (cheY) |
| TDE1499 | adenylosuccinate lyase, putative |
| TDE1511 | pathogen-specific surface antigen, putative |
| TDE1520 | hydro-lyase, tartrate/fumarate family, alpha subunit |
| TDE1558 | YD repeat protein |
| TDE1584 | lipoprotein, putative |
| TDE1589 | purine-binding chemotaxis protein (cheW-2) |
| TDE1598 | ABC transporter, ATP-binding protein |
| TDE1624 | glycine cleavage system P protein, subunit 2 (gcvP2) |
| TDE1625 | glycine cleavage system P protein, subunit 1 (gcvP1) |
| TDE1626 | glycine cleavage system H protein (gcvH) |
| TDE1627 | glycine cleavage system T protein (gcvT) |
| TDE1629 | dihydrolipoamide dehydrogenase (lpdA) |
| TDE1631 | citrate lyase, alpha subunit (citF) |
| TDE1632 | citrate lyase, beta subunit (citE) |
| TDE1642 | conserved hypothetical protein |
| TDE1658 | basic membrane protein, putative |
| TDE1663 | OmpA family protein |
| TDE1664 | conserved domain protein |
| TDE1669 | hemolysin |
| TDE1671 | trigger factor (tig) |
| TDE1682 | V-type ATPase, B subunit (atpB) |
| TDE1697 | phosphoglycerate mutase (gpm) |
| TDE1712 | flagellar filament outer layer protein (flaA) |
| TDE1715 | phosphoglycerate kinase (pgk) |
| TDE1717 | hypothetical protein |
| TDE1727 | conserved hypothetical protein |
| TDE1728 | hypothetical protein |
| TDE1754 | desulfoferrodoxin/neelaredoxin |
| TDE1848 | hypothetical protein |
| TDE1857 | conserved hypothetical protein |
| TDE1862 | conserved domain protein |
| TDE1915 | alcohol dehydrogenase, iron-containing |
| TDE1950 | membrane lipoprotein TmpC, putative |
| TDE2028 | OmpA family protein |
| TDE2049 | bacterial extracellular solute-binding proteins, family 5 |
| TDE2055 | hemin-binding protein B (hbpB) |
| TDE2056 | outer membrane hemin-binding protein A |
| TDE2058 | conserved hypothetical protein |
| TDE2069 | endoribonuclease L-PSP, putative |
| TDE2085 | amino acid kinase family protein |
| TDE2104 | hypothetical protein |
| TDE2120 | glycine reductase complex proprotein GrdE2 (grdE-2) |
| TDE2132 | cobalt ABC transporter, ATP-binding protein, putative |
| TDE2140 | protease II (ptrB) |
| TDE2164 | hypothetical protein |
| TDE2188 | hypothetical protein |
| TDE2194 | 8-amino-7-oxononanoate synthase, putative |
| TDE2200 | methionine gamma-lyase (megL) |
| TDE2211 | hypothetical protein |
| TDE2217 | galactose/glucose-binding lipoprotein (mglB) |
| TDE2234 | iron compound ABC transporter, periplasmic iron compound-binding protein, putative |
| TDE2235 | methylaspartate ammonia-lyase |
| TDE2236 | methylaspartate mutase, E subunit (glmE) |
| TDE2242 | antigen, putative |
| TDE2257 | 5-nucleotidase family protein |
| TDE2290 | transcriptional regulator, putative |
| TDE2300 | trypsin domain/PDZ domain protein |
| TDE2315 | conserved hypothetical protein TIGR00044 |
| TDE2337 | aminopeptidase |
| TDE2353 | flagellar hook-associated protein 3 |
| TDE2369 | conserved domain protein |
| TDE2390 | hypothetical protein |
| TDE2391 | peptidyl-prolyl cis-trans isomerase |
| TDE2392 | hypothetical protein |
| TDE2405 | conserved hypothetical protein |
| TDE2406 | TldD/PmbA family protein |
| TDE2422 | ribosomal protein L7/L12 (rplL) |
| TDE2433 | treponemal membrane protein, putative |
| TDE2439 | conserved hypothetical protein |
| TDE2480 | chaperone protein HtpG (htpG) |
| TDE2489 | peptide chain release factor 1 (prfA) |
| TDE2508 | hypothetical protein |

TABLE E-continued

| ¹Accession | ¹Protein Definition |
|---|---|
| TDE2540 | lipoprotein, putative |
| TDE2567 | hypothetical protein |
| TDE2584 | dipeptidase |
| TDE2589 | aminopeptidase, putative |
| TDE2601 | surface antigen, putative |
| TDE2602 | outer membrane protein, putative |
| TDE2606 | urocanate hydratase (hutU) |
| TDE2639 | oligoendopeptidase F (pepF) |
| TDE2647 | lipoyltransferase and lipoate-protein ligase family protein |
| TDE2665 | inosine-5-monophosphate dehydrogenase (guaB) |
| TDE2668 | serine hydroxymethyltransferase (glyA) |
| TDE2693 | ankyrin repeat protein |
| TDE2699 | antigen, putative |
| TDE2712 | hypothetical protein |
| TDE2716 | HAD-superfamily hydrolase, subfamily IA |
| TDE2730 | hydrolase, TatD family |
| TDE2734 | hypothetical protein |
| TDE2738 | oligoendopeptidase F, putative |
| TDE2754 | ornithine cyclodeaminase (arcB) |
| TDE2776 | proline iminopeptidase (pip) |
| TDE2779 | hypothetical protein |

¹Accessions and definitions from TIGR (now JCVI, www.tigr.org). Definitions are from TIGR's automated annotation of the genome.

TABLE F

| Accession[a] | Protein Description[a], abbreviated[b] |
|---|---|
| TF0071 | HP-C |
| TF0299 | HP |
| TF0324 | HP-C |
| TF0399 | HP |
| TF0436 | conserved hypothetical protein |
| TF0508 | HP-C |
| TF0706 | possible OM transport protein |
| TF0761 | HP-C |
| TF0773 | OM efflux protein |
| TF0810 | possible OM efflux protein |
| TF1015 | HP-C |
| TF1038 | HP-C |
| TF1059 | possible xanthan lyase |
| TF1300 | HP-C |
| TF1331 | Omp |
| TF1409 | Omp TolC |
| TF1441 | HP-C |
| TF1443 | HP |
| TF1444 | HP-C; possible hemin receptor |
| TF1476 | Omp P49 |
| TF1793 | polyphosphate-selective porin O |
| TF1822 | OM lipoprotein silC precursor |
| TF1959 | HP-C |
| TF2123 | HP-C; TPR-repeat protein |
| TF2450 | Omp |
| TF2595 | HP-C |
| TF2613 | HP-C |
| TF2734 | HP-C |
| TF2852 | HP-C |
| TF2901 | HP-C |
| TF3007 | HP-C |
| TF3114 | HP |
| TF0041 | Omp, TDR |
| TF0063 | HP-C |
| TF0064 | HP-C |
| TF0301 | Omp, TDR |
| TF0318 | Omp, TDR |
| TF0875 | OM receptor, TonB-linked |
| TF0980 | OM TDR |
| TF2096 | possible OmpA, OM-related protein |
| TF2124 | HP-C; possible TDR |
| TF2778 | Omp, TDR |
| TF3087 | HP-C |
| TF0045 | Omp, TDR |
| TF0044 | HP-C |
| TF0093 | Omp, TDR |
| TF0092 | Omp |
| TF0111 | Omp |

TABLE F-continued

| Accession[a] | Protein Description[a], abbreviated[b] |
|---|---|
| TF0112 | Omp |
| TF0237 | Omp, TDR |
| TF0238 | Omp |
| TF0275 | Omp |
| TF0277 | Omp |
| TF0313 | Omp, TDR |
| TF0312 | Omp |
| TF0424 | OM receptor, TonB-linked |
| TF0425 | Omp |
| TF0482 | OM receptor |
| TF0483 | OM receptor |
| TF0588 | Omp |
| TF0587 | Omp |
| TF0640 | Omp, TDR |
| TF0641 | Omp |
| TF0654 | OM receptor, TonB-linked |
| TF0655 | Omp |
| TF0682 | Omp, TDR |
| TF0683 | HP-C |
| TF0778 | Omp, TDR |
| TF0779 | possible Omp |
| TF0976 | OM receptor, Ton-linked |
| TF0977 | possible Omp |
| TF1053 | OM receptor, TonB-linked |
| TF1052 | HP-C |
| TF1057 | possible OM receptor, TonB-linked |
| TF1056 | HP-C |
| TF1207 | OM receptor, TonB-dependent |
| TF1206 | HP-C |
| TF1318 | OM receptor |
| TF1319 | Omp |
| TF1415 | Omp, TDR |
| TF1416 | Omp |
| TF1506-7[a] | OM receptor, TonB-dependent |
| TF1505 | HP-C |
| TF1535 | possible OM receptor protein |
| TF1534 | HP-C |
| TF1605 | Omp, TDR |
| TF1606 | Omp |
| TF1989 | Omp, possible TDR |
| TF1990 | Omp |
| TF2032 | Omp, TDR |
| TF2031 | HP-C |
| TF2193 | Omp, TDR |
| TF2192 | possible Omp |
| TF2301 | Omp, TDR |
| TF2302 | HP-C, possible Omp |
| TF2347-8[a] | Omp, possibly involved in nutrient binding |
| TF2349 | HP-C |
| TF2403 | Omp, TDR |
| TF2402 | Omp, possibly involved in nutrient binding |
| TF2412 | Omp |
| TF2411 | Omp |
| TF2417 | Omp, TDR |
| TF2416 | HP-C |
| TF2597 | OM receptor protein; possible TDR |
| TF2596 | HP-C, possible LP |
| TF2605 | Omp, TDR |
| TF2606 | HP-C |
| TF2725 | Omp, TDR |
| TF2726-7[a] | Omp, possibly involved in nutrient binding |
| TF2728 | Omp, TDR |
| TF2729 | possible Omp |
| TF2801 | Omp, TDR |
| TF2802 | possible Omp |
| TF3011 | Omp, TDR |
| TF3012 | possible Omp |
| TF3104 | Omp, TDR |
| TF3103 | Omp |
| TF_extra[h] | Not in LANL |
| TF0015 | Omp (possible immunogenic lipoprotein) |
| TF0090 | HP-C |
| TF0091 | Omp |
| TF0220 | HP-C |
| TF0304 | peptidyl-prolyl cis-trans isomerase |
| TF0305 | peptidyl-prolyl cis-trans isomerase |
| TF0322 | possible Yngk protein |
| TF0348 | HP |

TABLE F-continued

| Accession[a] | Protein Description[a], abbreviated[b] |
|---|---|
| TF0365 | HP |
| TF0368 | HP |
| TF0447 | HP |
| TF0546 | HP-C |
| TF0652 | HP-C |
| TF0661 | HP |
| TF0749 | protease II |
| TF0750 | HP-C |
| TF0765 | HP-C |
| TF0945 | HP-C; possible surface protein |
| TF1033 | endothelin converting enzyme, endopeptidase |
| TF1055 | HP |
| TF1158 | OM LP, NlpE involved in copper resistance |
| TF1342 | possible lipoprotein |
| TF1404 | HP-C |
| TF1440 | HP |
| TF1525 | HP-C |
| TF1565 | polysaccharide export protein, BexD/CtrA/VexA family |
| TF1733 | HP-C |
| TF1755 | periplasmic protease |
| TF1940 | TPR-repeat-containing protein |
| TF2016 | HP |
| TF2035 | HP-C |
| TF2206 | HP-C; possible sugar phosphate isomerase/epimerase |
| TF2207 | exo-alpha-sialidase (neuraminidase) |
| TF2214 | peptidyl-prolyl cis-trans isomerase |
| TF2327 | HP-C; possible lipoprotein |
| TF2414 | HP |
| TF2415 | HP |
| TF2447 | lipoprotein |
| TF2531 | possible dipeptidyl-peptidase III |
| TF2804 | HP-C |
| TF2806 | HP-C |
| TF2843 | HP-C; possible lipoprotein |
| TF2925 | beta-N-acetylglucosaminidase |
| TF3013 | HP-C |
| TF3024 | periplasmic protease |
| TF3165 | thiol: disulfide interchange protein |
| TF0955 | HP-C |
| TF1032 | possible internalin-related protein |
| TF1259 | HP |
| TF1741 | HP-C |
| TF1843 | surface antigen BspA** |
| TF2116 | HP-C; possible hemagglutinin/hemolysin |
| TF2320 | HP |
| TF2339 | HP |
| TF2592 | HP-C |
| TF2646 | HP-C |
| TF2661-2[a] | surface layer protein A |
| TF2663 | surface layer protein B |
| TF2998 | surface antigen BspA** |
| TF3080 | HP-C |
| TF3163 | HP-C |
| TF1478 | membrane fusion efflux protein |
| TF0454 | xanthine/uracil permease family protein |
| TF1351 | HP-C |
| TF1970 | oxaloacetate decarboxylase, beta-subunit |
| TF2574 | preprotein translocase SecY |
| TF0477 | dipeptide/tripeptide permease, POT family |
| TF0789 | preprotein translocase, secDF family |
| TF3036 | glucose/galactose transporter |
| TF0797 | HP-C |
| TF0813 | glycosyl hydrolase, secreted |
| TF1201 | possible preprotein translocase |
| TF1245 | LemA protein |
| TF2333 | signal peptidase I |
| TF2924 | DNA-binding response regulator/sensor histidine kinase |
| TF3099 | HP-C |
| TF0334 | HP |
| TF0743 | HP-C |
| TF1039 | HP-C |
| TF1101 | ABC transporter, ATP-binding protein |
| TF1964 | MotA/TolQ/ExbB proton channel family |
| TF0405 | HP-C |
| TF2920 | HP-C |
| TF3137 | Na+-translocating NADH-quinone reductase, subunit E |
| TF1413 | possible transmembrane protein |
| TF0959 | periplasmic protease |
| TF1775 | oxidoreductase, Gfo/Idh/MocA family |
| TF2330 | HP-C |
| TF1897 | HP-C, possible aminopeptidase |
| TF0421 | alpha-L-fucosidase |
| TF2803 | possible NADH-dependent dehydrogenase |
| TF0183 | HP-C |
| TF0216 | 50S ribosomal protein L20 |
| TF0217 | 50S ribosomal protein L35 |
| TF0439 | Na+-transporting NADH: ubiquinone oxidoreductase, subunit 1 |
| TF0841 | NADH dehydrogenase/NAD(P)H nitroreductase |
| TF1123 | glycosyltransferase |
| TF1150 | pyruvate-formate lyase |
| TF1151 | HP-C |
| TF1193 | glycosyl transferase, group 1 family |
| TF1325 | L-fucose isomerase |
| TF1575 | DNA-binding response regulator |
| TF1595 | HP-C |
| TF2190 | HP-C |
| TF2421 | cytocidal toxin protein |
| TF2551 | 30S ribosomal protein S10 |
| TF2552 | 50S ribosomal protein L3 |
| TF2560 | 30S ribosomal protein S3 |
| TF2566 | 50S ribosomal protein L5 |
| TF2569 | 50S ribosomal protein L6 |
| TF2579 | 30S ribosomal protein S4 |
| TF2649 | succinate dehydrogenase, flavoprotein subunit |
| TF2650 | succinate dehydrogenase, iron-sulfur subunit |
| TF2838 | HP-C |
| TF3006 | transcriptional regulator RprY |

[a]Accession numbers and protein descriptions are from the Oralgen website (www.oralgen-.lanl.gov) Hyphenated accession numbers are where two adjacent genes in the database correspond to a single protein as indicated by both proteomics and homology data.

Various adjuvants are known for use in conjunction with vaccine compositions. The adjuvants aid by modulating the immune response and in attaining a more durable and higher level of immunity using smaller amounts of vaccine antigen or fewer doses than if the vaccine antigen were administered alone. Examples of adjuvants include incomplete Freund's adjuvant (IFA), Adjuvant 65 (containing peanut oil, mannide monooleate and aluminium monostearate), oil emulsions, Ribi adjuvant, the pluronic polyols, polyamines, Avridine, Quil A, saponin, MPL, QS-21, mineral gels such as aluminium salts and calcium salts, nanoparticles such as hydroxyapatite, calcium phosphate, aluminium salts, sugar oligomers and polymers such as mannan, chitosan. Other examples include oil in water emulsions such as SAF-1, SAF-0, MF59, Seppic ISA720, and other particulate adjuvants such ISCOMs™ and ISCOM Matrix™. An extensive but not exhaustive list of other examples of adjuvants are listed in Cox and Coulter 1992 [In: Wong W K (ed.) *Animals parasite control utilising technology*. Bocca Raton; CRC press, 1992; 49-112]. In addition to the adjuvant, the vaccine composition may include conventional pharmaceutically acceptable carriers, excipients, fillers, buffers or diluents as appropriate. One or more doses of the vaccine composition containing adjuvant may be administered prophylactically to prevent periodontitis or therapeutically to treat already present periodontitis. In one embodiment, the adjuvant used would be selected to facilitate the production of a Th-2 biased response. An example would be Alum.

In a preferred composition, the chimeric or fusion protein is combined with a mucosal adjuvant and administered via the oral, buccal or nasal route. Examples of mucosal adjuvants are nanoparticles, cholera toxin and heat labile *E. coli* toxin, the non-toxic B subunits of these toxins, genetic mutants of these toxins which have a reduced toxicity.

Other methods which may be utilised to deliver the antigenic protein orally/buccally/nasally include incorporation or absorption of the protein into or onto particles of biodegradable polymer (such as acrylates or polyesters) or nanoparticles (such as hydroxyapatite) by microencapsulation to aid uptake of the microspheres from the gastrointestinal tract or other mucosal surfaces and to protect degradation of the proteins. Liposomes, ISCOMs™, hydrogels are examples of other potential methods which may be further enhanced by the incorporation of targeting molecules such as LTB, CTB or lectins for delivery of the antigenic protein to the mucosal immune system. In addition to the antigenic protein and the mucosal adjuvant or delivery system, the vaccine composition may include conventional pharmaceutically acceptable carriers, excipients, fillers, coatings, dispersion media, antibacterial or antifungal agents, and buffers or diluents as appropriate.

Many methods are known for administration of a vaccine composition to a subject, including but not limited to intradermal, intramuscular, intraperitoneal, intravenous, subcutaneous, intranasal, sub-lingual, buccal and oral administration. These routes of administration are particularly useful for vaccination.

In a further aspect, the present invention provides a nucleic acid molecule including a nucleotide sequence encoding a chimeric or fusion protein as broadly described above, optionally operatively linked to at least one regulatory element. In one embodiment the nucleic acid is provided in isolated or substantially purified form.

The nucleic acid molecule may, for example, be inserted into a suitable expression vector for production of the chimeric protein as a recombinant protein by insertion of the expression vector into a prokaryotic or eukaryotic host cell. Successful expression of the recombinant protein requires that the expression vector contains the necessary regulatory elements for transcription and translation which are compatible with, and recognised by the particular host cell system used for expression. A variety of host cell systems may be utilized to express the recombinant protein, which include, but are not limited to bacteria transformed with a bacteriophage vector, plasmid vector, or cosmid DNA; yeast containing yeast vectors; fungi containing fungal vectors; insect cell lines infected with virus (e.g. baculovirus); and mammalian cell lines transfected with plasmid or viral expression vectors, or infected with recombinant virus (e.g. vaccinia virus, adenovirus, adeno-associated virus, retrovirus, etc).

Using methods known in the art of molecular biology, various promoters and enhancers can be incorporated into the expression vector, to increase the expression of the recombinant protein, provided that the increased expression of the amino acid sequences is compatible with (for example, non-toxic to) the particular host cell system used.

The selection of the promoter will depend on the expression system used. Promoters vary in strength, i.e. ability to facilitate transcription. Generally, it is desirable to use a strong promoter in order to obtain a high level of transcription of the coding nucleotide sequence and expression into recombinant protein. For example, bacterial, phage, or plasmid promoters known in the art from which a high level of transcription have been observed in a host cell system including E. coli include the lac promoter, trp promoter, recA promoter, ribosomal RNA promoter, the $P_R$ and $P_L$ promoters, lacUV5, ompF, bla, Ipp, and the like, may be used to provide transcription of the inserted nucleotide sequence encoding amino acid sequences.

Other control elements for efficient transcription or translation include enhancers, and regulatory signals. Enhancer sequences are DNA elements that appear to increase transcriptional efficiency in a manner relatively independent of their position and orientation with respect to a nearby coding nucleotide sequence. Thus, depending on the host cell expression vector system used, an enhancer may be placed either upstream or downstream from the inserted coding sequences to increase transcriptional efficiency. Other regulatory sites, such as transcription or translation initiation signals, can be used to regulate the expression of the coding sequence.

In another embodiment, the vector may be a viral or bacterial vaccine vector, and used to provide a recombinant viral vaccine, a recombinant bacterial vaccine, a recombinant attenuated bacterial vaccine, or an inactivated recombinant viral vaccine. Vaccinia virus is the best known example, in the art, of an infectious virus that is engineered to express vaccine antigens derived from other organisms. The recombinant live vaccinia virus, which is attenuated or otherwise treated so that it does not cause disease by itself, is used to immunize the host. Subsequent replication of the recombinant virus within the host provides a continual stimulation of the immune system with the vaccine antigens thereby providing long lasting immunity.

Other live vaccine vectors include: adenovirus, cytomegalovirus, and preferably the poxviruses such as vaccinia [Paoletti and Panicali, U.S. Pat. No. 4,603,112] and attenuated Salmonella strains [Stocker et al., U.S. Pat. Nos. 5,210,035; 4,837,151; and 4,735,801; and Curtiss et al., 1988, Vaccine 6:155-160]. Live vaccines are particularly advantageous because they continually stimulate the immune system which can confer substantially long-lasting immunity. When the immune response is protective against subsequent P. gingivalis infection, the live vaccine itself may be used in a preventive vaccine against P. gingivalis. In particular, the live vaccine can be based on a bacterium that is a commensal inhabitant of the oral cavity. This bacterium can be transformed with a vector carrying a recombinant chimeric protein and then used to colonise the oral cavity, in particular the oral mucosa. Once colonised in the oral mucosa, the expression of the recombinant protein will stimulate the mucosal associated lymphoid tissue to produce neutralising antibodies. To further illustrate this embodiment, using molecular biological techniques well known in the art, nucleotide sequences encoding the chimeric proteins of this invention may be inserted into the vaccinia virus genomic DNA at a site which allows for expression of epitopes but does not negatively affect the growth or replication of the vaccinia virus vector. The resultant recombinant virus can be used as the immunogen in a vaccine formulation. The same methods can be used to construct an inactivated recombinant viral vaccine formulation except that the recombinant virus is inactivated, such as by chemical means known in the art, prior to use as an immunogen and without substantially affecting the immunogenicity of the expressed immunogen. The inactivated recombinant-vaccine may be formulated with a suitable adjuvant in order to enhance the immunological response to the vaccine antigens.

The invention also provides for the use of a nucleic acid molecule including a nucleotide sequence encoding a chimeric or fusion protein of this invention directly as the vaccine formulation. Nucleotide sequences encoding the chimeric proteins, operatively linked to one or more regulatory elements, can be introduced directly to vaccinate an individual ("direct gene transfer") against pathogenic strains of P. gingivalis. Direct gene transfer into a vaccinated individual, resulting in expression of the genetic material by the vaccinated individual's cells such as vascular endothelial cells as well as the tissue of the major organs, has been demonstrated by techniques in the art such as by injecting intravenously an expression plasmid:cationic liposome complex [Zhu et al., 1993, Science 261:209-211]. Other effective methods for delivering vector DNA into a target cell are known in the art. In one example, purified recombinant plasmid DNA containing viral genes has been used to inoculate (whether parenterally, mucosally, or via gene-gun immunization) vaccines to induce a protective immune response [Fynan et al. 1993, *Proc Natl Acad Sci USA* 90:11478-11482]. In another example, cells removed from an individual can be transfected or electroporated by standard procedures known in the art, resulting in the introduction of the recombinant vector DNA intro the target cell. Cells containing the recombinant vector DNA may then be selected for using methods known in the art, such as by use of a selection marker expressed in the vector, and the selected cells may then be re-introduced into the individual to express the recombinant protein.

In other embodiments there is provided a pharmaceutical composition including an anti-microbial agent and immunogen as described above. The composition may further include diluent, excipient, or carrier or chemotherapeutic agent for treatment of a condition or disease associated with oral infection and may be adapted for oral administration. The compositions of this invention may be incorporated in lozenges, or in chewing gum or other products, e.g. by stirring into a warm gum base or coating the outer surface of a gum base, illustrative of which are jelutong, rubber latex, vinylite resins, etc., desirably with conventional plasticizers or softeners, sugar or other sweeteners or such as glucose, sorbitol and the like.

An oral composition of this invention which contains the above-mentioned pharmaceutical composition may be prepared and used in various forms applicable to the mouth such as dentifrice including toothpastes, toothpowders and liquid dentifrices, mouthwashes, troches, chewing gums, dental pastes, gingival massage creams, gargle tablets, dairy products and other foodstuffs. An oral composition according to this invention may further include additional well known ingredients depending on the type and form of a particular oral composition.

In certain preferred forms of the invention the oral composition may be substantially liquid in character, such as a mouthwash or rinse. In such a preparation the vehicle is typically a water-alcohol mixture desirably including a humectant as described below. Generally, the weight ratio of water to alcohol is in the range of from about 1:1 to about 20:1. The total amount of water-alcohol mixture in this type of preparation is typically in the range of from about 70 to about 99.9% by weight of the preparation. The alcohol is typically ethanol or isopropanol. Ethanol is preferred.

The pH of such liquid and other preparations of the invention is generally in the range of from about 5 to about 9 and typically from about 5.0 to 7.0. The pH can be controlled with acid (e.g. citric acid or benzoic acid) or base (e.g. sodium hydroxide) or buffered (as with sodium citrate, benzoate, carbonate, or bicarbonate, disodium hydrogen phosphate, sodium dihydrogen phosphate, etc).

In other desirable forms of this invention, the pharmaceutical composition may be substantially solid or pasty in character, such as toothpowder, a dental tablet or a toothpaste (dental cream) or gel dentifrice. The vehicle of such solid or pasty oral preparations generally contains dentally acceptable polishing material.

In a toothpaste, the liquid vehicle may comprise water and humectant typically in an amount ranging from about 10% to about 80% by weight of the preparation. Glycerine, propylene glycol, sorbitol and polypropylene glycol exemplify suitable humectants/carriers. Also advantageous are liquid mixtures of water, glycerine and sorbitol. In clear gels where the refractive index is an important consideration, about 2.5-30% w/w of water, 0 to about 70% w/w of glycerine and about 20-80% w/w of sorbitol are preferably employed.

Toothpaste, creams and gels typically contain a natural or synthetic thickener or gelling agent in proportions of about 0.1 to about 10, preferably about 0.5 to about 5% w/w. A suitable thickener is synthetic hectorite, a synthetic colloidal magnesium alkali metal silicate complex clay available for example as Laponite (e.g. CP, SP 2002, D) marketed by Laporte Industries Limited. Laponite D is, approximately by weight 58.00% $SiO_2$, 25.40% MgO, 3.05% $Na_2O$, 0.98% $Li_2O$, and some water and trace metals. Its true specific gravity is 2.53 and it has an apparent bulk density of 1.0 g/ml at 8% moisture.

Other suitable thickeners include Irish moss, iota carrageenan, gum tragacanth, starch, polyvinylpyrrolidone, hydroxyethylpropylcellulose, hydroxybutyl methyl cellulose, hydroxypropyl methyl cellulose, hydroxyethyl cellulose (e.g. available as Natrosol), sodium carboxymethyl cellulose, and colloidal silica such as finely ground Syloid (e.g. 244). Solubilizing agents may also be included such as humectant polyols such propylene glycol, dipropylene glycol and hexylene glycol, cellosolves such as methyl cellosolve and ethyl cellosolve, vegetable oils and waxes containing at least about 12 carbons in a straight chain such as olive oil, castor oil and petrolatum and esters such as amyl acetate, ethyl acetate and benzyl benzoate.

It will be understood that, as is conventional, the oral preparations will usually be sold or otherwise distributed in suitable labelled packages. Thus, a bottle of mouth rinse will have a label describing it, in substance, as a mouth rinse or mouthwash and having directions for its use; and a toothpaste, cream or gel will usually be in a collapsible tube, typically aluminium, lined lead or plastic, or other squeeze, pump or pressurized dispenser for metering out the contents, having a label describing it, in substance, as a toothpaste, gel or dental cream.

Organic surface-active agents may be used in the compositions of the present invention to achieve increased prophylactic action, assist in achieving thorough and complete dispersion of the active agent throughout the oral cavity, and render the instant compositions more cosmetically acceptable. The organic surface-active material is preferably anionic, non-ionic or ampholytic in nature and preferably does not interact with the active agent. It is preferred to employ as the surface-active agent a detersive material which imparts to the composition detersive and foaming properties. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkylsulfo-acetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. Examples of water-soluble non-ionic surfactants suitable for use are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly(ethylene oxide) with fatty acids, fatty alcohols, fatty amides, polyhydric alcohols (e.g. sorbitan monostearate) and polypropyleneoxide (e.g. Pluronic materials).

The surface active agent is typically present in amount of about 0.1-5% by weight. It is noteworthy, that the surface active agent may assist in the dissolving of the active agent of the invention and thereby diminish the amount of solubilizing humectant needed.

Various other materials may be incorporated in the oral preparations of this invention such as whitening agents, preservatives, silicones, chlorophyll compounds and/or ammoniated material such as urea, diammonium phosphate, and mixtures thereof. These adjuvants, where present, are incorporated in the preparations in amounts which do not substantially adversely affect the properties and characteristics desired.

Any suitable flavouring or sweetening material may also be employed. Examples of suitable flavouring constituents are flavouring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, xylitol, sodium cyclamate, perillartine, AMP (aspartyl phenyl alanine, methyl ester), saccharine, and the like. Suitably, flavour and sweetening agents may each or together comprise from about 0.1% to 5% more of the preparation.

Compositions intended for oral use may be prepared according to any method known in the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract or periodontal pocket and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropyl methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate.

The aqueous suspensions may also contain one or more preservatives or antimicrobial agents, for example benzoates, such as ethyl, or n-propyl p-hydroxybenzoate another example is chlorhexidine gluconate, one or more colouring agents, one or more flavouring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide palatable oral preparations. These compositions may be preserved by the addition of an anti-oxidant such as ascorbic acid.

4. KITS

In certain embodiments there is provided a kit including:
anti-microbial agent for removing substantially all microorganisms or fragments thereof from oral tissue of said subject;
an immunogen for immunising said subject against a microbial pathogen, the presence of which in oral tissue is associated with a disease or condition;
said kit being adapted for use in the above described methods.
The kit may include:
a container holding a therapeutic composition in the form of one or more of an anti-microbial agent and immunogen;
a label or package insert with instructions for use.

In certain embodiments, there is provided a kit when used in a method or use described herein.

In certain embodiments the kit may contain one or more further active principles or ingredients for treatment of a disease or condition.

The kit may comprise a container and a label or package insert on or associated with the container. Suitable containers include, for example, bottles, vials, syringes, blister pack, etc. The containers may be formed from a variety of materials such as glass or plastic. The container holds a therapeutic composition which is effective for treating the condition and may have a sterile access port (for example the container may be an intravenous solution bag or a vial having a stopper pierceable by a hypodermic injection needle). The label or package insert indicates that the therapeutic composition is used for treating the condition of choice. In one embodiment, the label or package insert includes instructions for use and indicates that the therapeutic composition can be used for treatment of the given disease or condition.

The kit may comprise (a) a therapeutic composition; and (b) a second container with a second active principle or ingredient contained therein. The kit in this embodiment of the invention may further comprise a package insert indicating that the and other active principle can be used to treat a disorder or prevent a complication stemming from a given infection. Alternatively, or additionally, the kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The invention is further illustrated by the following Examples which are included by way of exemplification and not limitation of the invention.

Example 1

Methods and Materials

Bacterial Strains and Growth Conditions.

Lyophilised cultures of *Porphyromonas gingivalis* W50 were grown anaerobically at 37° C. on lysed horse blood agar plates supplemented with 5 µg/ml haemin, 0.5 µg/ml cysteine (HB agar, <10 passages). After 3-4 days colonies were used to inoculate brain heart infusion medium containing 5 µg/ml haemin, 0.5 µg/ml cysteine (1). Batch cultures were grown anaerobically in a MK3 Anaerobic Workstation (Don Whitley Scientific Ltd., Adelaide, Australia). Cells were harvested during exponential growth phase by centrifugation (7500 g, 30 min, 4° C.) and washed twice with PG buffer (50 mM Tris-HCl, 150 mM NaCl, 5 mM $CaCl_2$, and 5 mM cysteine-HCl, pH 8.0) in the anaerobic workstation. Growth of batch cultures was monitored at 650 nm using a spectrophotometer (model 295E, Perkin-Elmer). Culture purity was checked routinely by Gram stain, microscopic examination and using a variety of biochemical tests according to Slots (2).

Construction of pET28 Constructs Containing Adhesin Sequences and Adhesin Sequences with N-Terminal Addition of Kgp Proteinase Sequences.

Kgp residues representing peptides and chimeric peptides of the active site (AS) and KgpA1 adhesin (A1) domains were over-expressed in *E. coli* as recombinant (r) proteins with hexa-His tags (SEQ ID NO: 93) using pET expression vectors (Novagen). The r-proteins expressed were rKAS2, and rKLA1 and the r-chimeric proteins were rKAS2-KLA1, rKAS1-KsA1 and rKAS4-KAS3-KAS5-KAS6-KLA1 (also referred to as multiKAS-KLA1). The amino acid sequences representing the various A1 and AS domains are described in Tables 1 and 2.

The various KAS and KA1 domains of the kgp gene were amplified from pNS1 (3.5 kb BamHI lys fragment in pUC18) or *P. gingivalis* genomic DNA respectively using primers listed in Table 4, Taq DNA polymerase (Invitrogen) and a PC-960 thermal cycler (Corbett Research Technologies). Primer pairs KAS2-FOR and KAS2-REV and KLA1-FOR and KLA1-REV were used to generate PCR fragments encoding KAS2 and KLA1 respectively using the following reaction conditions: 94° C., 3 minutes, followed by 28 cycles of 94° C., 45 sec (denaturing); 62° C., 40 seconds (annealing) and 72° C., 20 seconds (extension) followed by a final cycle of 72° C., 5 min.

The KAS2-KLA1 chimeric PCR product was produced by gene splicing by overlap extension (SOEing) as follows: PCR products were produced using primer pairs KAS2-FOR and KAS2-KLA1-chimera-REV and KAS2-KLA1-chimera-FOR and KLA1-REV using the conditions described above. The PCR products were then annealed and a final PCR was performed with primers KAS2-FOR and KLA1-REV (94° C., 2 minutes, followed by 28 cycles of 94° C., 30 sec; 50° C., 30 seconds and 72° C., 40 seconds followed by a final cycle of 72° C., 5 min.

For the preparation of the KAS1-KsA1 PCR product, two successive PCRs were conducted using the KAS1-KsA1-REV primer with each of the KAS1-KsA1-FOR primers 1 and, 2 in succession (reaction conditions 94° C. for 2 minutes followed by 35 cycles of 94° C., 15 seconds; 63° C., 30 seconds and 72° C., 2 minutes) to produce the KAS1-KsA1 PCR product. The KAS1-KsA1-FOR1 and KAS1-KsA1-FOR2 primers contain an 3' extension overlapping the 5' of the previous PCR product.

For the preparation of the multiKAS-KLA1 PCR fragment, four successive PCR's were conducted using the multi-REV primer with each of the multi-FOR primers 1, 2, 3 and 4 in succession (reaction conditions were 95° C., 2 minutes followed by 35 cycles of 95° C., 20 seconds; 68° C., 1.5 minutes) to produce the multiKAS-KLA1 PCR product. Each multi-FOR primer contains a 3' extension overlapping the 5' of the previous PCR product.

All of the PCR fragments encoding KAS2, KLA1, KAS2-KLA1, KAS1-KsA1 and multiKAS-KLA1, were purified using PCR purification columns (Qiagen), ligated into the TA cloning vector, pGem-T Easy (Promega) and transformed into *E. coli* JM109 following the manufacturer's protocol. Purified recombinant pGemT-Easy constructs were digested with NcoI and XhoI and directionally cloned into NcoI/XhoI digested pET28b (Novagen) and transformed into the non-expression host, *E. coli* JM109 [DH5a]. The recombinant pET28 constructs were purified and transformed into the *E. coli* expression host, BL21 (DE3) [HMS174(DE3)] (Novagen) and selected on LB containing 50 µg kanamycin following the manufacturer's instructions. The integrity of each insert was confirmed by DNA sequence analysis.

The oligonucleotide primers (Table 4) have been designed to incorporate restriction enzyme sites, stop codons and hexa-His Tags (SEQ ID NO: 93) where necessary. The primers used for the rKAS2, rKLA1 and rKAS2-KLA1 were designed to limit the inclusion of extraneous coding sequence to no more than three amino acids plus the hexa-his tag (SEQ ID NO: 93) in r-proteins. The rKAS1 and the rKLA1 were designed to contain a hexa-His tag (SEQ ID NO: 93) at the N-terminal and C-terminal ends respectively, so that they may be directly compared to the rKAS2-KLA1 which has a hexa-his tag (SEQ ID NO: 93) at both N- and C-termini. In rKAS1-KsA1 and rmultiKAS-KLA1 the His Tags are found at the C-termini.

Table 4 Oligonucleotide primers used for the amplification of the nucleotide sequences encoding the various fragments and chimeras of Kgp A1 and AS. Table 4 discloses "$(His)_6$" as SEQ ID NO: 93.

TABLE 4

Oligonucleotide primers used for the amplification of the nucleotide sequences encoding the various fragments and chimeras of Kgp A1 and AS. Table 4 discloses "$(His)_6$" as SEQ ID NO: 93.

| Recombinant (r) protein | Oligo | Sequence (5'-3') | Characteristics* (5'-3') |
|---|---|---|---|
| rKAS2 | KAS2-FOR | GACCATGGCTCATCACCATCACC ATCACAATACCGGAGTCAGCTTT GCA (SEQ ID NO: 47) | GA buffer-NcoI (including ATG start)-CT-$(His)_6$-AS (nt 1992-2012) |

TABLE 4-continued

Oligonucleotide primers used for the amplification of the nucleotide sequences encoding the various fragments and chimeras of Kgp A1 and AS.
Table 4 discloses "(His)₆" as SEQ ID NO: 93.

| Recombinant (r) protein | Oligo | Sequence (5'-3') | Characteristics* (5'-3') |
|---|---|---|---|
| | KAS2-REV | GACTCGAGTTATTTGTCCTTATTA GTGAGTGCTTTC (SEQ ID NO: 48) | GA buffer-XhoI-TTA Stop-KAS1 (nt 2099-2075) |
| rKLA1 | KLA1-FOR | GACCATGGCTTGGGGAGACAATA CGGGTTAC (SEQ ID NO: 49) | GA buffer-NcoI (including ATG start)-CT-A1 (nt 2946-2966) |
| | KLA1-REV | GACTCGAGACCTCCGTTAGGCAA ATCC (SEQ ID NO: 50) | GA buffer-XhoI-A1 (nt 3863-3845) |
| rKAS2-KLA1 | KAS2-KLA1-REV | CCGTATTGTCTCCCCATTTGTCCT TATTAGTGAGTGCTTTC (SEQ ID NO: 51) | A1 (nt 2961-2946)-KAS1 (nt 2099-2075) |
| | KAS2-KLA1-FOR | CACTAATAAGGACAAATGGGGAG ACAATACGGGTTAC (SEQ ID NO: 52) | KAS1 (nt 2084-2099)-A1 (nt 2946-2966) |
| rKAS1-KsA1 | KAS1-KsA1-FOR1 | CATGGATCTGAGACCGCATGGG CTGATCCACTTTTCTTGTTGGATG CCGAT (SEQ ID NO: 53) | AS (nt 2025-2057)-A1 (nt 2970-2987)- |
| | KAS1-KsA1-FOR2 | CCATGGCTTTGAATACCGGAGTC AGCTTTGCAAACTATACAGCGCA TGGATCTGAGACCGCA SEQ ID NO: 54) | NcoI-CT-AS (nt 1989-2042) |
| | KAS1-KsA1-REV | CTCGAGGAATGATTCGGAAAGTG TT (SEQ ID NO: 55) | XhoI-A1(nt 3663-3644) |
| rmultiKAS-KLA1 | multi-FOR1 | CCATGGCTGATTATAGCTGGAAT TCCCAGGTAGTCAGCTTTGCAAA CTATACA (SEQ ID NO: 56) | NcoI-CT-KAS4 (nt 1857-1880)-KAS3 (nt 2001-2021) |
| | multi-FOR2 | CTTTGCAAACTATACAGCGCATG GATCTGAGACCGCATGGGCTGAT CCACTT (SEQ ID NO: 57) | KAS3 (nt 2006-2057) |
| | multi-FOR3 | ATGGGCTGATCCACTTCTGAATT CTTATTGGGGCGAGATCGGCAAT ATTACC (SEQ ID NO: 58) | KAS3 (nt 2042-2060)-KAS5 (nt 2223-2240)-KAS6 (nt 2403-2417) |
| | multi-FOR4 | GATCGGCAATATTACCCATATTG GTGCTCATTACGCTTGGGGAGAC AATACG (SEQ ID NO: 59) | G-KAS6 (nt 2403-2435)-GCT (Ala spacer)-A1(nt 2946-2960) |
| | multi-REV | CTCGAGACCTCCGTTAGGCAAAT CCAATGCCGGTGTTATCAGATAG TTGTCA (SEQ ID NO: 60) | Xho-A1 (nt 3863-3818) |

*nucleotide (nt) sequence numbers from lysine-specific cysteine proteinase gene sequence accession number U75366

Expression and Purification of Recombinant Proteins.

Recombinant proteins were expressed from pET28::KLA1 (KAS2, KAS2-LA1, KAS1-SA1, multiKAS-KLA1) constructs by induction with isopropyl β-D-thiogalactosidase (IPTG). All recombinant proteins were produced as 6-His Tag (SEQ ID NO: 93) fusion proteins and purified with NI-NTA purification system (Invitrogen) under denaturing conditions. Briefly, E. coli (DE3) single colony transformants were used to inoculate 20 mL of Luria-Bertani (LB) broth containing 50 µg/ml kanamycin at 37° C. on an orbital shaker overnight. This inoculum was then used to inoculate 1L of LB containing 50 µg/ml kanamycin. The OD600 of this culture was allowed to reach 0.5-0.7 (mid-log phase) before inducing protein expression with isopropyi IPTG at 0.1 mM for 2 hours at 37° C. with shaking of 200 rpm. Cells were harvested (7,500 g) and resuspended in a denaturing binding buffer (8M Urea, 20 mM Sodium Phosphate pH 8.0 & 500 mM NaCl) and sonicated on ice for 3×15 s bursts at 30 s intervals using a Branson Sonifer 250 Cell disrupter (Branson Ultronics Corporation, Danbury, Conn.) with the microtip on setting 3, then centrifuged at 39,000 g for 30 min at 4° C. Recombinant proteins were purified from the supernatant by loading onto a pre-equilibrated Ni-NTA Agarose column and then washing with denaturing washing buffer (8M Urea, 20 mM Sodium Phosphate pH 6.0 & 500 mM NaCl) to elute unbound proteins. The column was then washed using 10 volumes of binding buffer B and the recombinant protein was eluted with denaturing elution buffer (8M Urea, 20 mM Sodium Phosphate pH 6.0, 500 mM NaCl & 0.5 M Imidazole). Purified protein was dialyzed against 2M Urea-PBS and stored at −80° C.

Recombinant protein samples were analysed by SDS-PAGE and their molecular masses determined using ProtParam on-line (http://au.expasy.org/tools/protparam.html). Protein concentration of all samples was determined by the Bio-Rad Protein Assay using BSA as a standard.

Immunisation and the Mouse Periodontitis Model.

The mouse periodontitis experiments were performed as described previously (3) and were approved by the University of Melbourne Ethics Committee for Animal Experimentation. BALB/c mice 6-8 weeks old (12 mice per group) housed in microisolators were immunized subcutaneously (s.c. 100 μL) with either 50 μg of one of the recombinant proteins or RgpA-Kgp complex, $2 \times 10^9$ formalin killed cells of $P.$ $gingivalis$ strain W50 or PBS; each antigen was emulsified in incomplete Freund's adjuvant (IFA). After 30 days the mice were boosted with antigen (s.c. injection, emulsified in IFA) and then bled from the retrobulbar plexus 12 days later. Four days after the second immunisation mice were given kanamycin (Sigma-Aldrich, New South Wales, Australia) at 1 mg/ml in deionized water ad libitum for 7 days. Three days after the antibiotic treatment (2 days after bleeding), mice were orally inoculated four times 2 days apart with $1 \times 10^{10}$ viable $P.$ $gingivalis$ W50 (25 μl) in PG buffer (50 mM Tris-HCl, 150 mM NaCl, 5 mM $CaCl_2$, and 5 mM cysteine-HCl, pH 8.0) containing 2% (wt/vol) carboxymethyl cellulose (CMC; Sigma-Aldrich, New South Wales, Australia), and a control group was sham infected with PG buffer containing 2% (wt/vol) CMC alone. The inocula were prepared in the anaerobic chamber and then immediately applied to the gingival margin of the maxillary molar teeth. Two weeks later, mice received another four doses (2 days apart) of $1 \times 10^{10}$ cells of viable $P.$ $gingivalis$ W50 (25 μl) in PG buffer containing 2% (wt/vol) CMC. The number of viable bacteria in each inoculum was verified by enumeration on blood agar. Mice were fed a soft powdered diet (Barastock, Australia) and housed in cages fitted with a raised wire mesh bottom to prevent access to bedding. Four weeks after the last dose, mice were bled from the retrobulbar plexus and killed, and the maxillae were removed and cut in half with one half (right) used for alveolar bone loss measurement and the other half (left) used for real-time PCR.

The right half maxillae were boiled (1 min) in deionized water, mechanically defleshed, and immersed in 2% (wt/vol) potassium hydroxide (16 h, 25° C.). The half maxillae were then washed (two times with deionized water) and immersed in 3% (wt/vol) hydrogen peroxide (6 h, 25° C.). After the half maxillae were washed (two times with deionized water), they were stained with 0.1% (wt/vol) aqueous methylene blue, and a digital image of the buccal aspect of each half maxilla was captured with an olympus DP12 digital camera mounted on a dissecting microscope, using OLYSIA BioReport software version 3.2 (Olympus Australia Pty Ltd., New South Wales, Australia) to assess horizontal bone loss. Horizontal bone loss is loss occurring in a horizontal plane, perpendicular to the alveolar bone crest (ABC) that results in a reduction of the crest height. Each half maxilla was aligned so that the molar buccal and lingual cusps of each tooth image were superimposed, and the image was captured with a micrometer scale in frame, so that measurements could be standardized for each image. The area from the cementoenamel junction to the ABC for each molar tooth was measured using OLYSIA BioReport software version 3.2 imaging software. Bone loss measurements were determined twice by a single examiner using a randomized and blinded protocol.

Determination of Subclass Antibody by an ELISA.

To determine the subclass antibody responses of mouse sera, enzyme-linked immunosorbent assays (ELISAs) were performed in triplicate using a 5-μg/ml solution of formalin killed $P.$ $gingivalis$ W50 in phosphate-buffered saline (PBS) (0.01 M $Na_2HPO_4$, 1.5 mM $KH_2PO_4$, 0.15 M NaCl), pH 7.0, containing 0.1% (vol/vol) Tween 20 (PBST) to coat wells of flat-bottom polyvinyl microtiter plates (Dynatech Laboratories, McLean, Va.). After removal of the coating solution, PBST containing 2% (wt/vol) skim milk powder was added to wells to block the uncoated plastic for 1 h at room temperature. After the wells were washed four times with PBST, serial dilutions of mouse sera in PBST containing 0.5% (wt/vol) skim milk (SK-PBST) were added to each well and incubated for 16 h at room temperature. After the wells were washed six times with PBST, a 1/2,000 dilution of goat IgG to mouse IgM, IgA, IgG1, IgG2a, IgG2b, or IgG3 (Sigma, New South Wales, Australia) was added in SK-PBST and allowed to bind for 2 h at room temperature. Plates were washed six times in PBST, and a 1/5,000 dilution of horseradish peroxidase-conjugated rabbit anti-goat immunoglobulin (Sigma, New South Wales, Australia) in SK-PBST was added to each well and incubated for 1 h at room temperature. After the wells were washed six times with PBST, bound antibody was detected by the addition of 100 μl of ABTS substrate [0.9 mM 2,2'-azino-bis(3-ethylbenz-thiazoline-6) sulfonic acid in 80 mM citric acid containing 0.005% (vol/vol) hydrogen peroxide, pH 4.0] to each well. The optical density at 415 nm was measured using a microplate reader (Bio-Rad microplate reader, model 450).

SDS-PAGE Gel Electrophoresis and Western Blotting.

Recombinant proteins (10 μg) were analysed using the XCell surelock Mini-Cell electrophoresis system. Recombinant proteins were mixed in 20 μl of reducing sample buffer (10% [wt/vol] SDS, 0.05% [wt/vol] bromophenol blue, 25% [vol/vol] glycerol, and 0.05% [vol/vol] 2-mercaptoethanol). The pH was adjusted to pH 8.0 with 1.5 M Tris-HCl, and then the solution was heated for 5 min at 100° C. Recombinant proteins (10 μg/lane) were loaded onto Novex 12% (wt/vol) Tris-glycine precast mini gels, and electrophoresis was performed using a current of 30 to 50 mA and a potential difference of 125 V using a Novex electrophoresis system (Novex, San Diego, Calif.). Proteins were visualized using 0.25% w/v Coomassie blue R250.

Epitope Analysis of the Kgp Proteinase Active Site Peptide (KAS-2) Sequence.

The antibody binding sites for the Lys-specific proteinase active site peptide KAS2 (433-468 SEQ ID No: 28) was determined by synthesising N-terminally biotinylated overlapping eight residue peptides (offset by one, overlapping by seven residues) on a multipin peptide synthesis system (Chiron Technologies, Melbourne, Australia) using standard solid-phase peptide synthesis protocols for Fmoc chemistry. Biotinylated peptides (5 μg/mL) in 0.1 M PBS, pH 7.4 were bound to strepavidin coated plates, overnight at 4° C. (Nunc, NSW Australia). After the wells were washed four times with PBST epitope mapping of the plate-bound peptides was carried out by ELISA as per Chiron Technologies instructions using mouse sera at a dilution of 1:1000 in 1% w/v non-fat skim milk powder in 0.1 M PBS, pH 7.4, containing 0.1% v/v Tween 20 (SK-PBST). After the wells were washed six times with PBST, a 1/2,000 dilution of goat IgG to mouse IgG (Sigma, New South Wales, Australia) was added in SK-PBST and allowed to bind for 2 h at room temperature. Plates were washed six times in PBST, and a 1/5,000 dilution of horseradish peroxidase-conjugated rabbit anti-goat immunoglobulin (Sigma, New South Wales, Australia) in SK-PBST was added to each well and incubated for 1 h at room temperature. After the wells were washed six times with PBST, bound antibody was detected by the addition of 100 µl of ABTS substrate [0.9 mM 2,2'-azino-bis(3-ethylbenz-thiazoline-6) sulfonic acid in 80 mM citric acid containing 0.005% (vol/vol) hydrogen peroxide, pH 4.0] to each well. The optical density at 415 nm was measured using a microplate reader (Bio-Rad microplate reader, model 450).

Statistical Analysis.

The bone loss data were statistically analyzed using a one-way analysis of variance (ANOVA) and Dunnett's T3 test (SPSS for Windows, version 12). The IgA, IgM, and IgG subclass antibody titers were statistically analyzed using Student's t test using SPSS software (SPSS for Windows, version 12).

Example 2

Characterisation and Purification of the Recombinant Proteins (KSA1, KLA1, KAS1-KsA1 and KAS2-KLA1)

Figure 2:
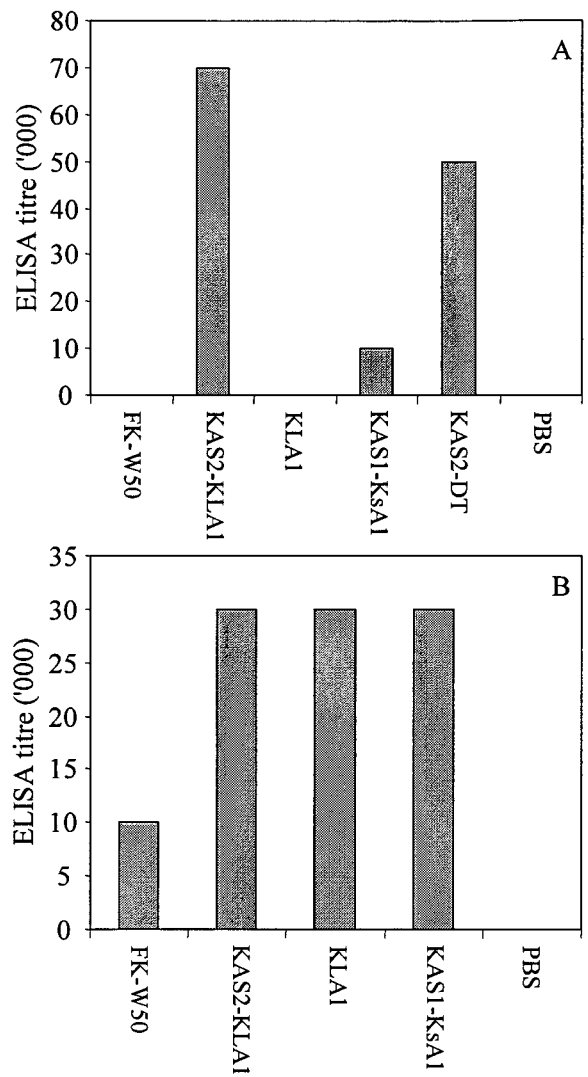
FIG. 2 shows antibody recognition of KAS2 peptide and formalin killed *P. gingivalis* W50 cells. (A) KAS2 peptide was probed with antisera raised to formalin killed *P. gingivalis* W50 cells (FK-W50), recombinant proteins KAS1-KsA1, KAS2-KLA1, and synthetic KAS2-DT conjugate and PBS in an ELISA. (B) formalin killed *P. gingivalis* W50 cells were probed with antisera raised to formalin killed *P. gingivalis* W50 cells (FK-W50), recombinant proteins KAS1-KsA1, KAS2-KLA1, KLA1 and PBS in an ELISA. Antibody responses are expressed as the ELISA titer $OD_{415}$ obtained minus double the background level, with each titer representing the mean±standard deviation of three values.

In order to characterise the ability of Kgp adhesin A1 domain fragments and chimera Kgp proteinase and Kgp adhesin A1 domain fragments to protect against *P. gingivalis* infection, we expressed and purified the recombinant proteins:—KsA1, KLA1, KAS1-KsA1 and KAS2-KLA1. Recombinant proteins (KsA1 and KLA1) and recombinant chimera proteins (KAS1-KsA1 and KAS2-KLA1) were purified from inclusion bodies using nickel chelate affinity chromatography and the purified proteins analysed by SDS-PAGE (FIG. 1). Each of the purified recombinant proteins consisted of one major protein band with molecular weights of 40, 36, 31 and 32 kDa corresponding to KAS2-KLA1, KLA1, KsA1 and KAS1-KsA1, and these weights corresponded to the calculated molecular masses of the His-tag recombinant proteins using ProtParam. To characterize the immunogenicity of the recombinant proteins KsA1, KLA1, KAS1-KsA1 and KAS2-KLA1 were used to immunize mice and the sera was used to probe KAS2 peptide coated plates and formalin killed *P. gingivalis* W50 cells coated plates (FIG. 2). Recombinant chimera proteins KAS1-KsA1 and KAS2-KLA1 antisera were found to recognize KAS2 peptide (FIG. 2A) at a similar level to KAS2 specific antisera (KAS2-diptheria toxoid conjugate) as well as formalin killed *P. gingivalis* W50 cells (FIG. 2B). However, antisera against the recombinant protein KLA1 only recognized killed *P. gingivalis* W50 cells (FIG. 2B).

Example 3

Figure 3:
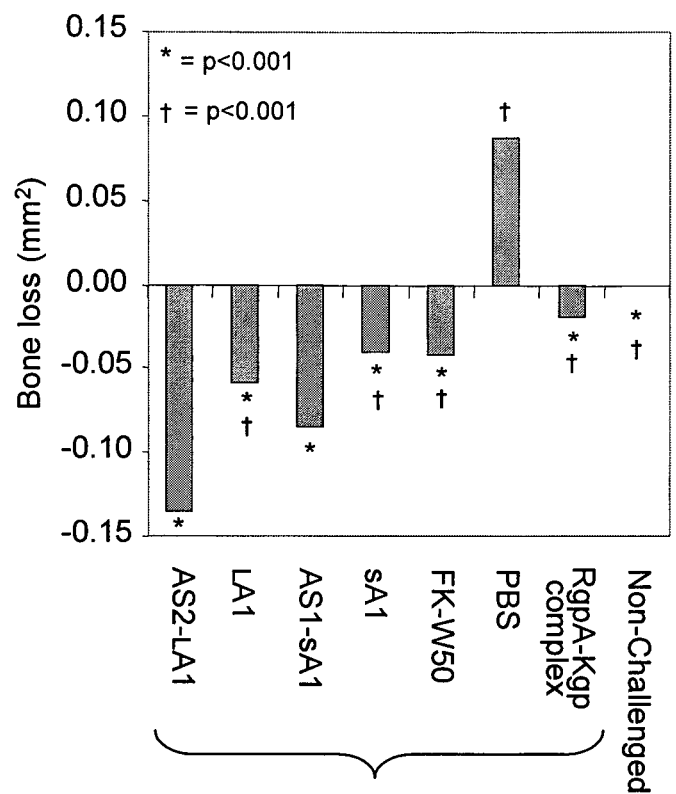
FIG. 3 shows *P. gingivalis*-induced horizontal bone loss of maxillae molars of mice immunised with the recombinant proteins and recombinant chimera proteins, formalin-killed *P. gingivalis* and adjuvant alone (PBS, IFA) or non-orally infected (non-challenged) mice. In this figure KAS2-KLA1 is shown as AS2-LA1, KLA1 is shown as LA1, KAS1-KsA1 is shown as AS1-sA1, KsA1 is shown as sA1. Measurement of bone loss is the mean of the area measured in millimeters squared (mm2) from the cementoenamel junction (CEJ) to the alveolar bone crest (ABC) of the buccal side of each maxillary molar of both the left and right maxillae. Data was normally distributed as measured by Levene's homogeneity of variance and are presented as mean (n=12) in mm2 and were analyzed using the One-Way analysis of variance and Dunnett's T3 test. *, indicates group has significantly (P<0.001) less bone loss than control (infected) group. †, indicates group has significantly (P<0.001) more bone loss than the AS2-LA1 group.

Effect of Immunization with the Recombinant Proteins (KSA1, KLA1, KAS1-KSA1 and KAS2-KLA1) on *P. gingivalis* Induced Alveolar Bone Loss in the Mouse Periodontitis Model The recombinant proteins KsA1, KLA1, KAS1-KsA1 and KAS2-KLA1, formalin killed *P. gingivalis* strain W50 and the RgpA-Kgp complex were used to determine and compare the protection induced against *P. gingivalis* induced alveolar bone loss using a modified mouse model of periodontal bone loss based on that reported by Baker et al (4). Mice were immunized (days 0 and 30) with either recombinant proteins KsA1, KLA1, KAS1-KsA1 or KAS2-KLA1, RgpA-Kgp complex or formalin killed *P. gingivalis* strain W50 (FK-W50) cells or PBS adjuvant alone and were then orally challenged with viable *P. gingivalis* W50. Immunization with all of the recombinant antigens, RgpA-Kgp complex and FK-W50 cells protected BALB/c mice against *P. gingivalis-induced* alveolar bone loss as these animals exhibited significantly ($p<0.001$) less bone loss compared to the PBS immunized group (FIG. 3). However the KAS2-KLA1 immunised mice had significantly less bone loss than mice immunised with KLA1 ($p<0.01$); KsA1 ($p<0.001$), RgpA-Kgp complex ($p<0.001$), FK-W50 cells ($p<0.001$) and non-challenged mice ($p<0.001$). There was no significant difference in bone loss between the KAS2-KLA1 and KAS1-KsA1 immunised mice. Furthermore, KAS1-KsA1 immunised mice exhibited significantly less bone loss than non-challenged mice ($p<0.01$) and RgpA-Kgp complex immunised mice ($p<0.05$), but were not significantly different from KsA1, KLA1, and FK-W50 immunised mice. There was no significant difference in bone loss between the KsA1, KLA1, RgpA-Kgp complex and FK-W50 immunised mice.

Example 4

Figure 4:
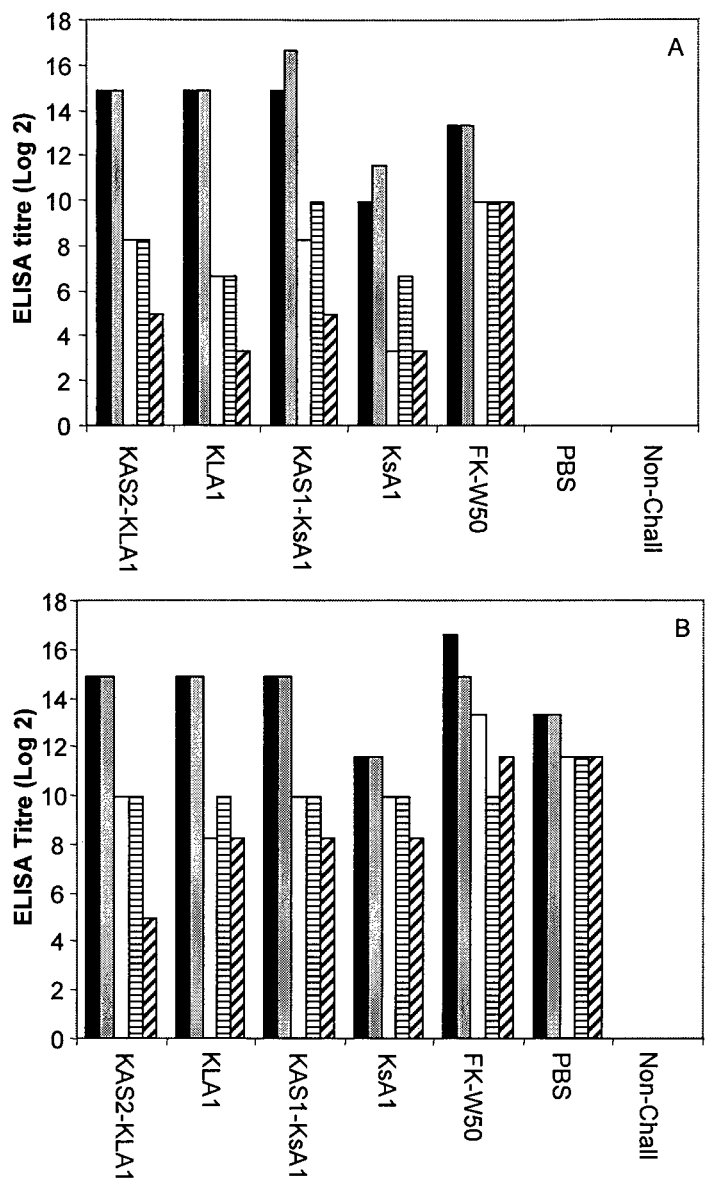
FIG. 4 shows serum antibody subclass responses of immunised mice in the periodontitis model. Sera from mice; A (pre-oral inoculation) and B (post-oral inoculation) immunised with recombinant proteins KsA1, KLA1, KAS1-KsA1 and KAS2-KLA1 and formalin killed P. gingivalis strain W50 were used in the ELISA with the formalin killed P. gingivalis strain W50 as the adsorbed antigen. Antibody responses IgG (black bars), IgG1 (grey bars), IgG2a (white bars), IgG2b (horizontal striped bars), IgG3 (diagonal striped bars), are expressed as the ELISA titer (log 2) obtained minus the background level, with each titer representing the mean±standard deviation of three values.

Antibody Subclass Responses Induced by Immunization with the Recombinant Proteins (KsA1, KLA1, KAS1-KsA1 and KAS2-KLA1) in the Mouse Periodontitis Models Prior and post to oral inoculation challenge with viable *P. gingivalis* cells mice were bled and the sera collected by centrifugation. FIG. 4 shows the antibody subclass reactivity to formalin-killed *P. gingivalis* W50 cells for each immunogen (KsA1, KLA1, KAS1-KsA1 or KAS2-KLA1 or formalin killed *P. gingivalis* strain W50 (FK-W50) cells) in the mouse periodontitis model. All of the protective immunogens induced a high IgG antibody titer to FK-W50. Furthermore, the predominant antibody subclass each protective immunogen induced was IgG1 with only weakly immunoreactive IgG2a, IgG2b and IgG3 FK-W50-specific antibodies (FIG. 4). The predominant antibody subclass induced by each immunogen both pre (FIG. 4A) and post-oral inoculation (FIG. 4B) was IgG1.

Example 5

Epitope Mapping of KAS2 (433-468).

Figure 5:
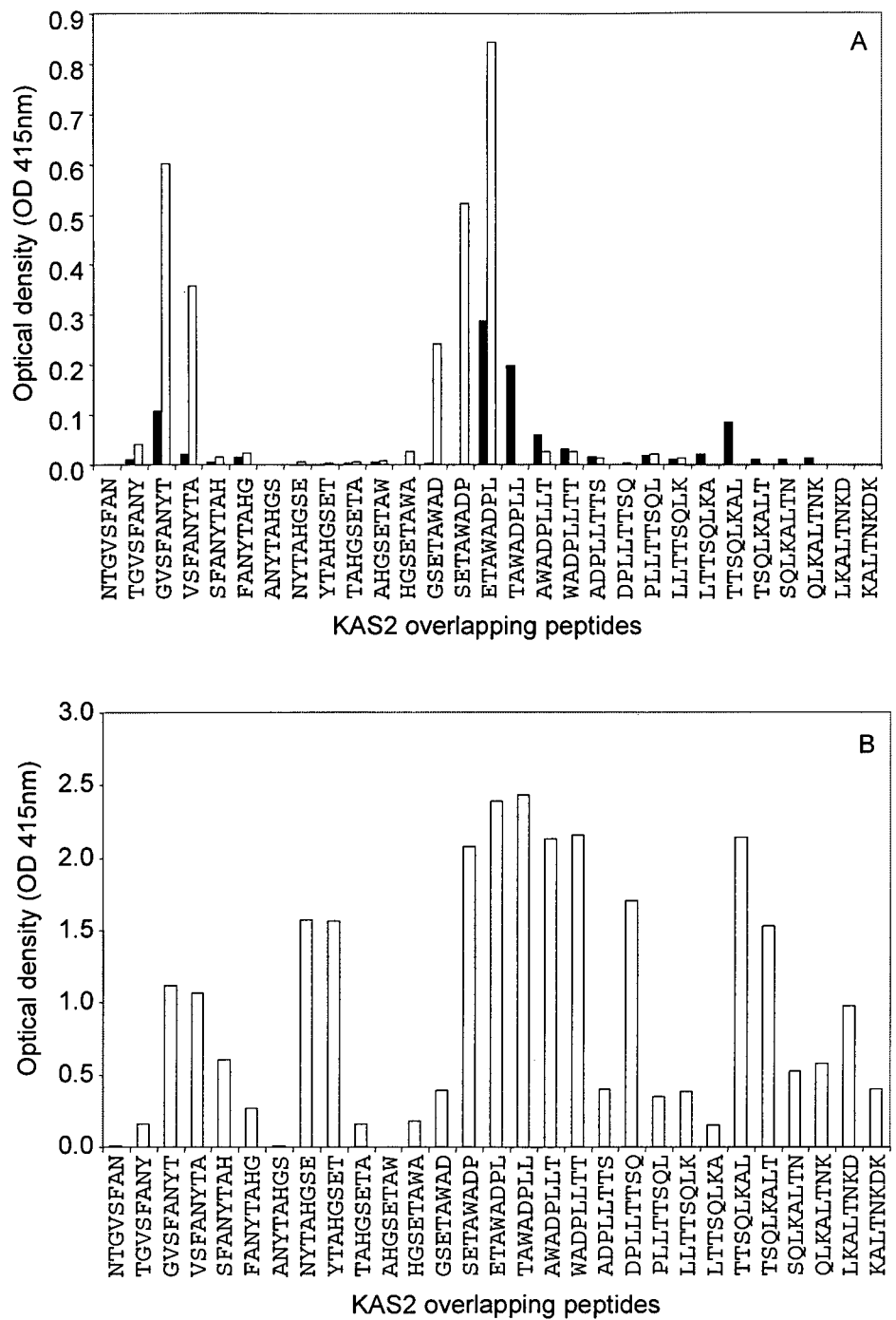
FIG. 5 shows a PEPSCAN analysis of peptide-specific antibody reactivity to overlapping peptides representing the KAS2 peptide sequence 433-468. (A) KAS2 overlapping peptides (SEQ ID NOS 94-95, 5, 7, 96-103, 19, 21, 23, 25 and 104-116, respectively, in order of appearance) (offset 1, overlap 7) probed with KAS1-KsA1 (white bars), KAS2-KLA1 (black bars) antisera. (B) KAS2 overlapping peptides (SEQ ID NOS 94-95, 5, 7, 96-103, 19, 21, 23, 25 and 104-116, respectively, in order of appearance) (offset, overlap 7) probed with KAS2-DT conjugate antisera. Each bar displays the antibody reactivity (optical density [OD] at 415 nm).

Overlapping biotinylated eight residue peptides (offset by one, overlap by seven) for KAS2 (433-468) were synthesised and used to coat streptavidin coated plates. The antibody binding epitopes were then identified using antisera from mice immunized with KAS1-KsA1, KAS2-KLA1 and KAS2-diphtheria toxoid conjugate (FIG. 5). A two fold increase in optical density (415 nm) above background was considered as a positive antibody response (threshold OD). The antisera recognised the following peptide sequences derived from SEQ ID No. 28 viz. KAS1-KsA1 recognised peptides 435-442, 436-443, 445-452, 446-453 and 447-454 (threshold OD=0.07, FIG. 5A) whereas KAS2-KLA1 recognised peptides 435-442, 447-454 and 448-455 (threshold ID=0.07, FIG. 5A). This suggests recognition of a number of minimal epitopes viz. peptide 436-442 (VSFANYT (SEQ ID NO: 3) and its variant VGFANYT (SEQ ID NO: 4)), peptide 447-452 (ETAWAD (SEQ ID NO: 9) and its variant ETSWAD (SEQ ID NO: 10)), and peptide 448-453 (TAWADP (SEQ ID NO: 11) and its variant TSWADP (SEQ ID NO: 12)). Peptides which include the peptide 436-442 epitope include GVSFANYT (SEQ ID NO: 5), GVGFANYT (SEQ ID NO: 6), VSFANYTA (SEQ ID NO: 7) and VGFANYTA (SEQ ID NO: 8). Peptides which include the peptide 447-452 and/or 448-453 epitopes include SETAWAD (SEQ ID NO: 13), SETSWAD (SEQ ID NO: 14), ETAWADP (SEQ ID NO: 15), ETSWADP (SEQ ID NO: 16), TAWADPL (SEQ ID NO: 17) and TSWADPL (SEQ ID NO: 18), more particularly GSETAWAD (SEQ ID NO: 19), GSETSWAD (SEQ ID NO: 20), SETAWADP (SEQ ID NO: 21), SETSWADP (SEQ ID NO: 22), ETAWADPL (SEQ ID NO: 23), ETSWADPL (SEQ ID NO: 24), TAWADPLL (SEQ ID NO: 25) and TSWADPLL (SEQ ID NO: 26.

Example 6

Synthesis of KAS and RAS Peptides for Conjugation to a Protein

Peptides were synthesized manually or using a CEM Microwave peptide synthesizer. Standard solid-phase peptide synthesis protocols for Fmoc chemistry were used throughout. Peptides were assembled as the carboxyamide form using Rink-linker derived AM-sure resin (AAPPTEC, KY, USA). Coupling was accomplished with HBTU/HOBt activation using 4 equiv of Fmoc-amino acid and 6 equiv of DIPEA. The Fmoc group was removed by 20% piperidine in 1M HOBt/DMF.

Resins bearing KAS or RAS peptides were swollen in DMF and the N-terminal Fmoc group removed by 2% v/v DBU in DMF containing 2% v/v piperidine. The N-terminal amino group was then derivatised with S-Acetylmercaptoacetic acid (SAMA) group using 5 equiv of SAMA-OPfp and 5 equiv of HOBt. The reaction was monitored by the trinitrobenzene sulphonic acid (TNBSA) test. When a negative TNBSA test was returned the resin was washed (5×DMF, 3×DCM and 3× diethyl ether). The resin was then dried under vacuum. Cleavage of peptides from the resin support was performed using TFA:phenol:TIPS:EDT:water (92:2:2:2:2) cleavage cocktail for 2.5 hours or 4 hours depending on the arginine content of the peptide. After cleavage the resin was removed by filtration and the filtrate concentrated to approximately 1 mL under a stream of nitrogen. After the peptide products were precipitated in cold ether, they were centrifuged and washed three times. The peptide precipitates were dissolved in 5 to 10 mL of water containing 0.1% v/v TFA and insoluble residue removed by centrifugation. Peptides were purified by RP-HPLC.

A number of different chemical moieties can be used for derivatising peptides for conjugation to proteins, these would introduced reactive groups such as; halides (bromo, chloro and iodo), maleimido, succinimidyl, hydrazinyl, oxime, thiol, which would then be used conjugate the derivatised peptide to a protein such as KgpA1 through its native cysteine residues or has been derivatised with the complementary reactive group that allows the chemical ligation to proceed to form a peptide-protein conjugate.

Conjugation of SAMA-Peptides to KA1.

To a solution, containing 10 mg/mL of recombinant KA1 or other adhesin domain of the RgpA-Kgp complex in phosphate-buffered saline (0.1M sodium phosphate, 0.9% NaCl, pH 7.4) was added 0.1 mL of a 1% w/v solution of m-maleimido benzoyl-N-hydroxysuccinimide ester (MBS) in DMF. After 30 min unreacted MBS was removed and MBS-modified KA1 collected by gel filtration using a PD10 column (Pharmacia, NSW, Australia) equilibrated in conjugation buffer (0.1M sodium phosphate, 5 mM EDTA; pH 6.0). Purified SAMA-peptide (1.3 µmole) was dissolved in 200 µL 6M guanidine HCl containing 0.5 M Tris; 2 mM EDTA, pH 6.0 and diluted with 800 µL MilliQ water and deprotected in-situ by addition of 254 of 2M $NH_2OH$ (40 equiv) dissolved in MilliQ water. The collected MBS-KA1 was immediately reacted with deprotected SAMA-peptide and stirred for one hour at room temperature. The peptide-KA1 conjugate was separated from unreacted peptide by gel filtration using a PD10 column equilibrated in PBS pH 7.4 and lyophilized. The reaction was monitored using the Ellmans test.

Example 7

Preparation of Antibodies

Polyclonal antiserum to recombinant proteins are raised in mice by immunising with the proteins subcutaneously. The mice are immunised at day 0 with 251 g of protein in incomplete Freund's adjuvant and day 30 with 25 µg of protein in incomplete Freund's adjuvant. Immunisations are carried out using standard procedures. Polyclonal antisera having a high titer against the proteins are obtained. If desired monoclonal antibodies directed specifically against recombinant proteins are obtained using standard procedures.

Example 8

Immunization for the Generation of Antibodies

BALB/c mice or CD1 (Swiss out bred mices) 6-8 weeks old (10 mice per group) were immunized subcutaneously (s.c. 100 µL) with either 50 µg of the KAS2-LA1 chimera and the antigen emulsified in incomplete Freund's adjuvant (IFA). After 30 days the mice were boosted with antigen (s.c. injection, emulsified in IFA) and 12 days later the mice were killed and cardiac bled to collect sera.

Determination of Subclass Antibody by an ELISA.

To determine the subclass antibody responses of mouse sera, enzyme-linked immunosorbent assays (ELISAs) were performed in triplicate using a 5-µg/ml solution of KAS2-LA1 chimera or formalin inactivated P. gingivalis W50 or the RgpA-Kgp complex in phosphate-buffered saline (PBS) (0.01 M $Na_2HPO_4$, 1.5 mM $KH_2PO_4$, 0.15 M NaCl), pH 7.0, containing 0.1% (vol/vol) Tween 20 (PBST) to coat wells of flat-bottom polyvinyl microtiter plates (Dynatech Laboratories, McLean, Va.). After removal of the coating solution, PBST containing 2% (wt/vol) skim milk powder was added to wells to block the uncoated plastic for 1 h at room temperature. After the wells were washed four times with PBST, serial dilutions of mouse sera in PBST containing 0.5% (wt/vol) skim milk (SK-PBST) were added to each well and incubated for 16 h at room temperature. After the wells were washed six times with PBST, a 1/2,000 dilution of goat IgG to mouse IgM, IgA, IgG1, IgG2a, IgG2b, or IgG3 (Sigma, New South Wales, Australia) was added in SK-PBST and allowed to bind for 2 h at room temperature. Plates were washed six times in PBST, and a 1/5,000 dilution of horseradish peroxidase-conjugated rabbit anti-goat immunoglobulin (Sigma, New South Wales, Australia) in SK-PBST was added to each well and incubated for 1 h at room temperature. After the wells were washed six times with PBST, bound antibody was detected by the addition of 100 µl of ABTS substrate [0.9 mM 2,2'-azino-bis(3-ethylbenz-thiazoline-6) sulfonic acid in 80 mM citric acid containing 0.005% (vol/vol) hydrogen peroxide, pH 4.0]

to each well. The optical density at 415 nm was measured using a microplate reader (Bio-Rad microplate reader, model 450).

Antibody Subclass Responses Induced by Immunization with the Recombinant Protein KAS2-KLA1 in Outbred (CD1, Swiss) Mice.

Figure 6:
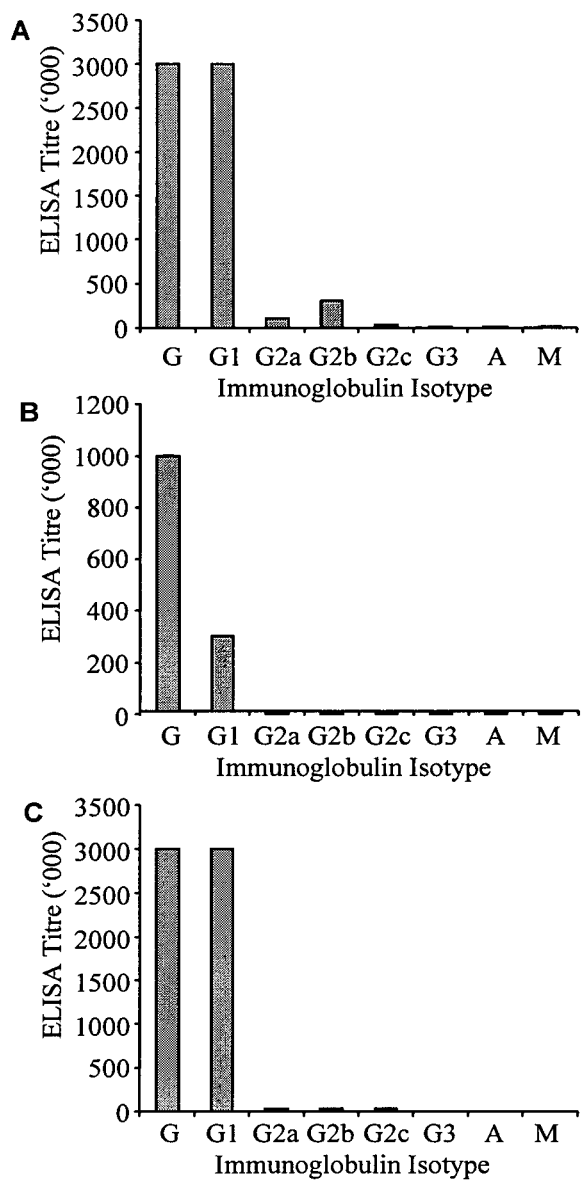
FIG. 6. Chimera AS2-LA1 induces an antibody response in outbred mice that recognises P. gingivalis whole cells and the RgpA-Kgp complex. CD1 outbred mice were immunised with chimera AS2-LA1 (50 mg/mouse) and the collected sera used in ELISA with AS2-LA1 (A), formalin killed P. gingivalis strain W50 (B) and RgpA-Kgp complex (C) as the absorbed antigens. In this figure KAS2-KLA1 is shown as AS2-LA1. The titer for each immunoglobulin isotype to each antigen was determined and the data expressed as the ELISA titer ('000) obtained minus double the background level, with each titer representing the mean±standard deviation of three values.

CD1 (Swiss) mice were immunised with the KAS2-LA1 chimera, bled and the sera collected by centrifugation. FIG. 6 shows the antibody subclass reactivity to KAS2-LA1 chimera, formalin-killed *P. gingivalis* W50 cells and the RgpA-Kgp complex. The KAS2-LA1 chimera induced a strong IgG antibody with a predominant IgG1 antibody response that recognised the KAS2-LA1 chimera and cross reacted strongly with FK *P. gingivalis* W50 cells and the RgpA-Kgp complex (FIG. 6). Furthermore, the KAS2-LA1 chimera induced only weak immunoreactive IgG2a, IgG2b and IgG3 antigen-specific antibodies (FIG. 6).

Example 9

Development of a kgp Structural Model and Identification of Active Site Surface Accessible Sequences Our work has shown that Kgp proteinase active site peptides are highly immunogenic and induce high levels of protection against *P. gingivalis*-induced bone loss. In an attempt to identify further proteinase active site peptides as vaccine candidates a model of the catalytic domain of Kgp was developed using the Orchestrar suite of programs within Sybyl7.3 (FIG. 7). The model is based on PDB structure 1crv of the RgpB protease from *P. gingivalis*, the proteins have a 23.58% pairwise identity and the Z-score is 25.09 (a high-confidence model). The Meta-PPisp protein interaction server predicts two protein-protein interaction surfaces for Kgp: the substrate binding surface (as in RgpB), and a second surface unique to Kgp. The major differences between the RgpB and Kgp models are in the loops that frame the second interaction surface and a 19-residue gap (Val526 to Phe545) that couldn't be modelled in Kgp that falls within the second interaction surface. FIG. 7 shows the Kgp model with the thicker ribbons showing surface accessible sequences around the proteinase active site of Kgp, the surface accessible sequences were found to be Asp388-Gln394, Leu421-Ala423, Ala443-Glu447 with Ala451, Asn510-Trp513, and Ile570-Gly577 with Tyr580. From the model (FIG. 6) it is evident that along with KAS2 (A) three other sequences KAS4 (Asp388-Val395) (B), KAS5 (Asn510-Asp516) (C) and KAS6 (Ile570-Tyr580) (D) are prominent and of sufficient length to be vaccine targets. Thus a recombinant chimera protein can be produced that has each of these peptides in sequence and joined on to the N-terminus of KLA1 to produce multiKAS-KLA1, that can be used to induce an immune response and hence to protect against *P. gingivalis* related diseases or conditions.

Example 10

Process for Modelling Arg-X-Proteinase to Identify Immunogenic Regions Flanking the Catalytic Site The Arg-X proteinase three dimensional structure was determined according to the methods of Eichinger A, Beisel H G, Jacob U, Huber R, Medrano F J, Banbula A, Potempa J, Travis J, Bode W. Crystal structure of gingipain R: an Arg-specific bacterial cysteine proteinase with a caspase-like fold. EMBO J. 1999 Oct. 15; 18(20):5453-62

Example 11

The following is an example of a toothpaste formulation containing antibodies.

| Ingredient | % w/w |
|---|---|
| Dicalcium phosphate dihydrate | 50.0 |
| Glycerol | 20.0 |
| Sodium carboxymethyl cellulose | 1.0 |
| Sodium lauryl sulphate | 1.5 |
| Sodium lauroyl sarconisate | 0.5 |
| Flavour | 1.0 |
| Sodium saccharin | 0.1 |
| Chlorhexidine gluconate | 0.01 |
| Dextranase | 0.01 |
| Goat serum containing specific antibodies | 0.2 |
| Water | balance |

Example 12

The following is an example of a toothpaste formulation.

| Ingredient | % w/w |
|---|---|
| Dicalcium phosphate dihydrate | 50.0 |
| Sorbitol | 10.0 |
| Glycerol | 10.0 |
| Sodium carboxymethyl cellulose | 1.0 |
| Sodium lauryl sulphate | 1.5 |
| Sodium lauroyl sarconisate | 0.5 |
| Flavour | 1.0 |
| Sodium saccharin | 0.1 |
| Sodium monofluorophosphate | 0.3 |
| Chlorhexidine gluconate | 0.01 |
| Dextranase | 0.01 |
| Bovine serum containing specific antibodies | 0.2 |
| Water | balance |

Example 13

The following is an example of a toothpaste formulation.

| Ingredient | % w/w |
|---|---|
| Dicalcium phosphate dihydrate | 50.0 |
| Sorbitol | 10.0 |
| Glycerol | 10.0 |
| Sodium carboxymethyl cellulose | 1.0 |
| Lauroyl diethanolamide | 1.0 |
| Sucrose monolaurate | 2.0 |
| Flavour | 1.0 |
| Sodium saccharin | 0.1 |
| Sodium monofluorophosphate | 0.3 |
| Chlorhexidine gluconate | 0.01 |
| Dextranase | 0.01 |
| Bovine milk Ig containing specific antibodies | 0.1 |
| Water | balance |

Example 14

The following is an example of a toothpaste formulation.

| Ingredient | % w/w |
| --- | --- |
| Sorbitol | 22.0 |
| Irish moss | 1.0 |
| Sodium Hydroxide (50%) | 1.0 |
| Gantrez | 19.0 |
| Water (deionised) | 2.69 |
| Sodium Monofluorophosphate | 0.76 |
| Sodium saccharine | 0.3 |
| Pyrophosphate | 2.0 |
| Hydrated alumina | 48.0 |
| Flavour oil | 0.95 |
| Mouse monoclonal antibodies | 0.3 |
| sodium lauryl sulphate | 2.00 |

Example 15

The following is an example of a liquid toothpaste formulation.

| Ingredient | % w/w |
| --- | --- |
| Sodium polyacrylate | 50.0 |
| Sorbitol | 10.0 |
| Glycerol | 20.0 |
| Flavour | 1.0 |
| Sodium saccharin | 0.1 |
| Sodium monofluorophosphate | 0.3 |
| Chlorhexidine gluconate | 0.01 |
| Ethanol | 3.0 |
| Equine Ig containing specific antibodies | 0.2 |
| Linolic acid | 0.05 |
| Water | balance |

Example 16

The following is an example of a mouthwash formulation.

| Ingredient | % w/w |
| --- | --- |
| Ethanol | 20.0 |
| Flavour | 1.0 |
| Sodium saccharin | 0.1 |
| Sodium monofluorophosphate | 0.3 |
| Chlorhexidine gluconate | 0.01 |
| Lauroyl diethanolamide | 0.3 |
| Rabbit Ig containing specific antibodies | 0.2 |
| Water | balance |

Example 17

The following is an example of a mouthwash formulation.

| Ingredient | % w/w |
| --- | --- |
| Gantrez S-97 | 2.5 |
| Glycerine | 10.0 |
| Flavour oil | 0.4 |
| Sodium monofluorophosphate | 0.05 |
| Chlorhexidine gluconate | 0.01 |
| Lauroyl diethanolamide | 0.2 |
| Mouse monoclonal antibodies | 0.3 |
| Water | balance |

Example 18

The following is an example of a lozenge formulation.

| Ingredient | % w/w |
| --- | --- |
| Sugar | 75-80 |
| Corn syrup | 1-20 |
| Flavour oil | 1-2 |
| NaF | 0.01-0.05 |
| Mouse monoclonal antibodies | 0.3 |
| Mg stearate | 1-5 |
| Water | balance |

Example 19

The following is an example of a gingival massage cream formulation.

| Ingredient | % w/w |
| --- | --- |
| White petrolatum | 8.0 |
| Propylene glycol | 4.0 |
| Stearyl alcohol | 8.0 |
| Polyethylene Glycol 4000 | 25.0 |
| Polyethylene Glycol 400 | 37.0 |
| Sucrose monostearate | 0.5 |
| Chlorohexidine gluconate | 0.1 |
| Mouse monoclonal antibodies | 0.3 |
| Water | balance |

Example 20

The following is an example of a chewing gum formulation.

| Ingredient | % w/w |
| --- | --- |
| Gum base | 30.0 |
| Calcium carbonate | 2.0 |
| Crystalline sorbitol | 53.0 |
| Glycerine | 0.5 |
| Flavour oil | 0.1 |
| Mouse monoclonal antibodies | 0.3 |
| Water | balance |

Example 21

The following is an example of a pharmaceutical formulation

| Ingredient | % w/w |
| --- | --- |
| Humanised specific monoclonal antibodies | 10 |
| Sterile phosphate buffered saline | 90 |

Example 22

The following is an example of a periodontal gel formulation.

| Ingredient | % w/w |
|---|---|
| Pluronic F127 | 20.0 |
| Stearyl alcohol | 8.0 |
| Specific antibodies | 3.0 |
| Colloidal silicon dioxide (Aerosil 200) | 1.0 |
| Chlorhexidine gluconate | 0.1 |
| Water | balance |

Example 23

The following is an example of a periodontal gel formulation.

| Ingredient | % w/w |
|---|---|
| Pluronic F127 | 20.0 |
| Stearyl alcohol | 8.0 |
| Specific antibodies | 3.0 |
| Colloidal silicon dioxide (Aerosil 200) | 1.0 |
| Oxantel pamoate | 0.1 |
| Water | balance |

It should be understood that while the invention has been described in details herein, the examples are for illustrative purposes only. Other modifications of the embodiments of the present invention that are obvious to those skilled in the art of molecular biology, dental diagnostics, and related disciplines are intended to be within the scope of the invention.

It will be understood that the invention disclosed and defined in this specification extends to all alternative combinations of two or more of the individual features mentioned or evident from the text or drawings. All of these different combinations constitute various alternative aspects of the invention.

REFERENCES

1. McKee, A. S., A. S. McDermid, A. Baskerville, A. B. Dowsett, D. C. Ellwood, and P. D. Marsh. 1986. Effect of hemin on the physiology and virulence of *Bacteroides gingivalis* W50. *Infect. Immun.* 52:349-355.
2. Slots, J. 1982. *Importance of black-pigmented Bacteroides in human periodontal disease. Host parasite interactions in periodontal diseases.* American Society for Microbiology.
3. O'Brien-Simpson, N. M., R. Pathirana, R. A. Paolini, Y.-Y. Chen, P. D. Veith, T. V., R. N. Pike, N. Alley, and E. C. Reynolds. 2005. An immune response directed to proteinase and adhesin functional epitopes protects against *Porphyromonas gingivalis*-induced bone loss. *Journal of Immunology* 175:3980-3989.
4. Baker, P. J., R. T. Evans, and D. C. Roopenian. 1994. Oral infection with *Porphyromonas gingivalis* and induced alveolar bone loss in immunocompetent and severe combined immunodeficient mice. *Arch Oral Biol* 39:1035-1040.

It will be understood that the invention disclosed and defined in this specification extends to all alternative combinations of two or more of the individual features mentioned or evident from the text or drawings. All of these different combinations constitute various alternative aspects of the invention.

---

The invention claimed is:

1. A method of treating a disease or condition associated with the presence of *P. gingivalis* in an oral tissue of a subject, comprising
   administering to the subject an anti-inflammatory agent and/or an antimicrobial agent, and
   administering to the subject an immunogen that induces an immune response against *P. gingivalis*, wherein the immunogen is administered after the agent.

2. The method of claim 1, comprising administering an anti-inflammatory agent in an amount effective to reduce inflammation of the oral tissue of said subject.

3. The method of claim 1, comprising administering an antimicrobial agent in an amount effective to remove microorganisms or fragments thereof from the oral tissue of said subject.

4. The method of claim 1, wherein the anti-microbial agent is an inhibiting agent of fumarate reductase.

5. The method of claim 1, wherein the anti-microbial agent is selected from the group consisting of oxantel, morantel and thiabendazole.

6. The method of claim 1, wherein the immunogen is a *P. gingivalis* chimeric peptide or fusion protein.

7. The method of claim 6, wherein the *P. gingivalis* chimeric peptide or fusion protein is selected from the group consisting of KAS1-KsA1 and KAS2-KLA1.

8. The method of claim 1, wherein the agent and/or immunogen is administered systemically.

9. The method of claim 1, wherein the agent and/or immunogen is administered directly to oral tissue.

10. The method of claim 1, wherein the immunogen is administered one to two weeks after the agent.

11. The method of claim 1, wherein the anti-inflammatory agent is administered at a time when the oral tissue of the subject is inflamed due to chronic periodontitis associated with *P. gingivalis* infection.

12. The method of claim 1, wherein the immunogen is administered at a time when the oral tissue of the subject is not inflamed.

13. The method of claim 1, wherein the immunogen induces an antibody response that is predominantly a Th2 response.

14. The method of claim 1, further comprising performing a dental procedure on said subject.

15. The method of claim 14, wherein said dental procedure is selected from the group consisting of debridement, scaling and/or root planing.

* * * * *